United States Patent
Petrou

(10) Patent No.: US 12,259,378 B2
(45) Date of Patent: Mar. 25, 2025

(54) DYNAMIC CLAMPS AND METHODS OF USE THEREOF

(71) Applicant: Praxis Precision Medicines, Inc., Boston, MA (US)

(72) Inventor: Steven Petrou, Eltham (AU)

(73) Assignee: Praxis Precision Medicines, Inc., Boston, MA (US)

( * ) Notice: Subject to any disclaimer, the term of this patent is extended or adjusted under 35 U.S.C. 154(b) by 1156 days.

(21) Appl. No.: 17/058,978

(22) PCT Filed: May 28, 2019

(86) PCT No.: PCT/US2019/034171
§ 371 (c)(1),
(2) Date: Nov. 25, 2020

(87) PCT Pub. No.: WO2019/227096
PCT Pub. Date: Nov. 28, 2019

(65) Prior Publication Data
US 2021/0215665 A1    Jul. 15, 2021

Related U.S. Application Data

(60) Provisional application No. 62/676,403, filed on May 25, 2018.

(51) Int. Cl.
*G01N 33/487*    (2006.01)

(52) U.S. Cl.
CPC . *G01N 33/48728* (2013.01); *G01N 2333/705* (2013.01)

(58) Field of Classification Search
None
See application file for complete search history.

(56) References Cited

U.S. PATENT DOCUMENTS

| 2010/0088778 | A1 | 4/2010 | Mulley et al. |
| 2011/0294155 | A1* | 12/2011 | Petrou ............ G01N 33/48728 702/19 |
| 2013/0096183 | A1 | 4/2013 | Collard et al. |

FOREIGN PATENT DOCUMENTS

| WO | WO 2018/064498 A1 | 4/2018 |
| WO | WO2018064498 | * 4/2018 |

OTHER PUBLICATIONS

Wilders et al., J Physiol, 2006, 576(2): 349-359 (Year: 2006).*
International Search Report in PCT/US2019/034171, issued Aug. 27, 2019.
Berecki et al., "Dynamic Action Potential Clamp Predicts Functional Separation in Mild Familial and Severe de Novo Forms of *SCN2A* Epilepsy," Proc. Natl. Acad. Sci. U.S.A., May 29, 2018, vol. 115, No. 24, pp. 5516-5525.
Vasylyev et al., "Dynamic-Clamp analysis of Wild-Type Human $Na_v1.7$ and Erythromelalgia Mutant Channel L858H," J Neurophysiol, Jan. 8, 2014, vol. 111, pp. 1429-1443.
Maljevic et al., "Models for discovery of targeted therapy in genetic epileptic encephalopathies", *Journal of Neurochemistry*, 2017, vol. 143, pp. 30-48.

* cited by examiner

*Primary Examiner* — Brian Gangle
*Assistant Examiner* — Lakia J Jackson-Tongue
(74) *Attorney, Agent, or Firm* — McCarter & English, LLP; Jonathan M. Sparks; Yelena Margolin

(57) ABSTRACT

The present invention provides methods for determining the phenotype (e.g., gain-of-function or loss-of-function) of a mutation in an ion channel or receptor by using a dynamic voltage clamp. The invention also features methods of determining whether a mutation is a gain-of-function or loss-of-function mutation and treating a disease or disorder associated with the particular gain-of-function or loss-of-function mutation.

7 Claims, 42 Drawing Sheets

FIG. 2A
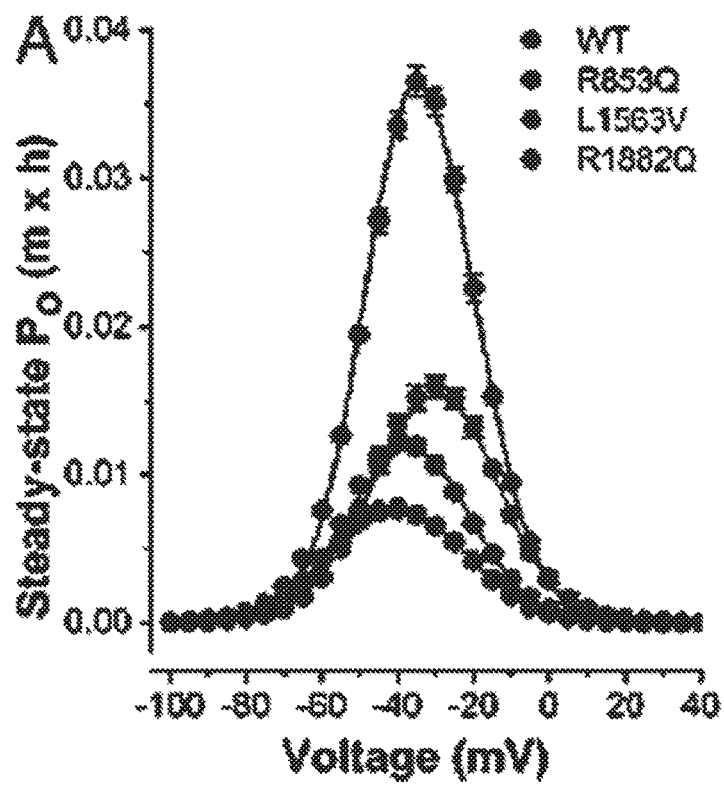
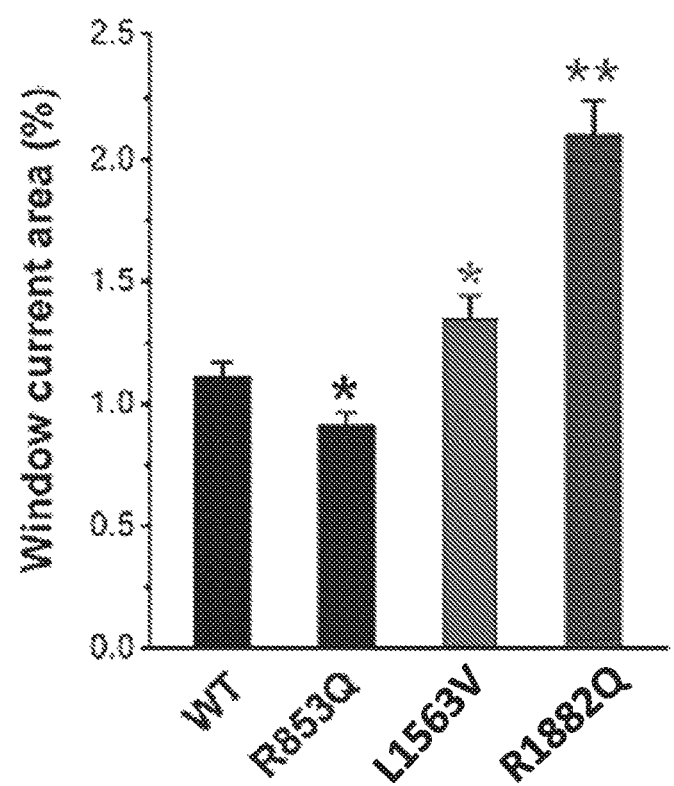

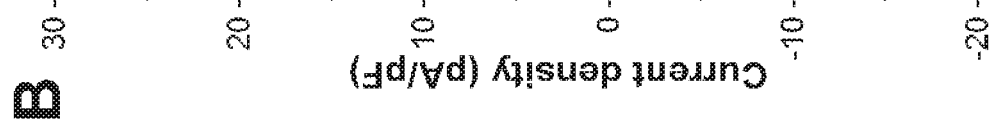
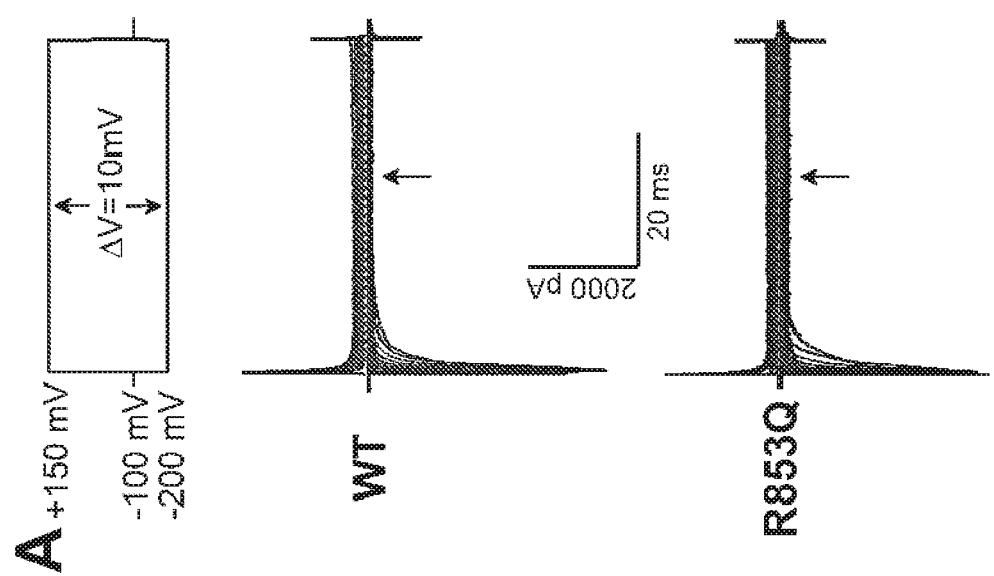

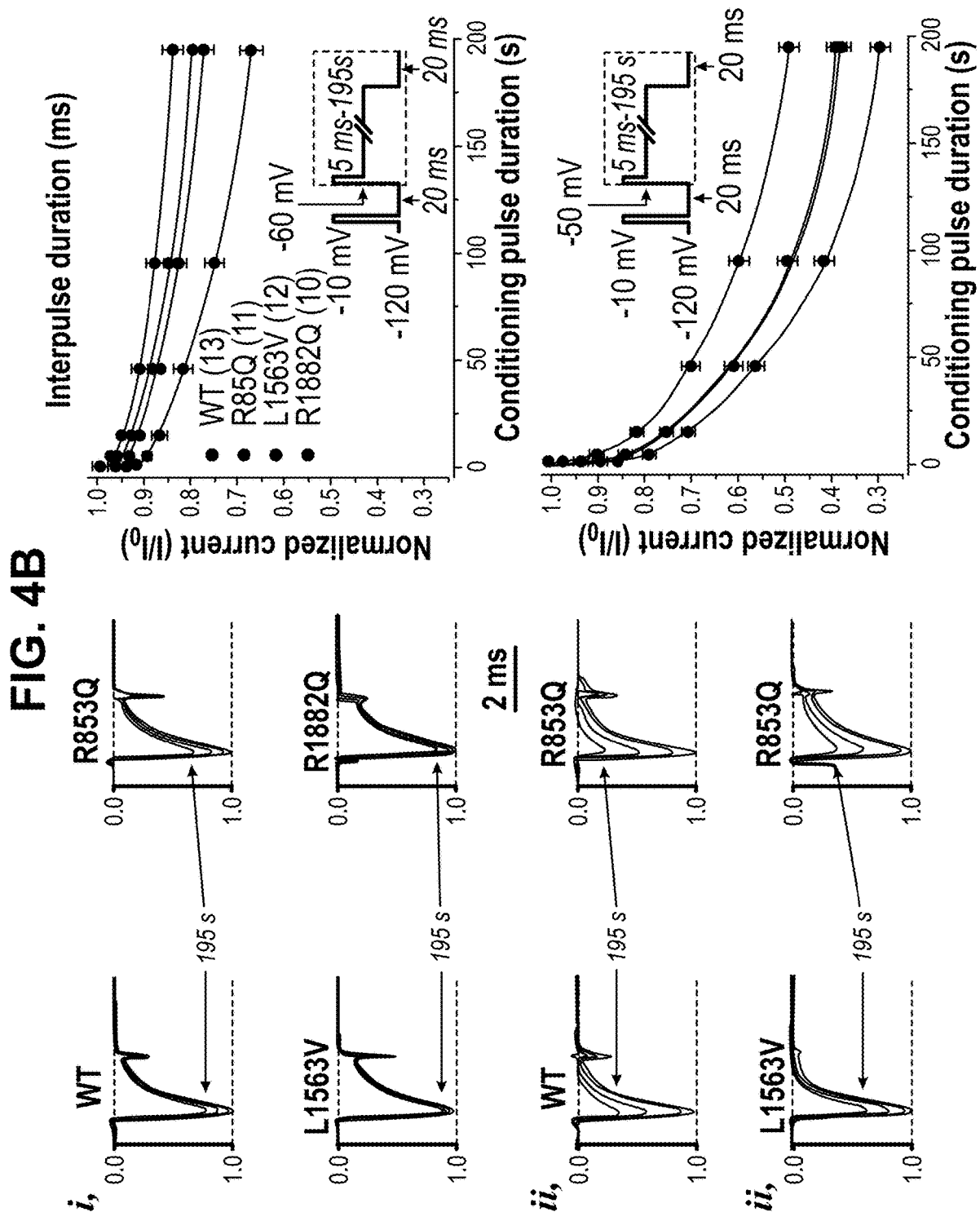

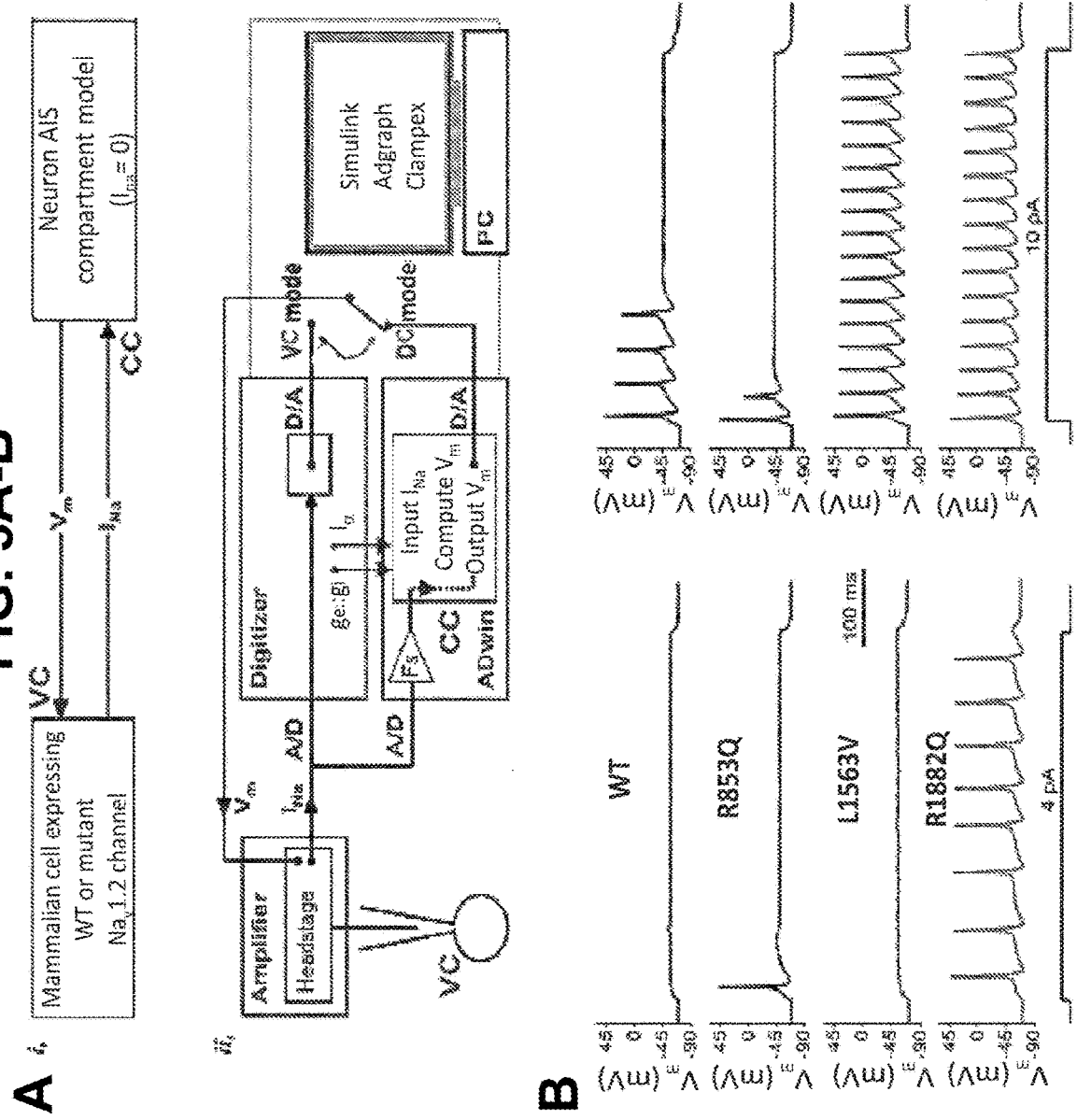

FIG. 5C-D
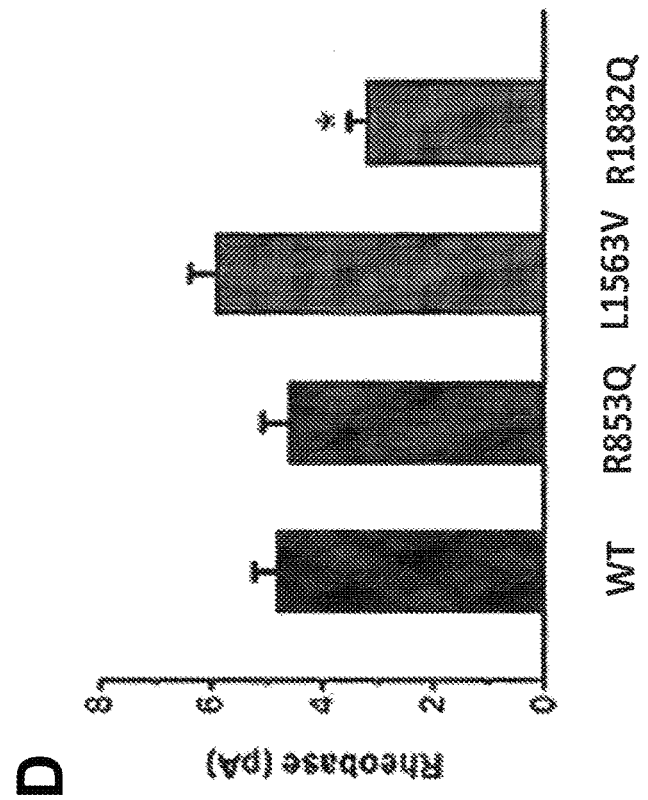
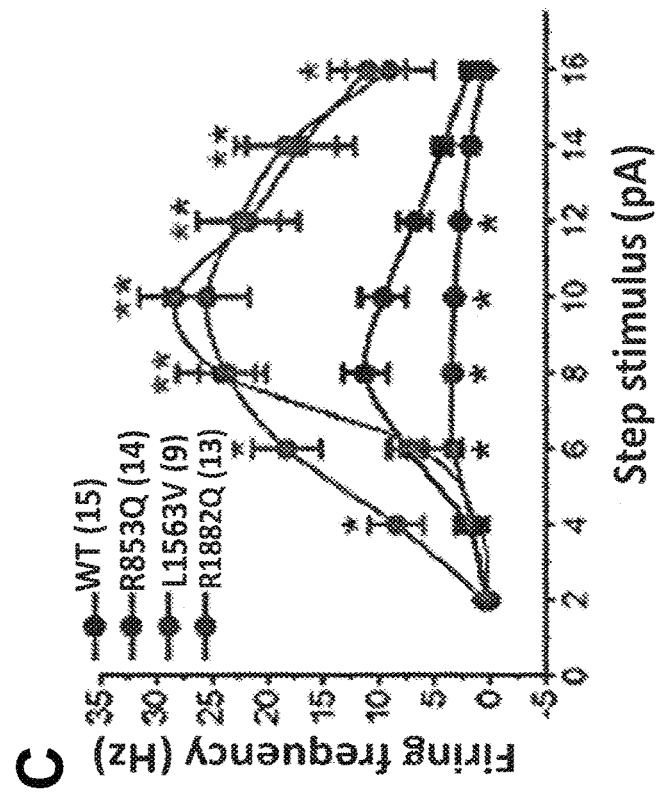

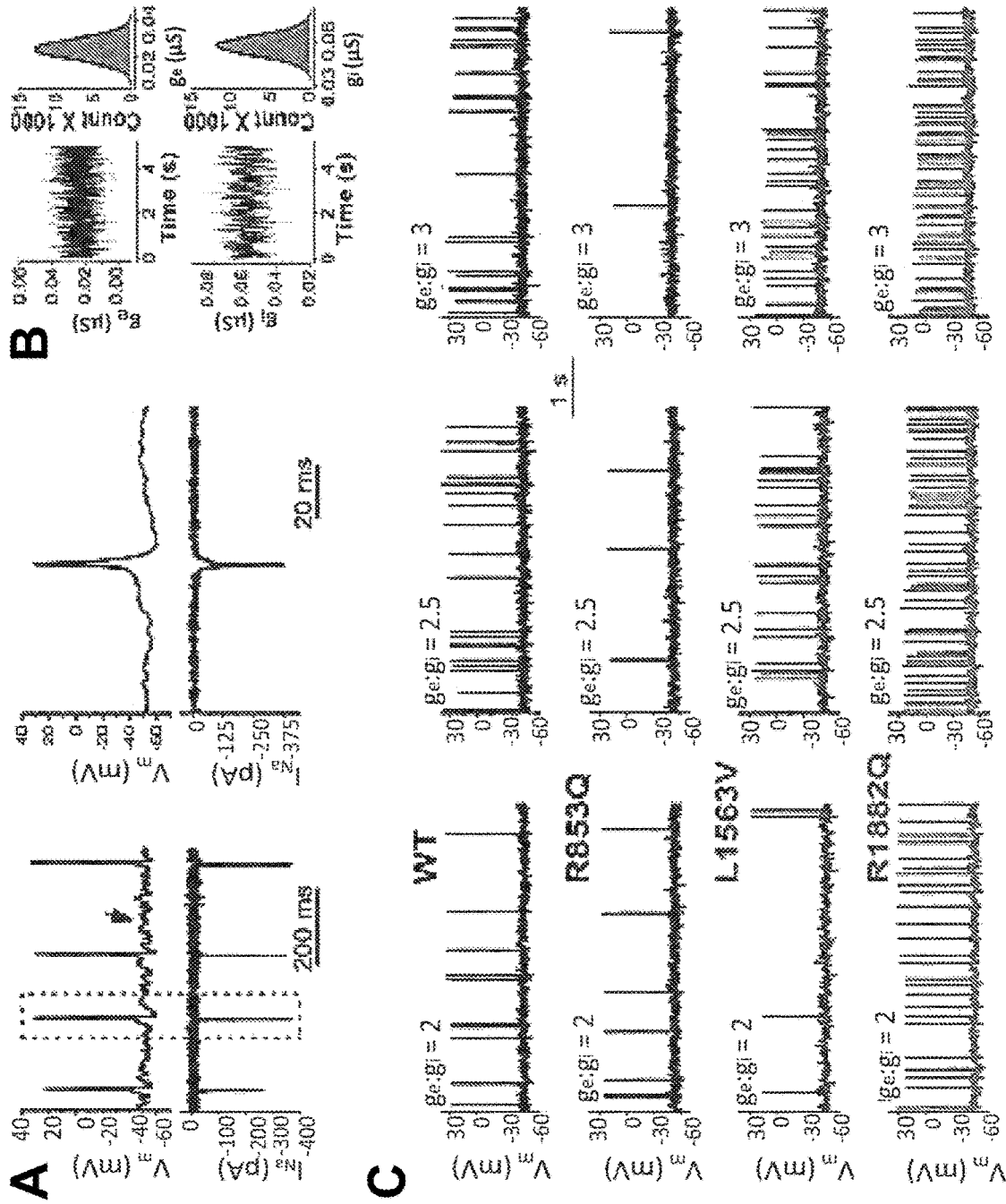
FIG. 6A-C

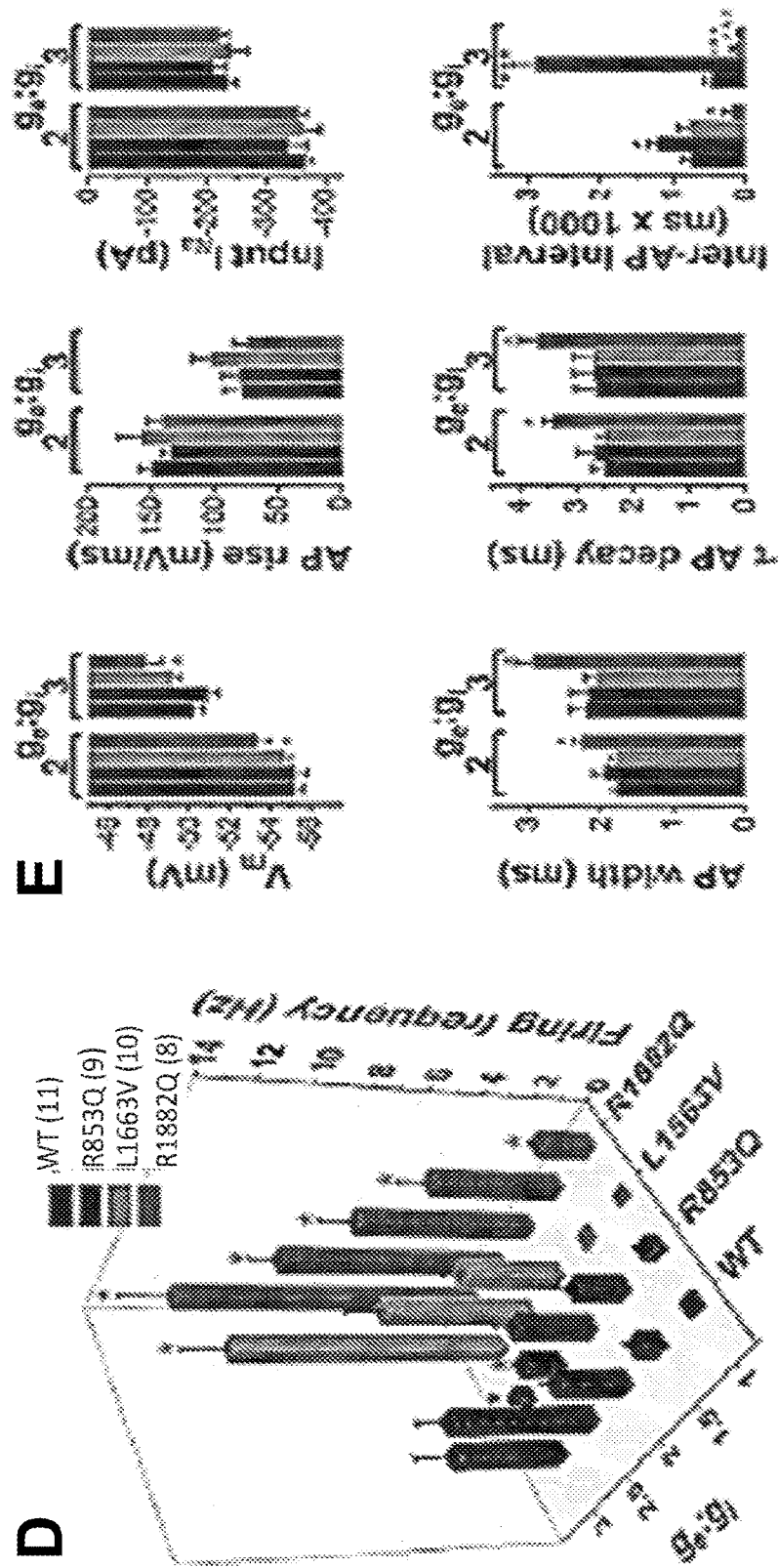
FIG. 6D-E

FIG. 7A-B
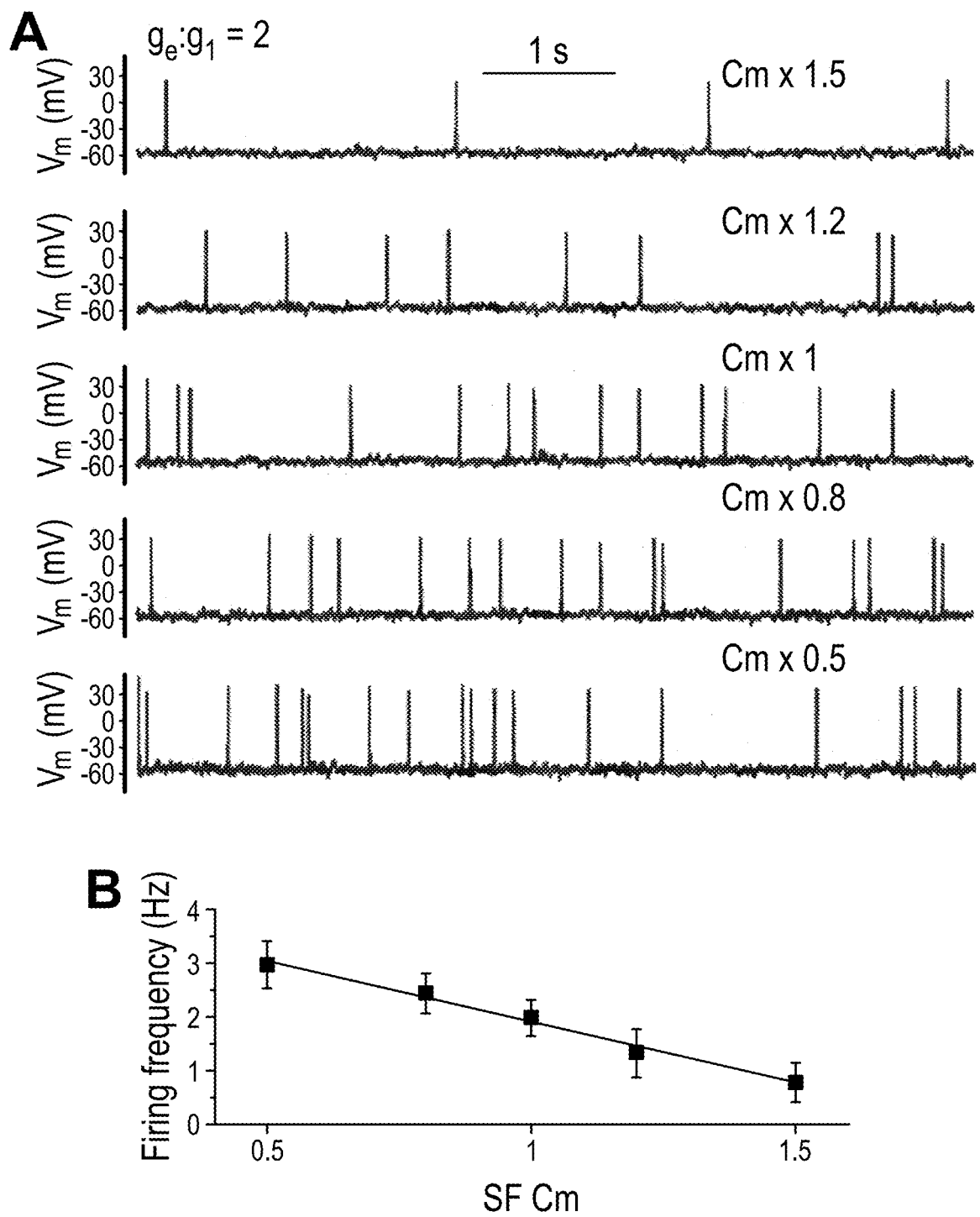

FIG. 8A-B
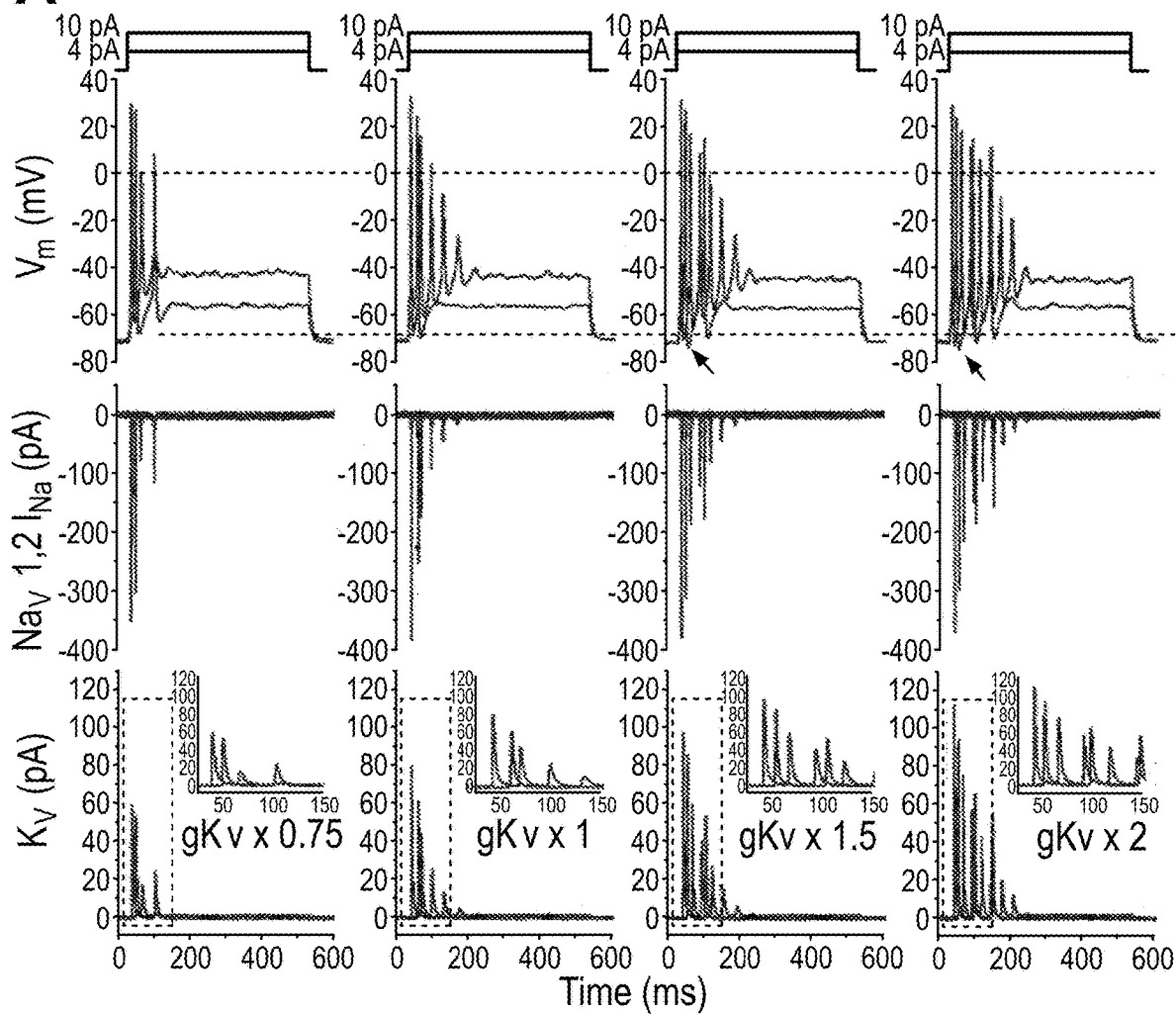
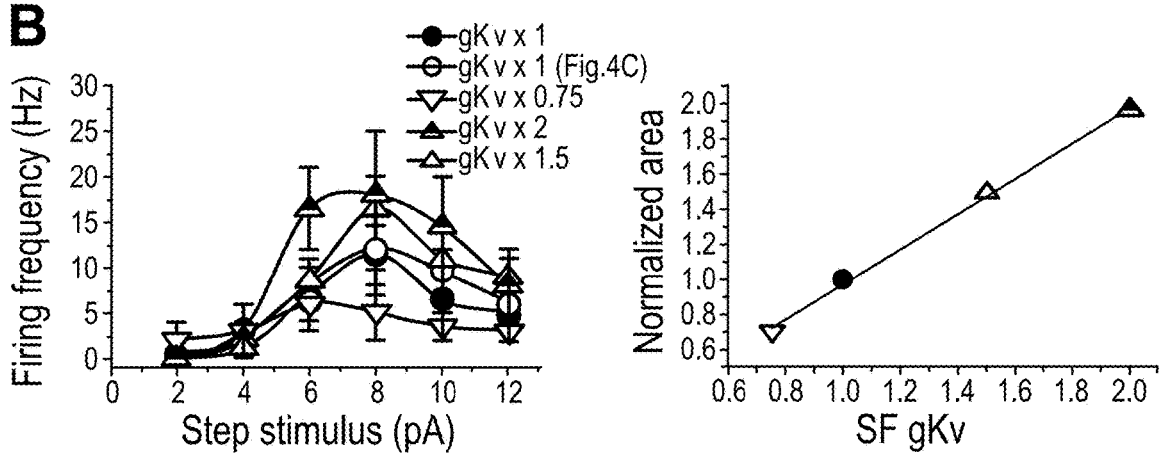

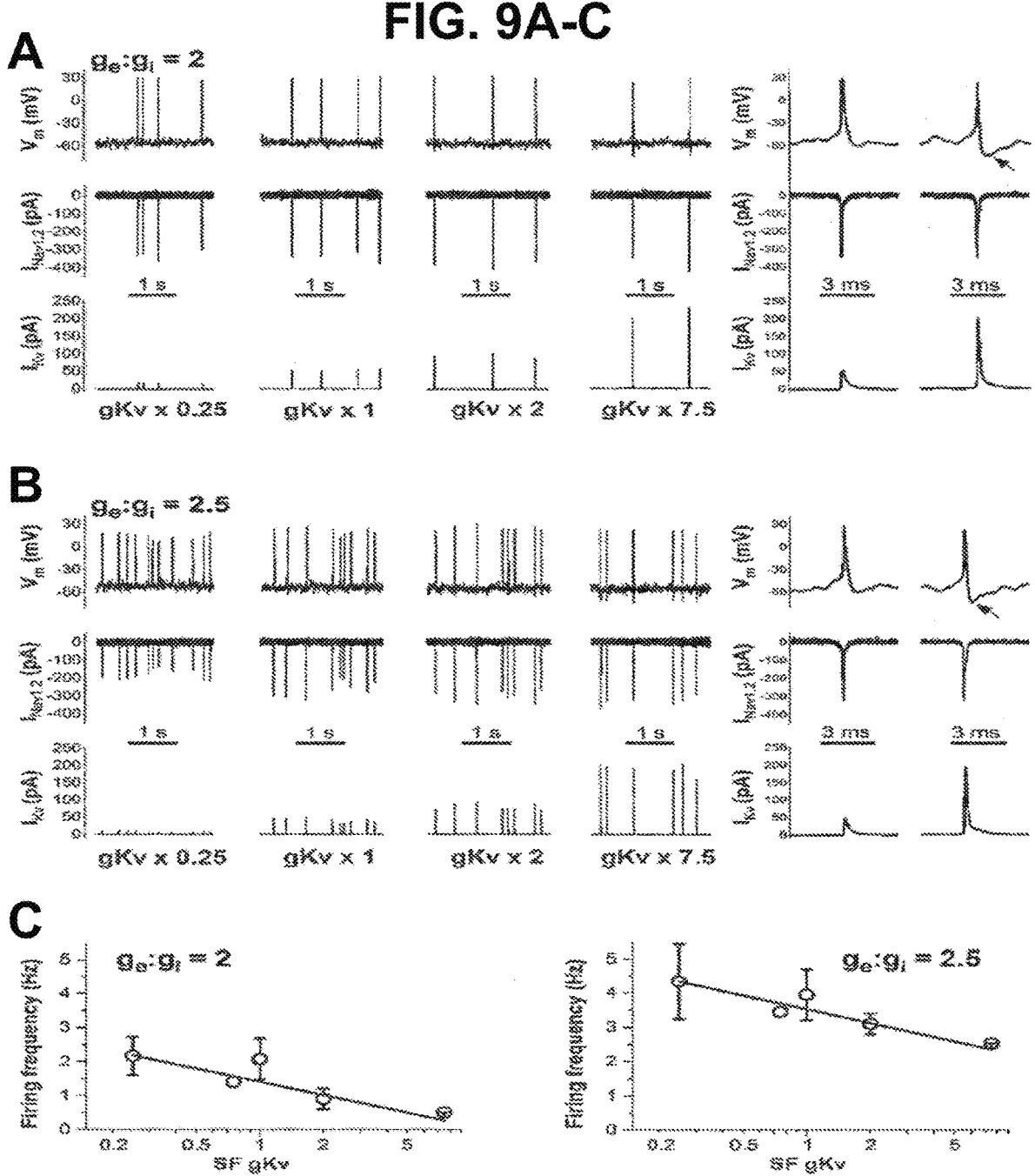
FIG. 9A-C

FIG. 10A-B
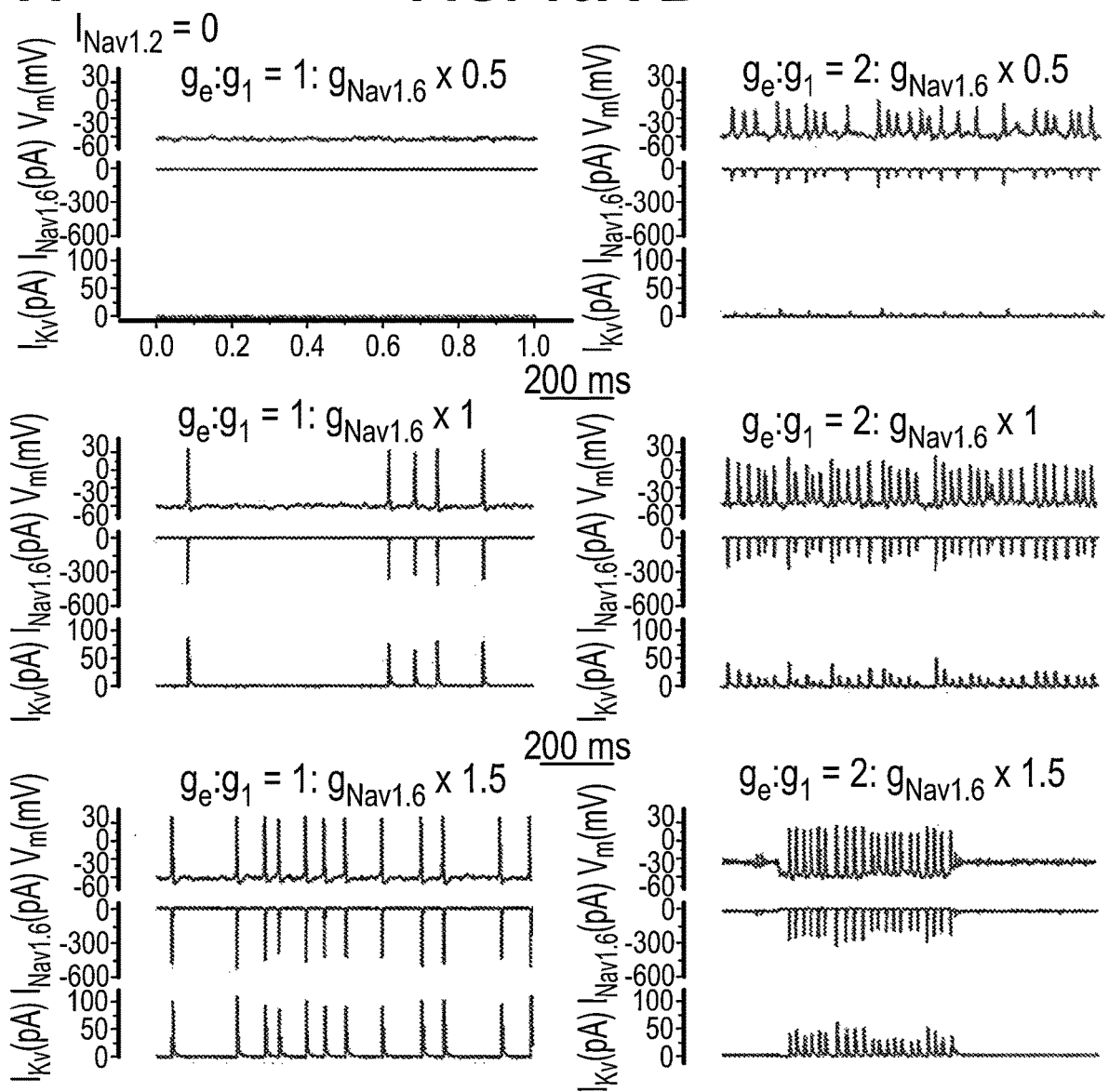
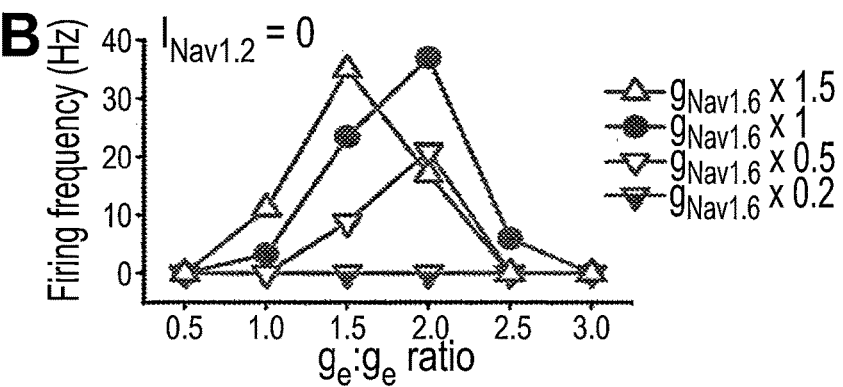

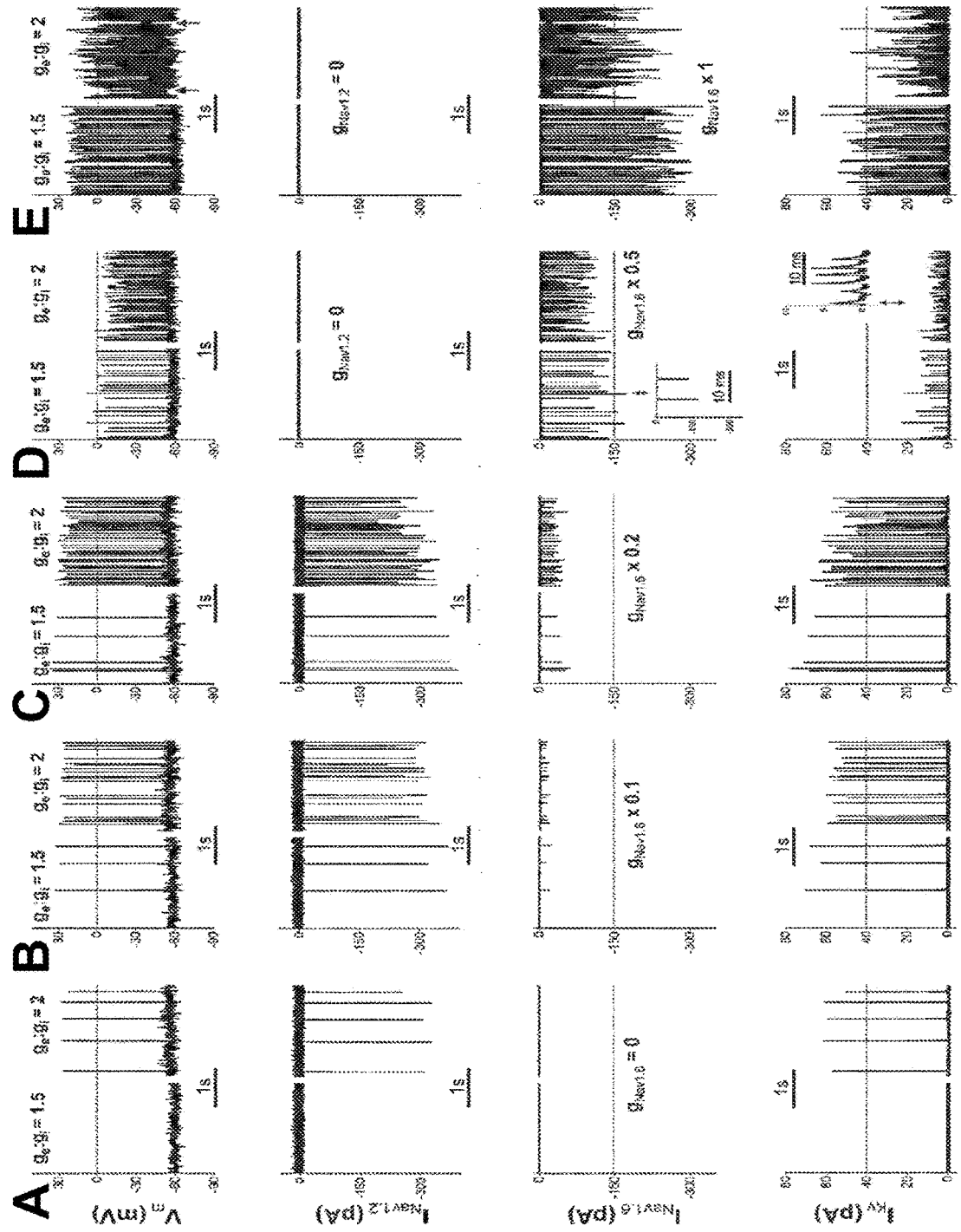
FIG. 11A-E

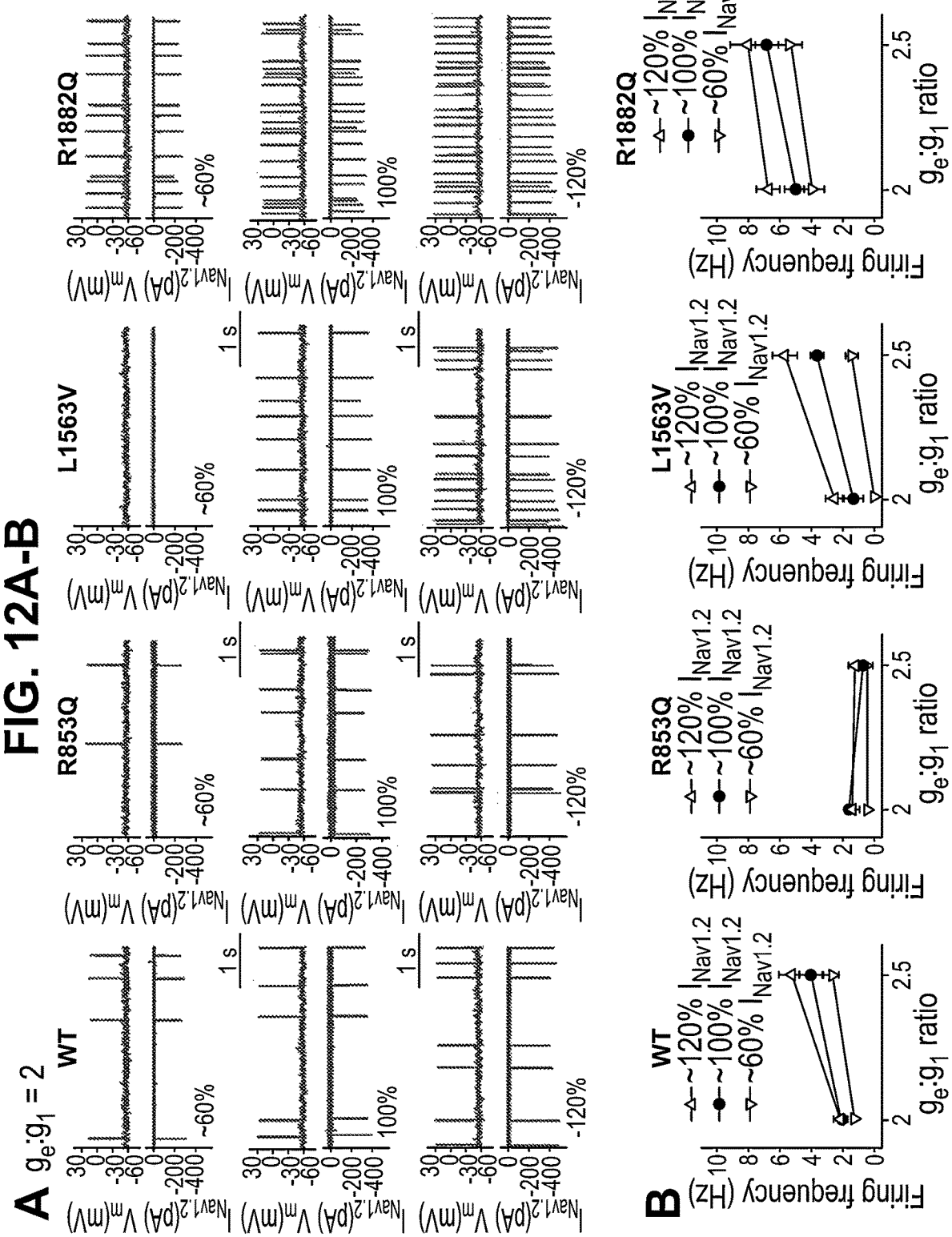
FIG. 12A-B

FIG. 13A-B
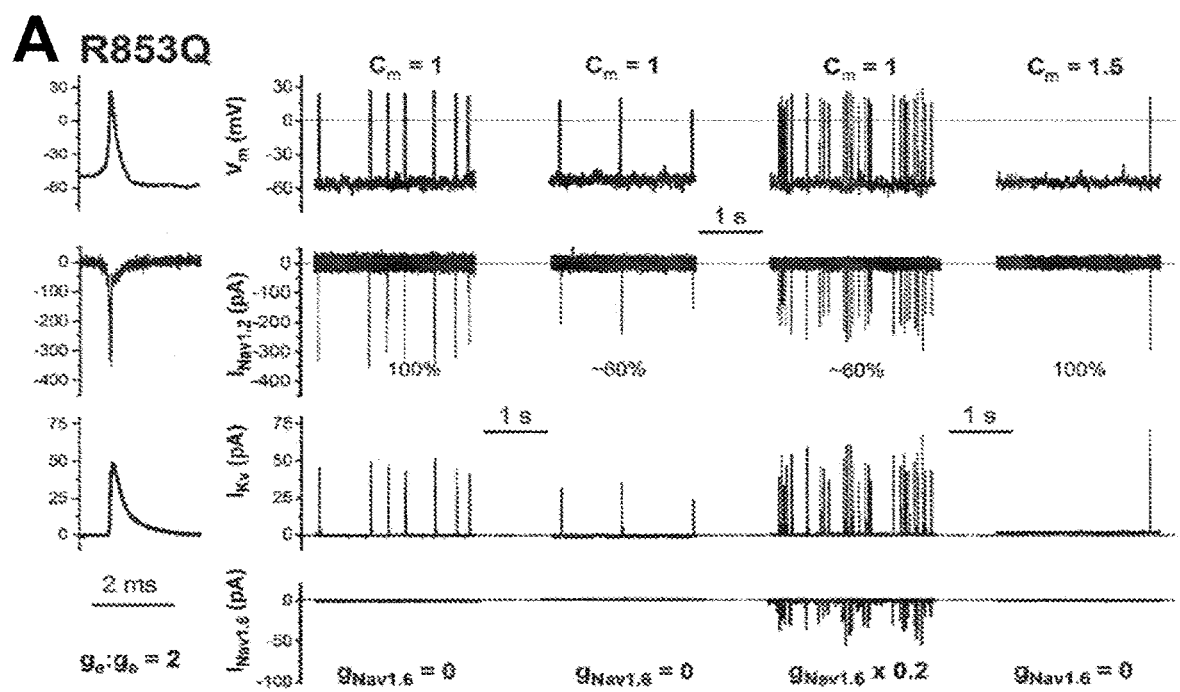
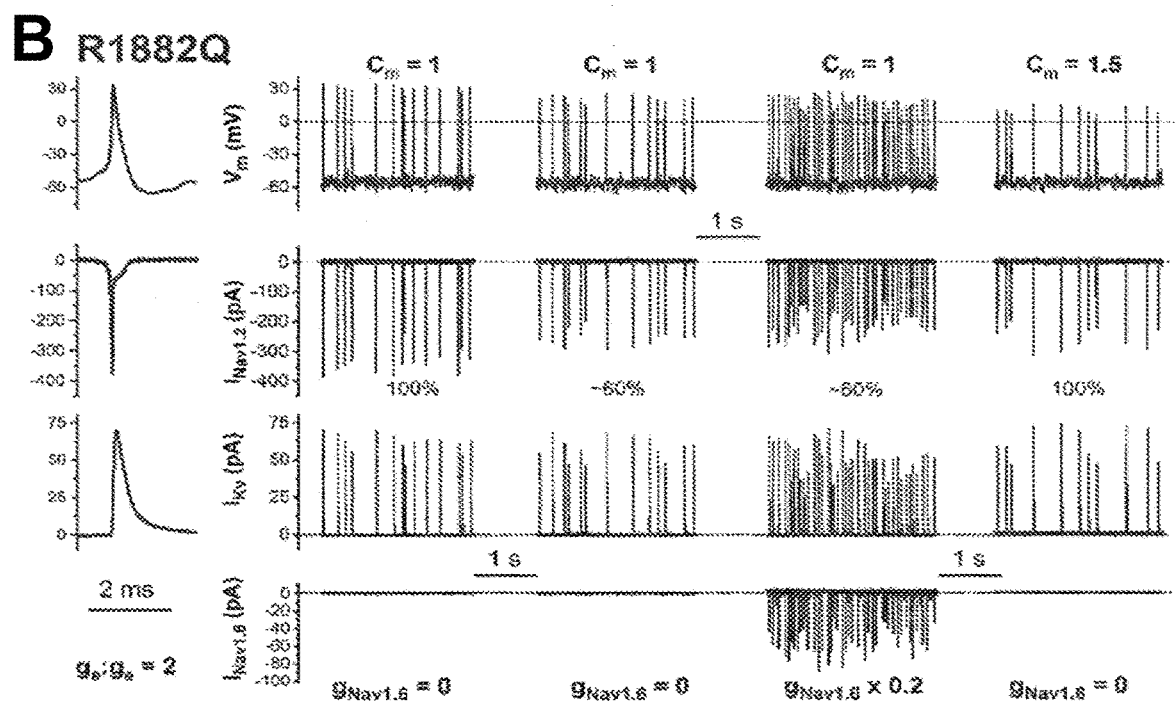

DYNAMIC CLAMPS AND METHODS OF USE THEREOF

BACKGROUND OF THE INVENTION

A number of clinically relevant diseases are caused by mutations in membrane proteins such as ion channels and receptors. Mutations in ion channels and receptors often lead to gain-of-function (GOF) or loss-of-function (LOF) phenotypes. These phenotypes often require different treatment strategies to effectively treat the disease. For example, a therapy may work for a GOF mutation but not a LOF mutation, and vice versa. However, it is not readily apparent whether a particular mutation is a GOF or LOF mutation and what the most effective therapies are, given the phenotype. Accordingly, new methods of determining whether a mutation is a GOF or LOF mutation are needed. Furthermore, new treatment methods are needed to properly diagnose and treat diseases associated with GOF and LOF mutations.

SUMMARY OF THE INVENTION

In one aspect, the invention features a method of determining whether a mutation in an ion channel or a receptor of is a gain-of-function or loss-of-function mutation. The method includes the steps of: a) providing a dynamic clamp in electrical contact with a biological cell or portion thereof including a mutant ion channel or receptor for providing a waveform; b) causing the dynamic clamp to apply a signal based on modulation of the mutant ion channel in the biological cell or portion thereof, thereby providing the waveform at the biological cell or portion thereof; and c) detecting modulation of the waveform at the biological cell or portion thereof. Modulation of the waveform is determined relative to a control. If the modulation of the waveform is increased compared to the control, then the mutation is a gain-of-function mutation, and if the modulation of the waveform is decreased compared to the control, then the mutation is a loss-of-function mutation.

The method may further include the step of treating a subject for a disease or disorder, wherein the subject has a gain-of-function mutation in the ion channel or receptor, and the treatment includes a therapy suitable for the gain-of-function mutation. Alternatively, the method may further include the step of treating a subject for a disease or disorder, wherein the subject has a loss-of-function mutation in the ion channel or receptor, and the treatment includes a therapy suitable for the loss-of-function mutation.

In another aspect, the invention features a method of treating a disease or disorder in a subject by administering to the subject a therapy in an amount and for a duration sufficient to treat the disease or disorder, wherein the subject has been previously determined to have a gain-of-function mutation in an ion channel or receptor, and wherein the therapy is suitable for the gain-of-function mutation.

In another aspect, the invention features a method of treating a disease or disorder in a subject by administering to the subject a therapy in an amount and for a duration sufficient to treat the disease or disorder, wherein the subject has been previously determined to have a loss-of-function mutation in an ion channel or receptor, and wherein the therapy is suitable for the loss-of-function mutation.

In another aspect, the invention features a method of treating a disease or disorder in a subject by determining if the subject has a gain-of-function mutation in an ion channel or receptor, and if the mutation is a gain-of-function mutation, administering to the subject a therapy suitable for the gain-of-function mutation in an amount and for a duration sufficient to treat the disease or disorder.

In another aspect, the invention features a method of treating a disease or disorder in a subject by determining if the subject has a loss-of-function mutation in an ion channel or receptor, and if the mutation is a loss-of-function mutation, administering to the subject a therapy suitable for the loss-of-function mutation in an amount and for a duration sufficient to treat the disease or disorder.

In some embodiments, the determining step includes the steps of: a) providing a dynamic clamp in electrical contact with a biological cell or portion thereof including a mutant ion channel or receptor for providing a waveform; b) causing the dynamic clamp to apply a signal based on modulation of the ion channel in the biological cell or portion thereof, thereby providing the waveform at the biological cell or portion thereof; and c) detecting modulation of the waveform at the biological cell or portion thereof, wherein modulation of the waveform is determined relative to a control, wherein if the modulation of the waveform is increased compared to the control, then the subject has a gain-of-function mutation, and if the modulation of the waveform is decreased compared to the control, then the subject has a loss-of-function mutation.

In some embodiments of any of the above aspects, the control includes a biological cell or portion thereof including a wild-type ion channel or receptor.

In some embodiments of any of the above aspects, the waveform is an action potential.

In some embodiments of any of the above aspects, the dynamic clamp applies a voltage signal to the biological cell or portion thereof, and modulation of the waveform at the biological cell or portion thereof is detected by measuring a current signal at the biological cell or portion thereof.

In some embodiments of any of the above aspects, the dynamic clamp applies a current signal to the biological cell or portion thereof, and modulation of the waveform at the biological cell or portion thereof is detected by measuring a voltage signal at the biological cell or portion thereof.

In some embodiments of any of the above aspects, the ion channel is selected from the group consisting of a sodium channel, a potassium channel, a calcium channel, or a chloride channel.

In some embodiments of any of the above aspects, the ion channel is a sodium channel.

In some embodiments of any of the above aspects, the sodium channel is an SCN channel.

In some embodiments of any of the above aspects, the SCN channel is selected from SCN1A, SCN2A, SCN3A, SCN4A, SCN5A, SCN8A, SCN9A, SCN10A, and SCN11A.

In some embodiments of any of the above aspects, the SCN channel is SCN1A.

In some embodiments of any of the above aspects, the SCN channel is SCN2A.

In some embodiments of any of the above aspects, the SCN channel is SCN8A

In some embodiments of any of the above aspects, the disease or disorder is an encephalopathy (e.g., an SCN1A, SCN2A, or SCN8A-related encephalopathy). The SCN1A-related encephalopathy may be, e.g., Dravet Syndrome, intractable childhood epilepsy with generalized tonic-clonic seizures, severe myoclonic epilepsy borderline, febrile seizures, or generalized epilepsy with febrile seizures plus. The SCN2A-related encephalopathy may be, e.g., benign familial neonatal/infantile seizures, infantile spasms, Ohtahara syndrome, epilepsy of infancy with migrating focal seizures, or early onset epileptic encephalopathy. The SCN8A-related encephalopathy may be, e.g., epileptic encephalopathy.

In some embodiments of any of the above aspects, the ion channel is a potassium channel. The potassium channel may be KCNT1. The potassium channel may be KCNQ1.

In some embodiments of any of the above aspects, the disease or disorder is a KCNT1-related disease disorder. The KCNT1-related disease or disorder may be epileptic encephalopathy (e.g., early infantile epileptic encephalopathy), malignant migrating partial seizures of infancy, or nocturnal frontal lobe epilepsy.

In some embodiments of any of the above aspects, the disease or disorder is a KCNQ1-related disease or disorder. The KCNQ1-related disease or disorder may be atrial fibrillation, familial 3, Jervell and Lange-Nielson syndrome, Long QT syndrome 1, or Short QT syndrome 2.

Definitions

The term "modulating," as used herein, refers to any form of physical or chemical change. For example, this may include activation or inhibition of a receptor, the effect of mutations on the receptor, up-regulation or downregulation of a receptor, inhibition or activation of second messenger molecules or receptor internalization. Modulation of an ion channel or receptor type includes inhibition of the ion channel or receptor type. Modulation of an ion channel or receptor type includes activation of the ion channel or receptor type. Modulation of an ion channel or receptor type also includes modulation of a subunit of the ion channel or receptor type. Selective modulation of specific subunits may be advantageous in probing mutants with specific physiological characteristics.

The term "waveform," as used herein, refers to any variation (e.g., variations in amplitude or frequency) in an electrophysiological parameter (e.g., transmembrane voltage) over time at a cell. Such variations result from modulation of a number of ion channel or receptor types at the cell. The waveform may be an action potential or synaptic event. A waveform at a biological cell is generally produced by virtue of a functional inter-relationship between a number of different types of ion channels or receptors. Modulation of one, or a group of ion channels or receptors results electrophysiological changes at the membrane of the cell, causing further ion channels to be modulated, resulting in a waveform. Ion channels including, for example, sodium channels, potassium channels, calcium channels, chloride channels and hyperpolarization activated cation channels may be involved.

The term "gain-of-function mutation," as used herein, refers to a mutation that increases the activity of a protein (e.g., ion channel or receptor) relative to the WT protein.

The term "loss-of-function mutation," as used herein, refers to a mutation that decreases the activity of a protein (e.g., ion channel or receptor) relative to the WT protein.

BRIEF DESCRIPTION OF THE DRAWINGS

FIG. 1A shows predicted transmembrane topology of $Na_v$ 1.2 channels denoting the R853Q and R1882Q mutations associated with later-onset and early-onset DEE respectively, and the L1563V mutation associated with BFNIS. Domains D1-D4 are indicated; note the positive charges on the voltage sensor (fourth segment) of each domain. FIG. 1B shows representative wild-type and mutant $I_{Na}$ traces, elicited by 20-ms depolarizing voltage steps of 5 mV increment from a HP of −120 mV (inset voltage protocol). (FIG. 1C) Current-voltage relationships. FIG. 1D shows voltage dependence of activation (squares) and inactivation (circles). The normalized conductance-voltage relationships are plotted as $G/G_{max}$ values versus voltage and are referred to as 'activation' curves. Curves were obtained by non-linear least-squares fits of Boltzmann equations (see Methods). Values of fitted parameters are indicated below each curve and summarized in Table 2. Activation was assessed using the voltage protocol described in B. Inactivation was determined from a HP of −120 mV using 100-ms conditioning steps ranging from −120 to +10 mV followed by 20-ms test pulses to −5 mV (inset), at 0.1 Hz. The number of experiments, n, are shown in Table 2.

FIGS. 2A-2C are a set of graphs showing mechanisms contributing to sodium channel dysfunction in R853Q, L1563V, and R1882Q channels. FIG. 2A shows voltage dependence of the steady-state open probability ($P_o$) (top). The m×h product was calculated for every cell using the individual $G/G_{max}$ values described in FIG. 1D, and plotted against the $V_m$. Bottom: Mean percentages of window current relative to total current in wild-type (WT) and mutant $Na_v$ 1.2 channels. Data are represented as mean±SEM (n, same as in FIG. 1D). FIG. 2B depicts demonstration of persistent inward $I_{Na}$. Top: sensitivity of persistent inward $I_{Na}$ to tetrodotoxin (TTX). Peak currents are off scale. Insets show TTX sensitive current as percentage of peak $I_{Na}$, obtained by subtraction. Bottom: mean current-voltage relationships of persistent $I_{Na}$ expressed as percentage of peak $I_{Na}$ for wild-type (n=30), R853Q (n=21), L1563V (n=14), and R1882Q (n=25). Dotted lines indicate zero current level. FIG. 2C shows typical wild-type and mutant $I_{Na}$ traces elicited at −25, −30 and −35 mV (top). Note the slower inactivation time course of R1882Q $I_{Na}$ vs. wild-type (star). Bottom: Average fast time constants (it) of $I_{Na}$ inactivation plotted against test potential. Insert: boxed $T_f$ values on an expanded scale. R1882Q channels show larger $T_f$ values versus wild-type (see data with statistics in Table 2).

FIGS. 3A-3B are a set of graphs showing inward and outward currents in CHO cells transiently expressing wild-type or R853Q Nav1.2 channels. FIG. 3A shows representative wild-type (WT) and R853Q $I_{Na}$ traces, elicited by 50-ms voltage steps of 10 mV increment from a holding potential (HP) of −100 mV (top inset). To establish presence of pore currents, current amplitude was measured at 30 ms after the onset of the step voltage command (arrow). Dotted lines indicate zero current level; P/N leak subtraction was turned off. FIG. 3B shows current densities determined at HP values of −200 and +150 mV, respectively. Increasing the concentration of guanidine-sulfate to 60 mM in the extracellular solution did not affect the current amplitude (n=3). Data are mean±SEM; n, number of experiments between parentheses.

FIGS. 4A-4B are a set of graphs showing recovery from inactivation and development of slow inactivation in CHO cells expressing WT, R853Q, L1563V, or R1882Q $Na_v$ 1.2 channels. FIG. 4A shows accelerated recovery of L1563V channels versus wild-type revealed with paired-pulse protocols of HP values of −120 or −70 mV, respectively. Left: Representative P1 (control)- and P2-elicited traces elicited from a HP of −120 mV and using recovery interpulse intervals of 0.5, 1, and 2 ms. Plots on the right show normalized wild-type and mutant peak $I_{Na}$ as a function of interpulse duration. Note the effect of HP (top: −120 mV;

bottom: −70 mV) on the time course of $I_{Na}$ recovery. Insets: voltage protocols. FIG. 4B shows enhanced slow inactivation for R853Q and reduced slow inactivation for L1563V versus wild-type channels. The extent of slow inactivation is indicated by the fractional reduction in peak $I_{Na}$ during the 2-ms test pulse (P2) relative to that recorded in the first 2-ms pre-pulse (P1). At any P2, the fraction that enters slow inactivation equals 1−P2/P1. Insets: voltage protocols with boxed areas representing the repeated voltage motif, including the time intervals of increasing duration. Note the effect of $V_m$ on slow inactivation, −60 mV (i) versus −50 mV (ii), respectively (See data with statistics in Table 2).

FIGS. 5A-5D are a set of graphs showing dynamic action potential clamp experiment implementing WT, R853Q, L1563V, or R1882Q $I_{Na}$. FIG. 5A (i) shows a schematic representation of the dynamic clamp technique used to effectively replace the in silico $I_{Na}$ of the virtual AIS compartment model with $I_{Na}$ expressed in a mammalian (CHO) cell. FIG. 5A (ii) shows that in dynamic clamp (DC) mode, $I_{Na}$ is recorded from a CHO cell, digitized A/D), scaled (Fs), and continuously applied to the virtual (model) cell as an external current input. The model cell is in current clamp (CC) mode and its $V_m$ is computed in real-time by the PC-controlled ADwin system. The computed $V_m$ is converted into an analog signal (D/A), sent back to the amplifier, and applied as a voltage clamp (VC) command to the CHO cell. Action potential firing in the model cell is triggered either by step stimulus currents ($I_{st}$) or synaptic current ($g_e$:$g_i$). The setup enables switching between dynamic clamp and conventional voltage clamp modes. FIG. 5B shows dynamic action potential clamp experiments reveal Na$_v$1.2 channel gain-of-function or loss-of-function. Action potential firing with model cell incorporating wild-type, R853Q, L1563V or R1882Q $I_{Na}$ in response to increasing $I_{st}$, in the range between 0 and 16 pA, in 2 pA increments. Representative $V_m$ changes elicited by 4 or 10 pA step currents are shown. FIG. 5C shows input-output showing the $I_{st}$ dependence of action potential firing. Data are mean±SEM; n, number of experiments between parentheses; Note the altered action potential firing of the model cell in the presence of mutant $I_{Na}$ compared with wild-type (*P<0.05). FIG. 5D shows Rheobase (*P<0.05, compared with wild-type); n, same as in C.

FIGS. 6A-6E are a set of graphs showing firing of the model cell incorporating WT, R853Q, L1563V, or R1882Q $I_{Na}$ in response to synaptic conductance input. FIG. 6A shows typical firing responses of the AIS model cell incorporating wild-type $I_{Na}$. The $V_m$ changes (upward deflections) and associated scaled input $I_{Na}$ (downward deflections) are shown. Note the $V_m$ fluctuations typical for these types of experiments (arrow). Right: boxed action potential and $I_{Na}$ on an expanded timescale. FIG. 6B shows time course and magnitude of $g_e$ (top) and $g_i$ (bottom), respectively, with an excitatory and inhibitory ($g_e$:$g_i$) ratio value of 2. Inset histograms define mean $g_e$ and $g_i$ values of 0.0238 pA and 0.0571 pA, respectively. FIG. 6C shows firing responses with $g_e$:$g_i$ values of 2, 2.5 and 3, respectively. Note the change in firing frequencies because of Na$_v$1.2 channel loss-of-function (R853Q) or gain-of-function (L1563V, R1882Q). FIG. 6D shows input-output relationships in the model cell as a function of $g_e$:$g_i$; n, number of experiments between parentheses; *P<0.05, compared with wild-type. FIG. 6E shows steady-state $V_m$, action potential (AP) upstroke velocity, input $I_{Na}$ amplitude, AP width, time course (t) of repolarization, and inter-spiking interval values, respectively, as a function of $g_e$:$g_i$. Data are mean±SEM; *P<0.05, ***P<0.001 compared with wild-type (one-way ANOVA); n, same as in D.

FIGS. 7A-7B are a set of graphs showing the effects of varying the capacitance (Cm) of the AIS compartment on firing activity. FIG. 7A shows that reducing the Cm increases the firing rate. Representative firing responses elicited by a synaptic current of excitatory ($g_e$) to inhibitory ($g_i$) conductance ratio ($g_e$:$g_i$) of 2. The amplitude of the wild-type input $I_{Nav1.2}$ was set to 350-375 pA. FIG. 7B shows the relationship between the firing frequency and scaled Cm. Data are presented as mean±SEM, n, number of independent experiments=4. Data were fit with a linear equation of type y=mx+b, where m (slope)=−2.28±0.14.

FIGS. 8A-8B are a set of graphs showing the effect of altered gKv on AIS compartment model activity in response to step current ($I_{st}$) stimulation. FIG. 8A shows representative action potential firing (upward deflections, top), elicited by 4 or 10 pA $I_{st}$ steps (top insets); associated wild-type input $I_{Nav1.2}$ (downward deflections, middle), and virtual potassium current ($I_{Kv}$) (upward deflections, bottom); note boxed $I_{Kv}$ traces on an expanded time scale. FIG. 8B shows input-output relationships with the original AIS model cell gKv scaled to the indicated values (left). Action potentials were elicited by $I_{st}$ of 500 ms duration in 2 pA increments between 2 and 12 pA. Note that the input-output curve with wild-type input $I_{Nav1.2}$ from FIG. 5C is re-plotted for comparison (grey symbols). Data are presented as mean±SEM; for each data point n 4. Note the increase of firing activity with increasing gKv values. Relative to gKv<1, the $V_m$ is more efficiently repolarized below action potential threshold with gKv>1 (arrows), facilitating the recovery of Na$_v$ channels from inactivation. This transient repolarizing effect is counteracted by the $I_{st}$ that efficiently depolarizes the $V_m$ to threshold for action potential firing. Right: Relationship between overall firing and scaled gKv, expressed as the normalized area under the corresponding input-output curve shown in the left panel (slope of the linear fit is 1.00±0.02).

FIGS. 9A-9C are a set of graphs showing the effect of scaling gKv on AIS compartment model activity in response to synaptic current stimulation. Representative examples of firing elicited with $g_e$:$g_i$=2 (FIG. 9A) or $g_e$:$g_i$=2.5 (FIG. 9B), respectively. Right: shaded boxes show $V_m$, wild-type $I_{Nav1.2}$, and $I_{Kv}$ traces on expanded time scale. FIG. 9C shows input-output relationships as a function of $g_e$:$g_i$. Note that gKv scaling produces relatively small changes in firing frequency; large gKv values transiently hyperpolarize the membrane potential (arrows). Data are presented as mean±SEM; for each data point n≥4, except for SF=0.8 and 7 (n=1 for both). The slopes of the linear fits to the data were −1.29±0.05 (left) and −1.34±0.01 (right).

FIGS. 10A-10B are a set of graphs showing the effect of scaling the virtual $I_{Nav1.6}$ on the AIS compartment model activity in response to synaptic stimulation. The external input $I_{Nav1.2}$ (also called ken; see FIGS. 15-36) was set to zero. FIG. 10A shows representative examples of $V_m$ changes, associated $I_{Nav1.6}$ and $I_{Kv}$ traces, elicited at $g_e$:$g_i$=1 or 2, respectively. The effects of reducing control ($g_{Nav1.6}$=1) by 50% or increasing it by 50%, respectively, are shown. FIG. 10B shows input-output relationships as a function of $g_e$:$g_i$ ratios, with $I_{Nav1.6}$ scaled to the indicated values. Data represent mean; for each data point n=2.

FIGS. 11A-11E are a set of graphs showing the contribution of heterologously expressed wild-type $I_{Nav1.2}$ and/or virtual $I_{Nav1.6}$ to AIS compartment model activity. Activity is sensitive to the magnitude of individual Na$_v$1.2 and Na$_v$1.6 conductances. Representative $V_m$ changes (upward deflections, first row), associated wild-type input $I_{Nav1.2}$ (downward deflections, second row), $I_{Nav1.6}$ (downward deflections, third row), and $I_{Kv}$ (upward deflections, fourth row) at $g_e:g_i=1.5$ or 2 are shown. FIG. 11A shows firing activity with $I_{Nav1.6}$ set to zero (control). See also FIGS. 6A-6E for comparison. FIGS. 11B-11C show that introducing virtual $I_{Nav1.6}$ reduced to 10 or 20% of control into the model cell while keeping $I_{Nav1.2}$ unchanged results in a considerably increased activity. FIGS. 11D-11E show typical firing in response with $I_{Nav1.2}$ set to zero and $g_{Nav\ 1.6}$ set to 0.5 or 1. The latter value results in depolarization block at $g_e:g_i=2$ (red arrows). Shaded insets in D show typical $I_{Nav1.6}$ and $I_{Kv}$ traces on expanded time scale.

FIGS. 12A-12B are a set of graphs showing the effect of scaling the wild-type or mutant input $I_{Nav1.2}$ on AIS compartment model activity. FIG. 12A shows representative activities in response to a synaptic stimulation of $g_e:g_i=2$. The input $I_{Nav1.2}$ was reduced (60%) or increased (120%) compared to control (100/0). $V_m$ changes (upward deflections) and associated scaled input $I_{Nav1.2}$ (downward deflections) are shown. Note the overall firing rate-increase with the R1882Q variant. FIG. 12B shows average firing activity in response to synaptic stimulation of $g_e:g_i=2$ or 2.5, with scaled input $I_{Nav1.2}$. Data are presented as mean±SEM; for each data point n≥4.

FIGS. 13A-13B are a set of graphs showing representative action potentials and associated currents in dynamic action potential clamp experiments implementing wild-type (FIG. 13A) or R1882Q $I_{Nav1.2}$ (FIG. 13B). The effect of reducing the input $I_{Nav1.2}$ (60% of control), reducing $I_{Nav1.2}$ (60% of control) and introducing $I_{Nav1.6}$ (20% of control), or increasing Cm (by 50% compared to control). Shaded boxes (left) show typical action potentials and associated $I_{Nav1.2}$ and $I_{Kv}$ traces on expanded time scale. Note the overall higher activity recorded in the AIS model in the presence of R1882Q $I_{Nav1.2}$ compared to R853Q (n 3 for both A and B).

$$I/I_{max} = A_f e^{-t/\tau_f} + A_s e^{-t/\tau_s},$$

where t is time, $A_f$ and $A_s$ are the fractions of the fast and slow inactivation components, whereas $T_f$ and $T_s$ are the time constants of the fast and slow inactivating components, respectively. Note that $I_{Kv}$ traces in grey represent SEM. With wild-type or R1882Q input $I_{Nav1.2}$, the mean±SEM values of $\tau_f$ were 2.1±0.1 or 2.6±0.2 ms, whereas the mean±SEM $\tau_s$ values were 11.9±1.4 or 24.9±5.59 ms, respectively (inset bar graph; *P<0.05, Student's t-test).

Figure 15:
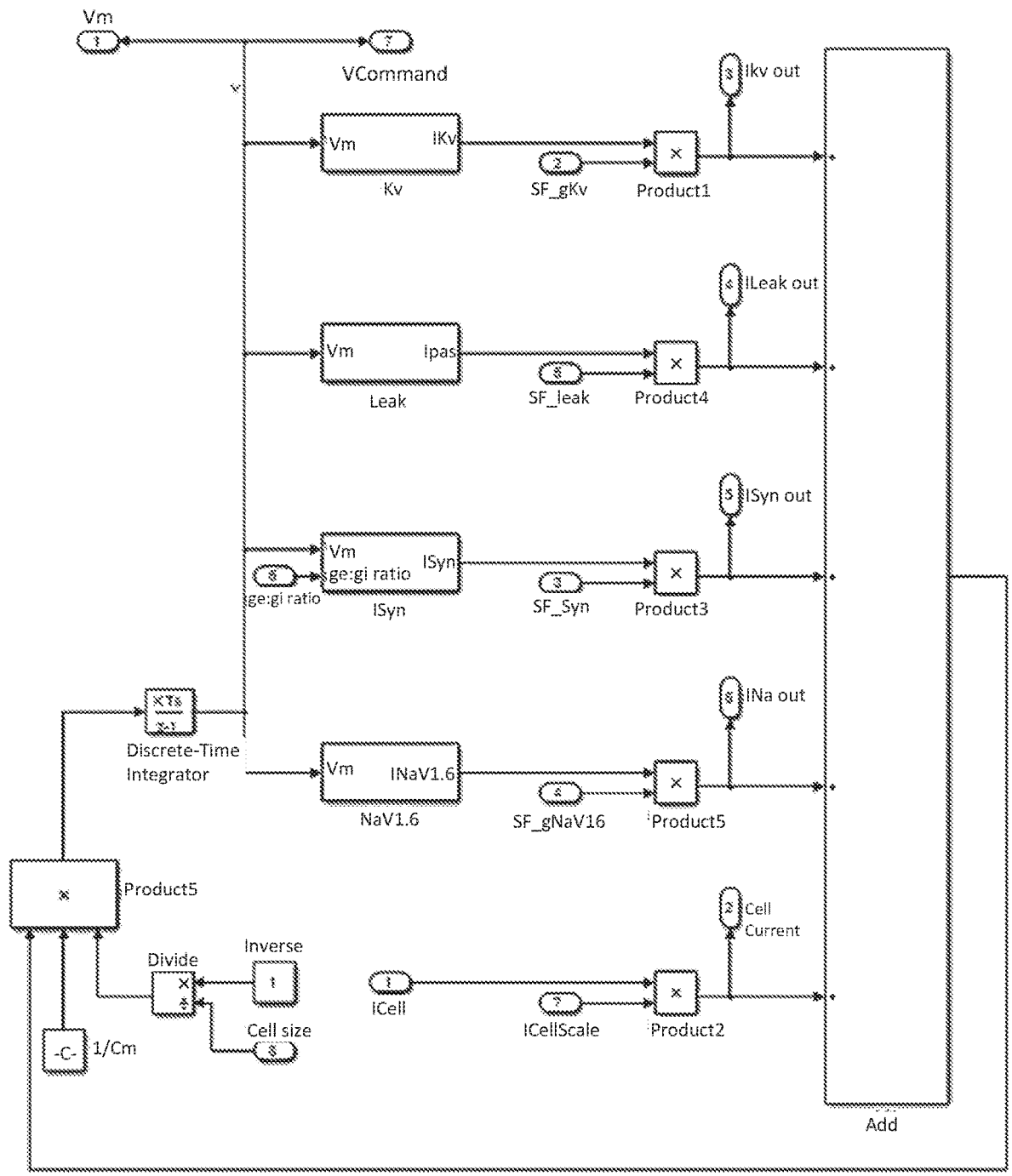

FIG. 15 is a Simulink model of the AIS compartment implementing scalable cell capacitance (Cm) and scalable (SF)currents, including voltage dependent potassium current ($I_{Kv}$), passive leak current ($I_{pas}$), voltage dependent Na$_v$ 1.6 current ($I_{Nav1.6}$), excitatory and inhibitory synaptic currents ($I_{syn}$), and heterologously expressed input Na$_v$ 1.2 current ($I_{cell}$).

Figure 16:
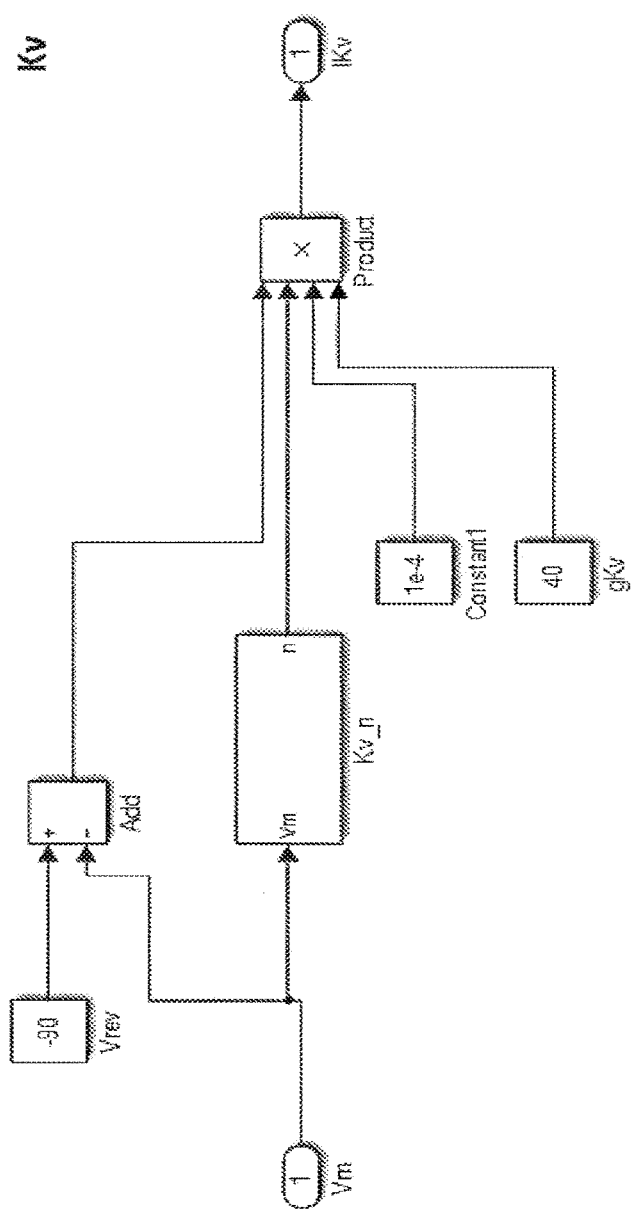

FIG. 16 is a Simulink model of potassium current (Kv)

$$I_{Kv} = gKv = gKv * n(Vm-(-90)),$$

where gKv=40 pS$\mu$m$^{-2}$ is the potassium conductance and n is the activation gate.

Figure 17:
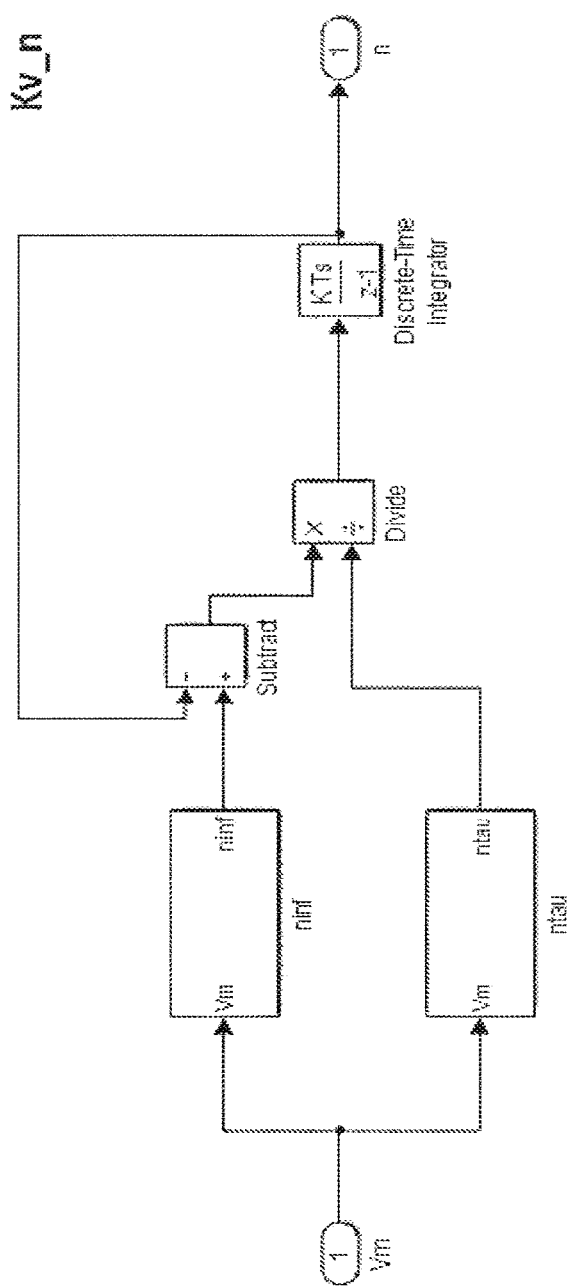

FIG. 17 is a Simulink model of potassium channel activation gate (Kv_n)

$$\frac{dn}{dt} = \frac{n_{inf} - n}{n_{tau}}$$

where $n_{inf}$, $n_{tau}$ are the steady-state activation variable and time constant of activation, respectively.

Figure 18:
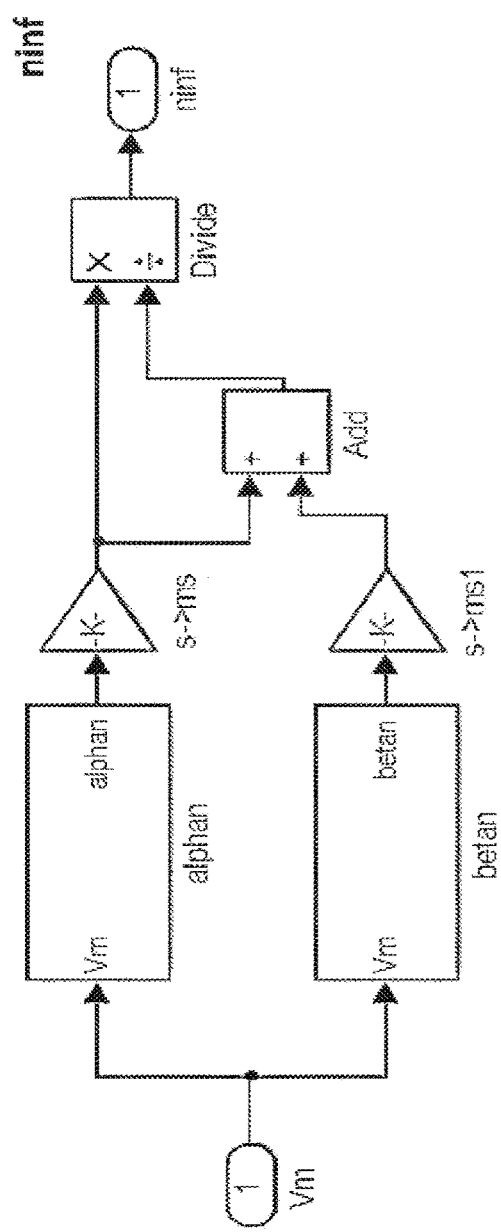

FIG. 18 is a Simulink model of steady state activation of potassium ion channel (ninf)

$$ninf = \frac{\text{alpha}n}{\text{alpha}n + \text{beta}n}$$

where alphan and betan are rate constants of potassium activation.

Figure 19:
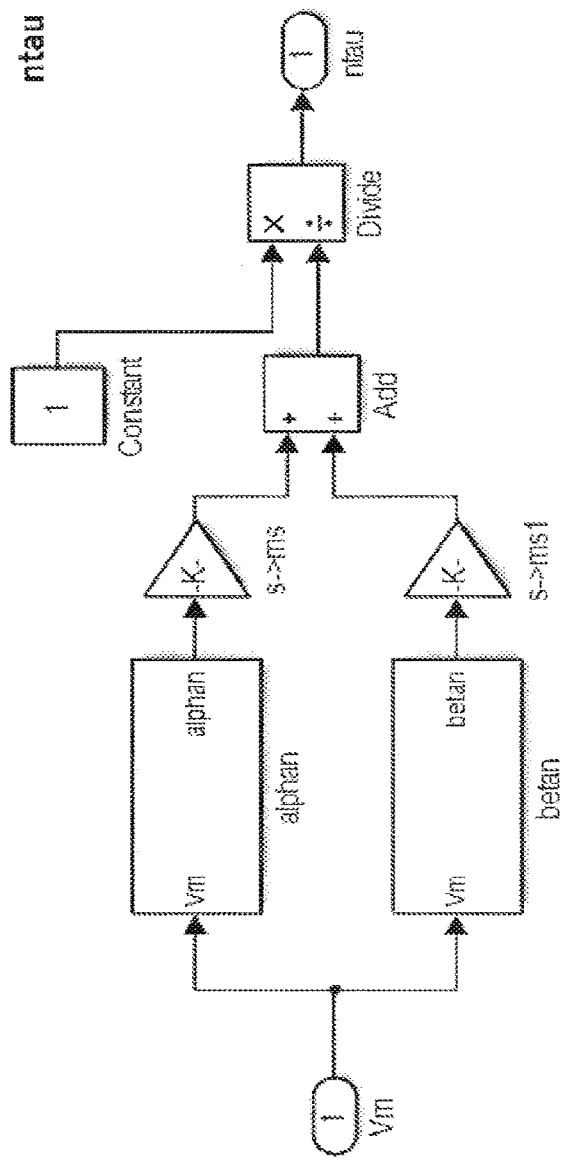

FIG. 19 is a Simulink model of activation time constant of potassium ion channel (ntau).

$$ntau = \frac{1}{\text{alpha}n + \text{beta}n}$$

Figure 20:
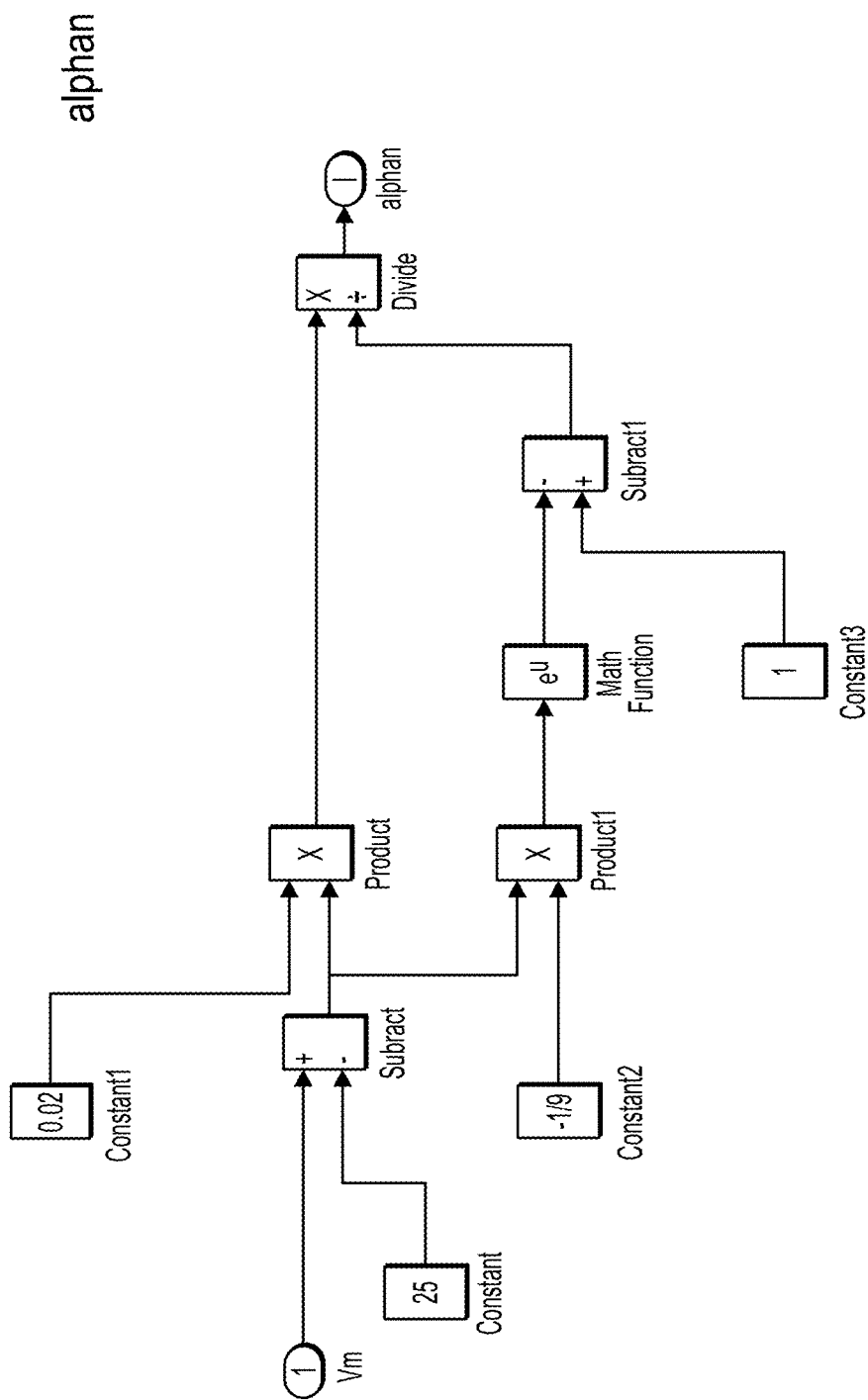

FIG. 20 is a Simulink model of Rate constant (alphan).

$$\text{alpha}n = \frac{0.02(Vm - 25)}{1 - \exp\left(-\frac{Vm - 25}{9}\right)}$$

Figure 21:
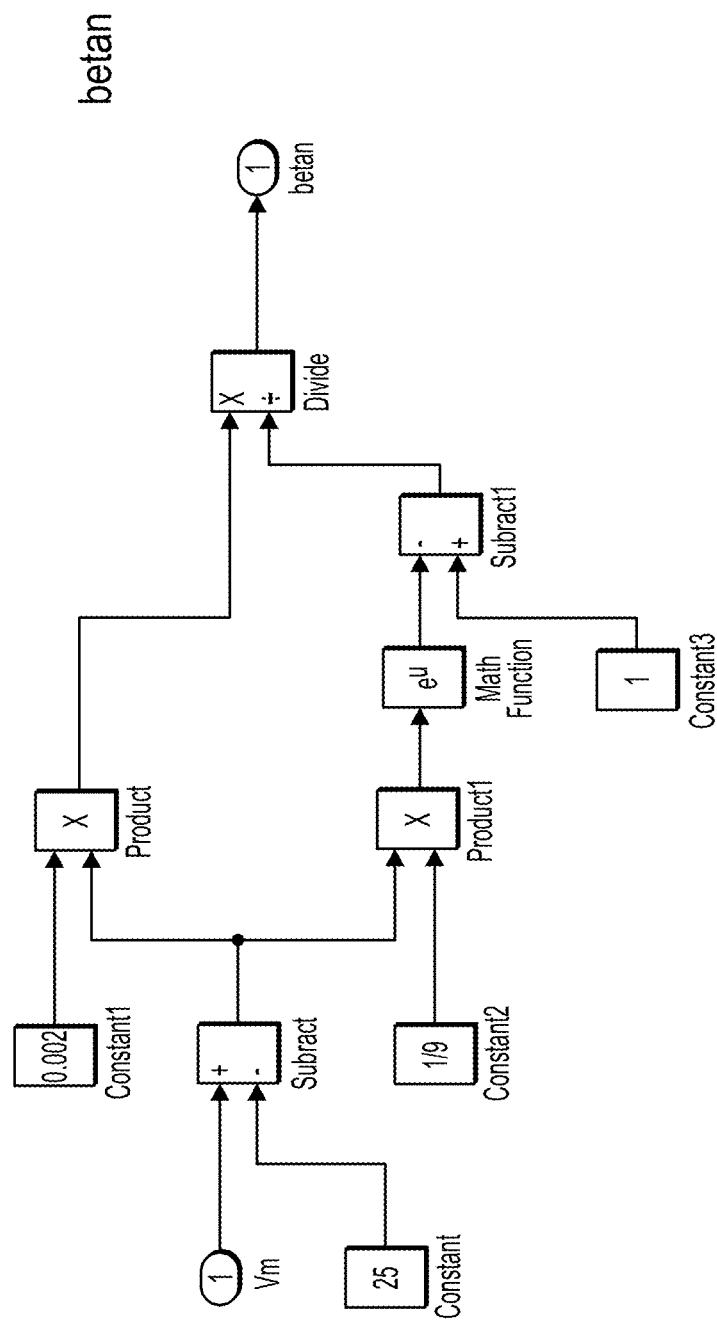

FIG. 21 is a Simulink model of rate constant (betan).

$$\text{beta}n = \frac{-0.002(Vm - 25)}{1 - \exp\left(\frac{Vm - 25}{9}\right)}$$

Figure 22:
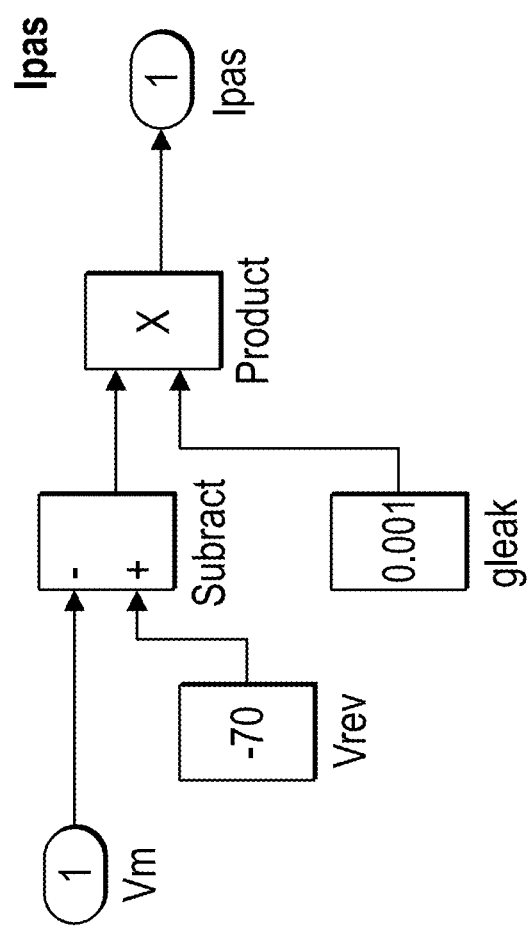

FIG. 22 is a Simulink model of leak current (Ipas).

$$Ipas = 0.001 * (Vm-(-70))$$

Figure 23:
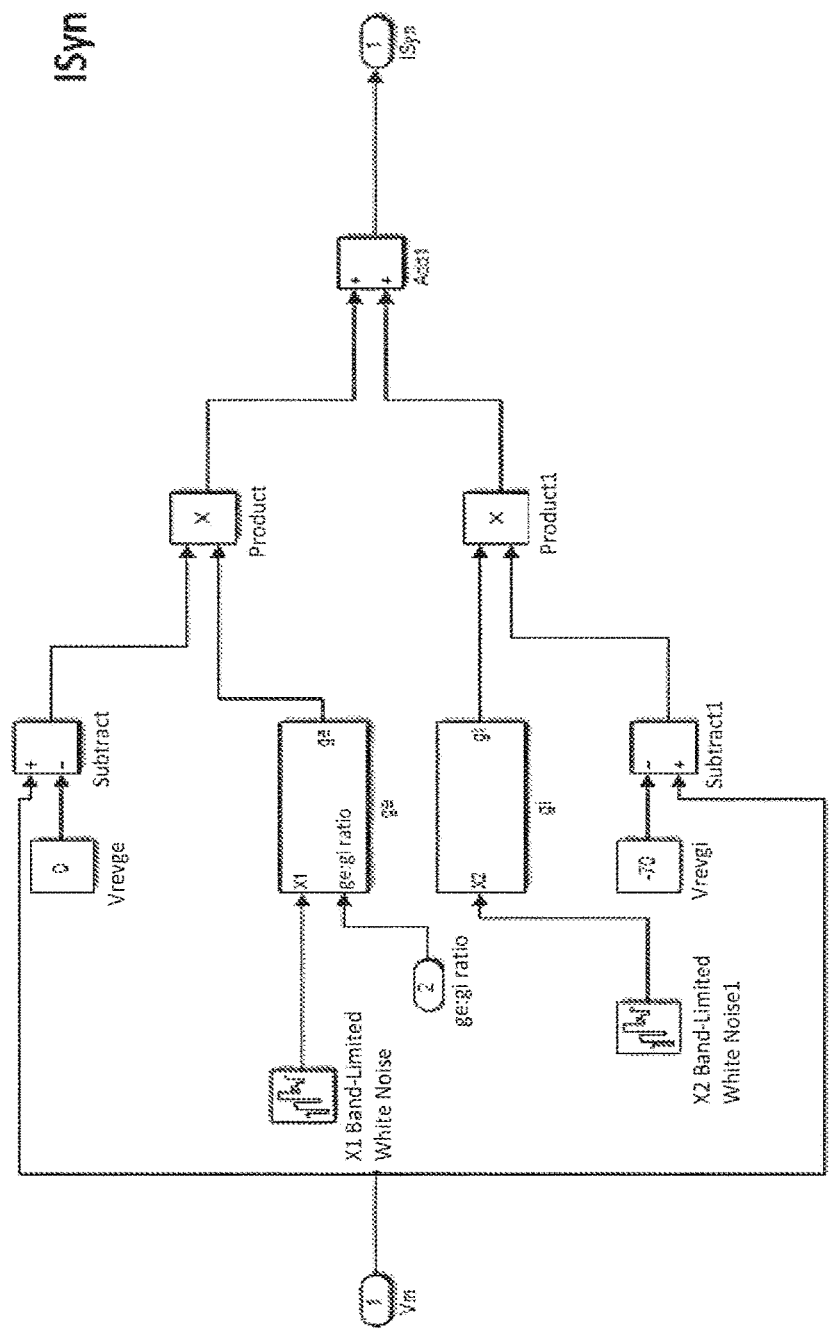

FIG. 23 is a Simulink model of synaptic current (ISyn).

$$ISyn = ge(Vm-0) + gi(Vm-(-70)),$$

where ge, gi are excitatory and inhibitory synaptic conductances, respectively.

Figure 24:
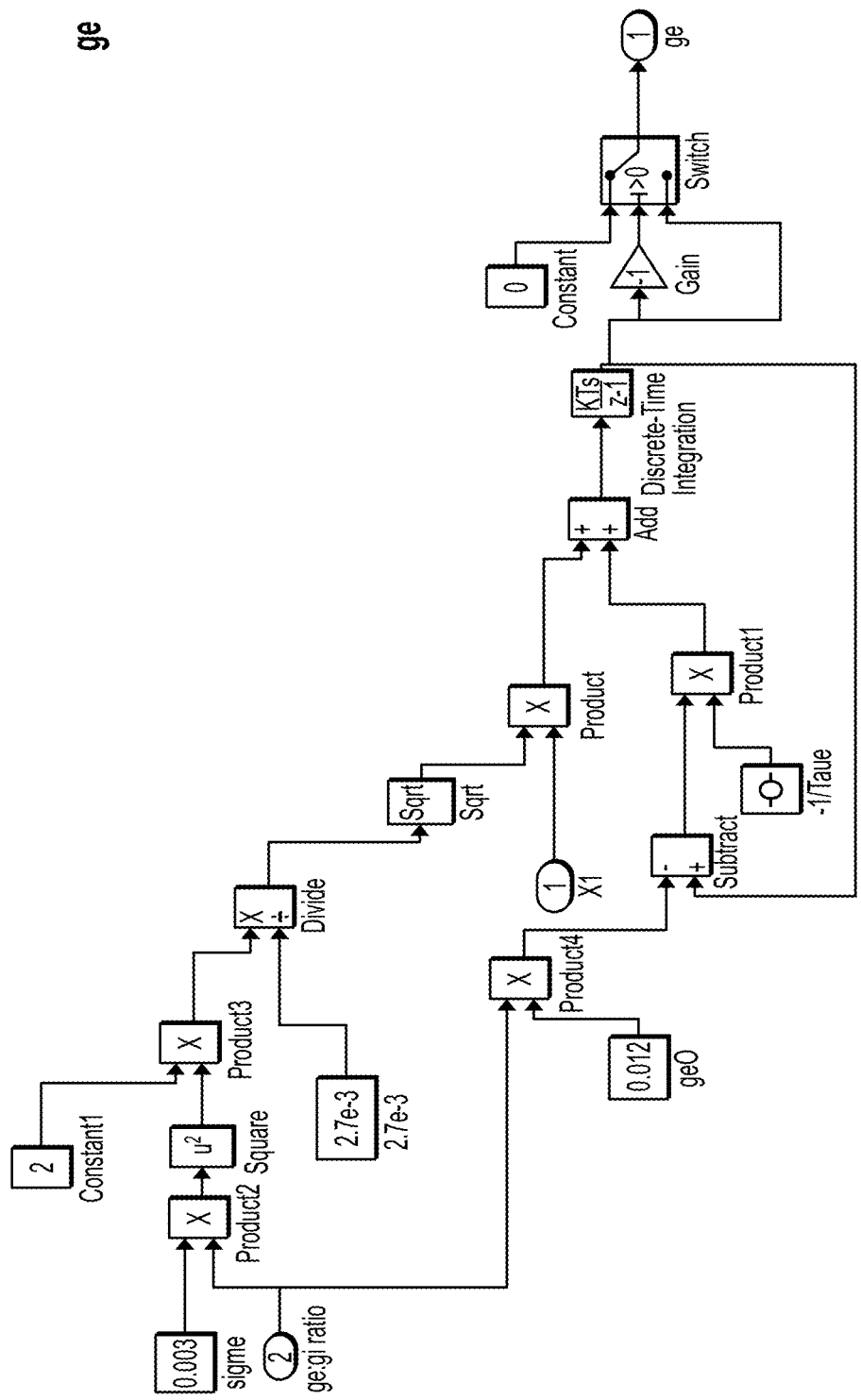

FIG. 24 is a Simulink model of excitatory conductance (ge)

$$\frac{dge}{dt} = -\frac{1}{taue}[ge - ge_0] + \sqrt{D_e} \, x1$$

$$D_e = 2 * \frac{sigmae^2}{taue}$$

where taue=2.7 ms, ge0=0.012 μS, sigmae=0.003ΞS, $D_e$ is the time constant, average standard deviation, and amplitude of the excitatory conductance, respectively, and $x_1$ is Gaussian white noise of zero mean and unit standard deviation.

Figure 25:
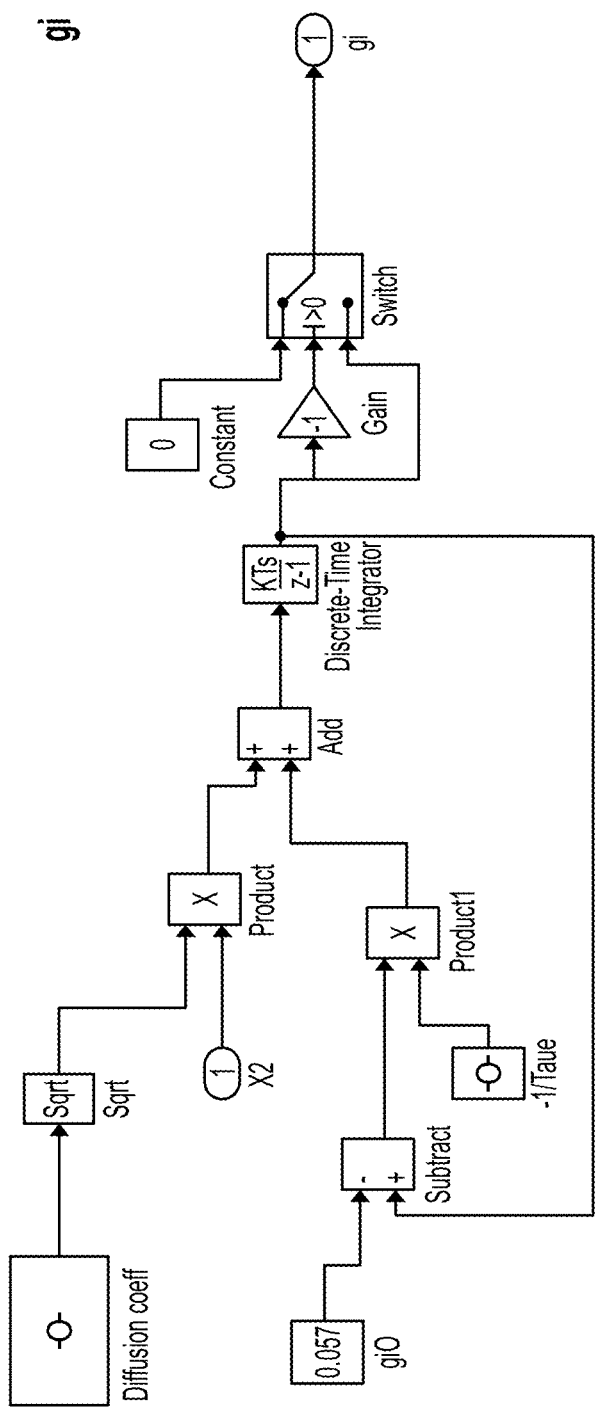

FIG. 25 is a Simulink model of inhibitory conductance (gi)

$$\frac{dgi}{dt} = -\frac{1}{taui}[gi - gi_0] + \sqrt{D_i}\, x_2$$

$$D_i = 2 * \frac{sigmai^2}{taui}$$

where taui=10.5 ms, gi0=0.057 µS, sigmai=0.0066 µS, $D_i$ is the time constant, average standard deviation, and amplitude of the inhibitory conductance, respectively, and $x_2$ is Gaussian white noise of zero mean and unit standard deviation.

Figure 26:
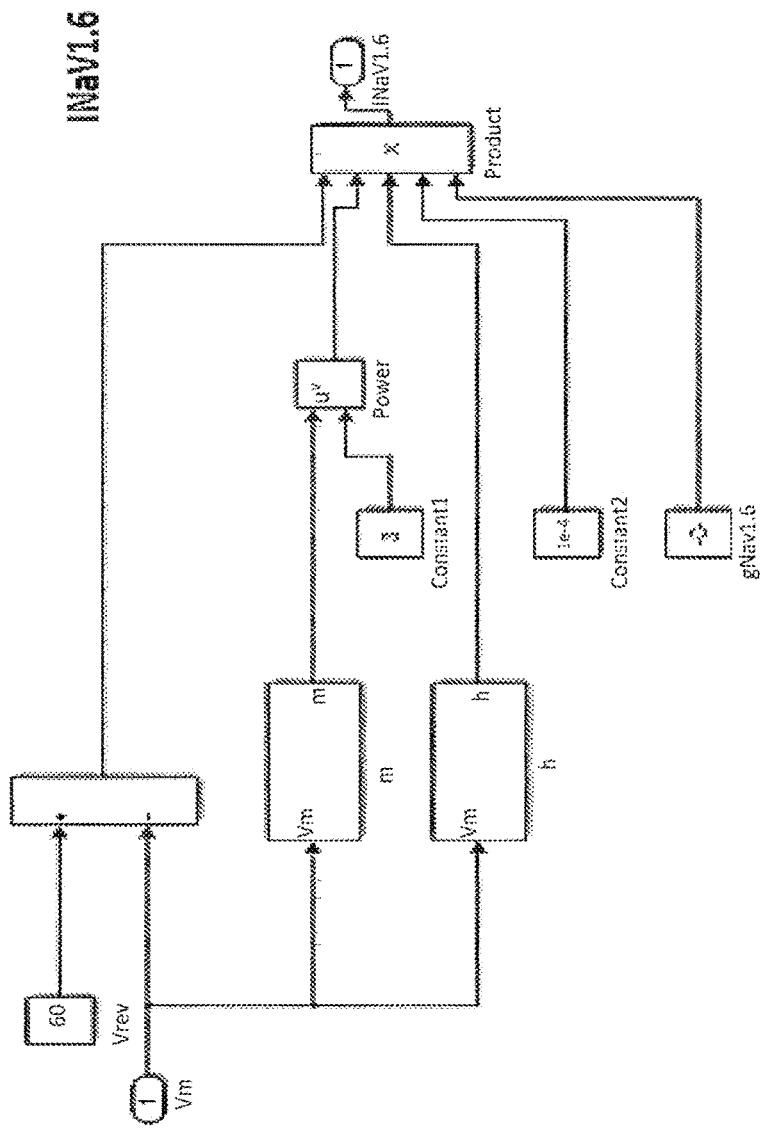

FIG. 26 is a Simulink model of sodium (Na$_v$ 1.6) current (INaV1.6).vv $$INaV1.6 = g_{Nav\,1.6} * m^3 h(Vm-(-60))$$

where $g_{Nav\,1.6} = 1097.1$ pSµm$^{-2}$ is the sodium conductance, m, h are activation and inactivation gates, respectively.

Figure 27:
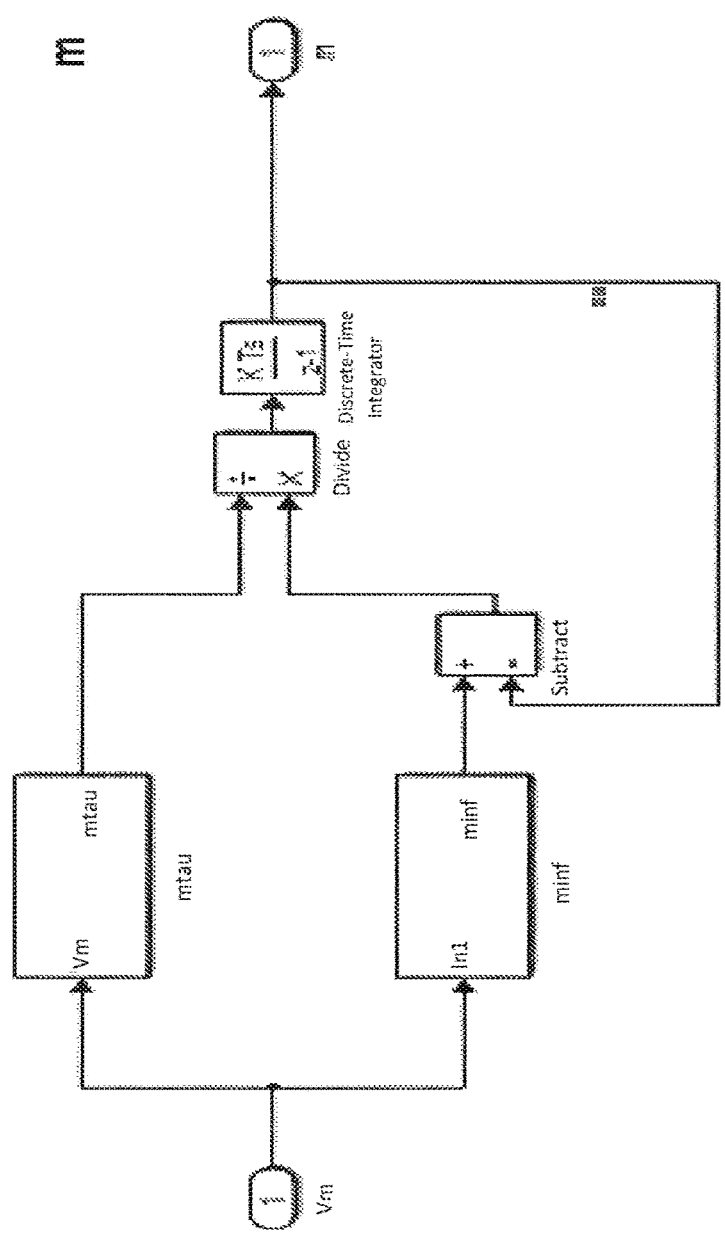

FIG. 27 is a Simulink model of sodium activation gate (m).

$$\frac{dm}{dt} = \frac{m_{inf} - m}{m_{tau}}$$

where $m_{inf}$, $m_{tau}$ are the steady state activation and activation time constants, respectively.

Figure 28:
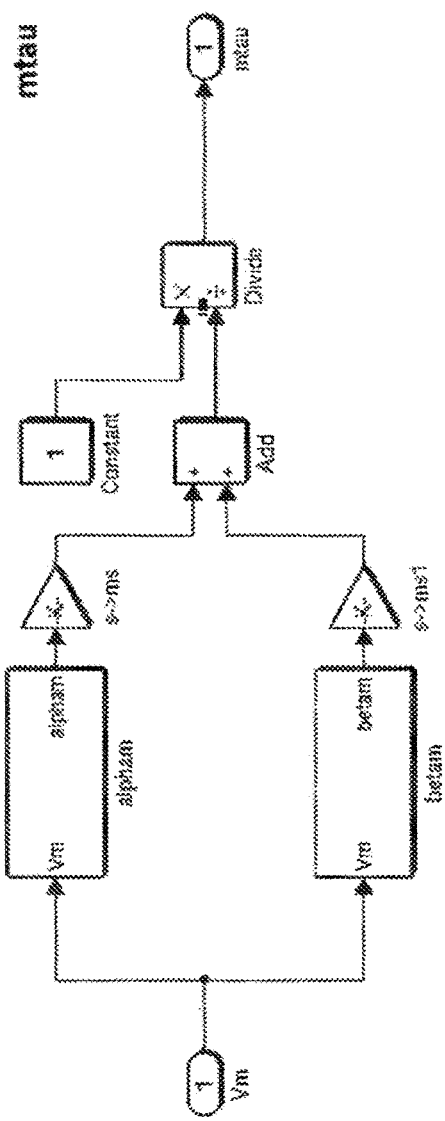

FIG. 28 is a Simulink model of activation time constant of sodium ion channel (mtau).

$$mtau = \frac{1}{\text{alpha}m + \text{beta}m}$$

where alpham and betam are rate constants, respectively.

Figure 29:
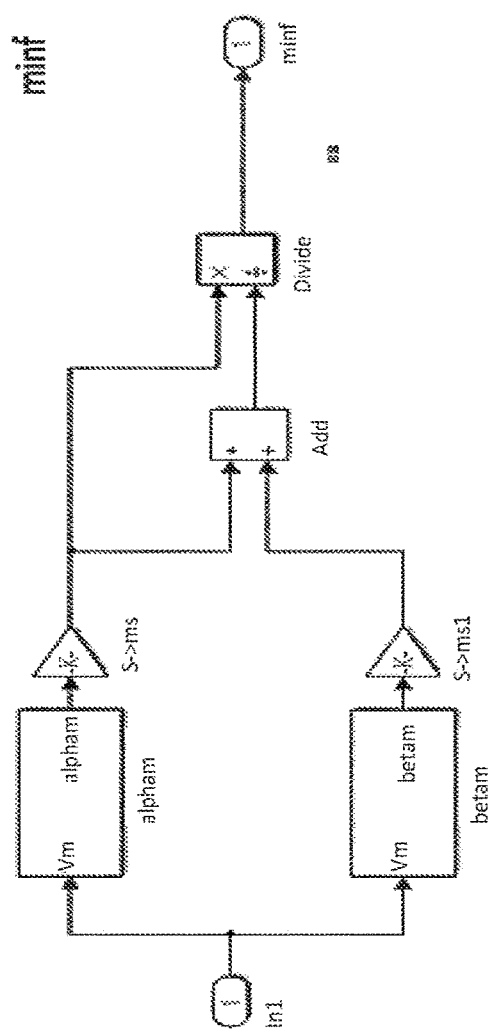

FIG. 29 is a Simulink model of steady-state activation of sodium ion channel (minf).

$$minf = \frac{\text{alpha}m}{\text{alpha}m + \text{beta}m}$$

Figure 30:
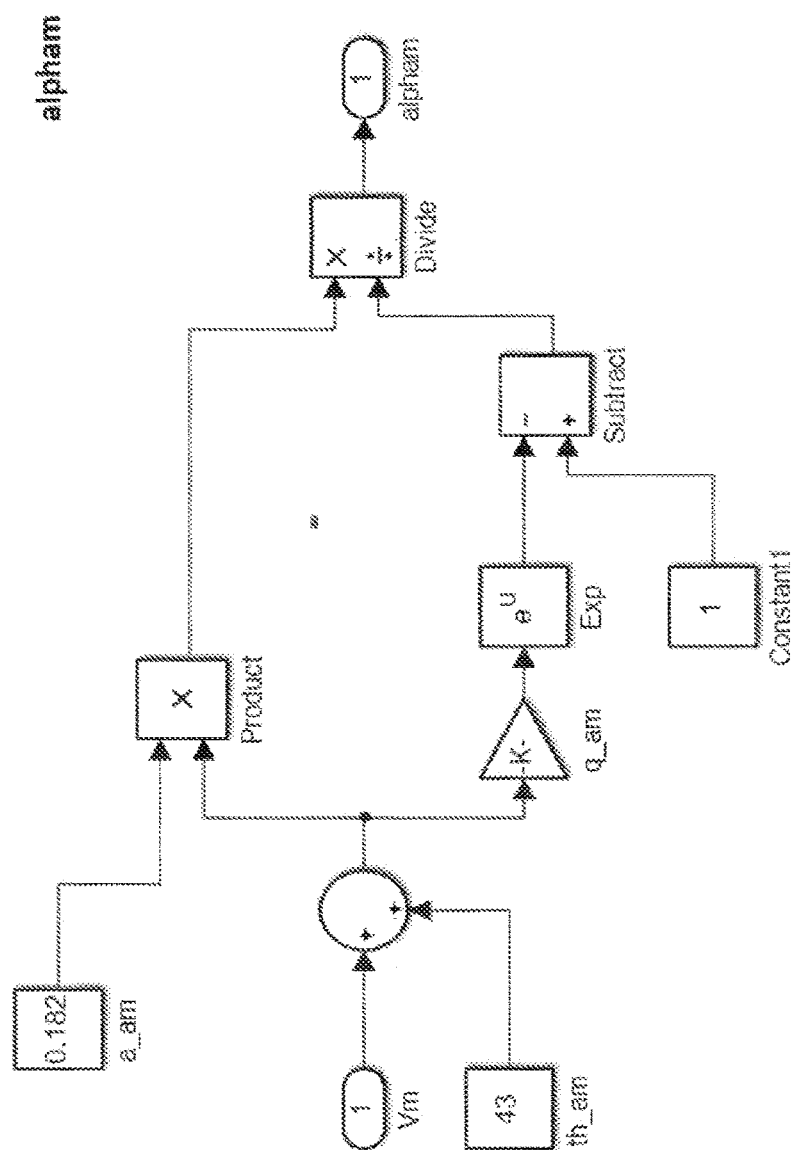

FIG. 30 is a Simulink model of rate constant (alpham).

$$\text{alpha}m = \frac{0.182(Vm + 43)}{1 - \exp\left(-\frac{Vm + 43}{6}\right)}$$

Figure 31:
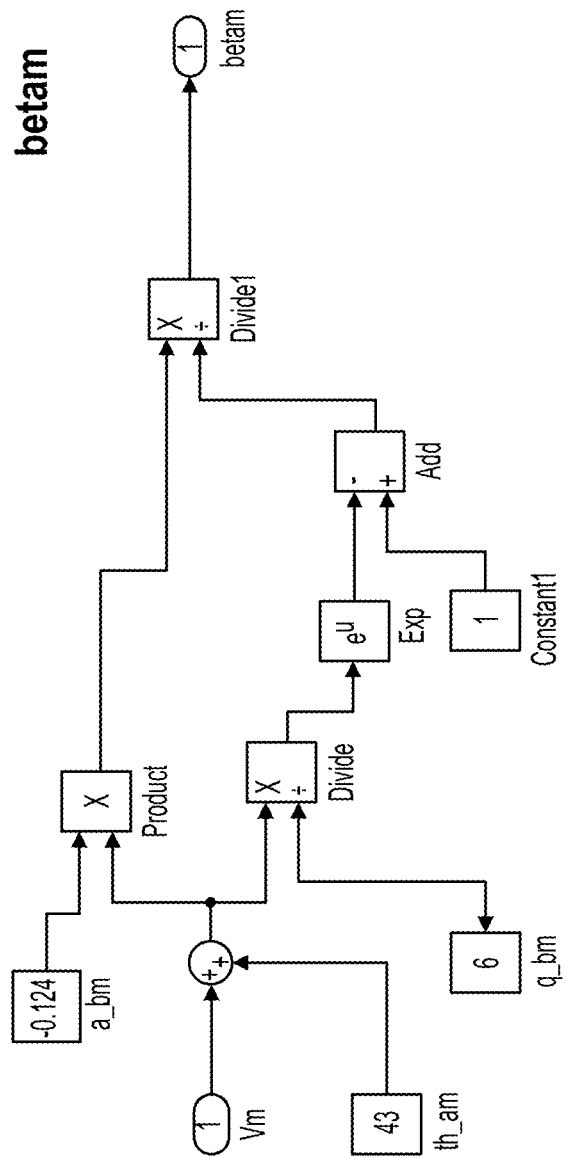

FIG. 31 is a Simulink model of rate constant (betam).

$$\text{beta}m = \frac{-0.124(Vm + 43)}{1 - \exp\left(\frac{Vm + 43}{6}\right)}$$

Figure 32:
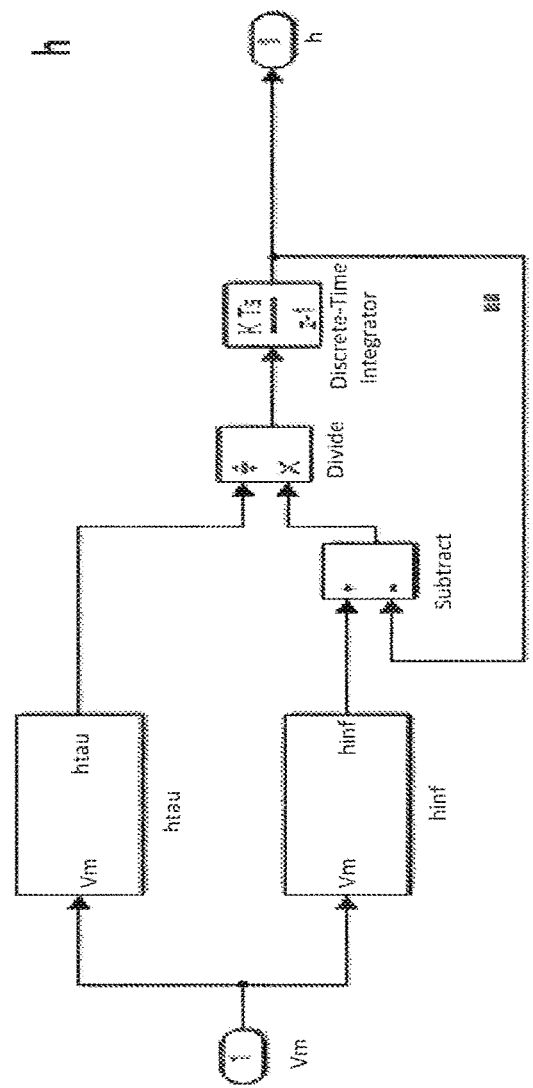

FIG. 32 is a Simulink model of sodium channel inactivation gate (h)

$$\frac{dh}{dt} = \frac{h_{inf} - h}{h_{tau}}$$

where $h_{inf}$, $h_{tau}$ are the steady state inactivation and inactivation time constants, respectively.

Figure 33:
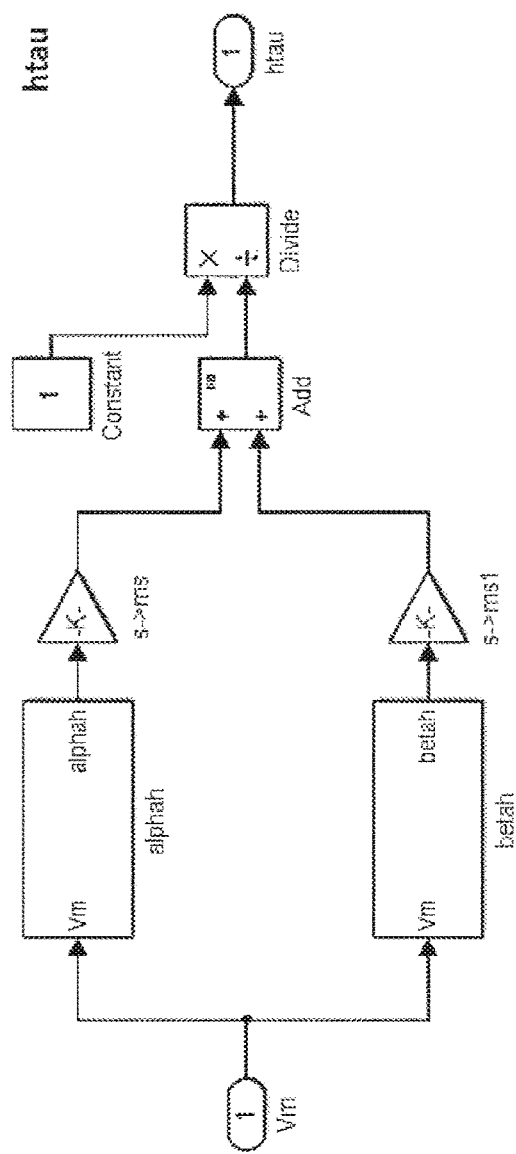

FIG. 33 is a Simulink model of sodium channel inactivation time constant (htau)

$$htau = \frac{1}{\text{alpha}h + \text{beta}h}$$

where alphah and betah are rate constants of inactivation, respectively.

Figure 34:
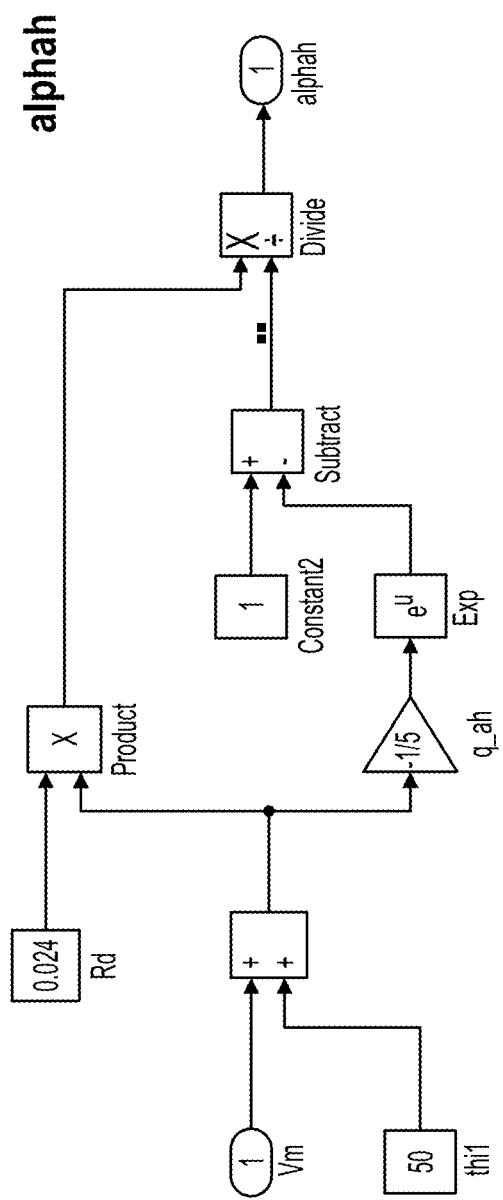

FIG. 34 is a Simulink model of rate constant (alphah).

$$\text{alpha}h = \frac{0.024(Vm + 50)}{1 - \exp\left(-\frac{Vm + 50}{5}\right)}$$

Figure 35:
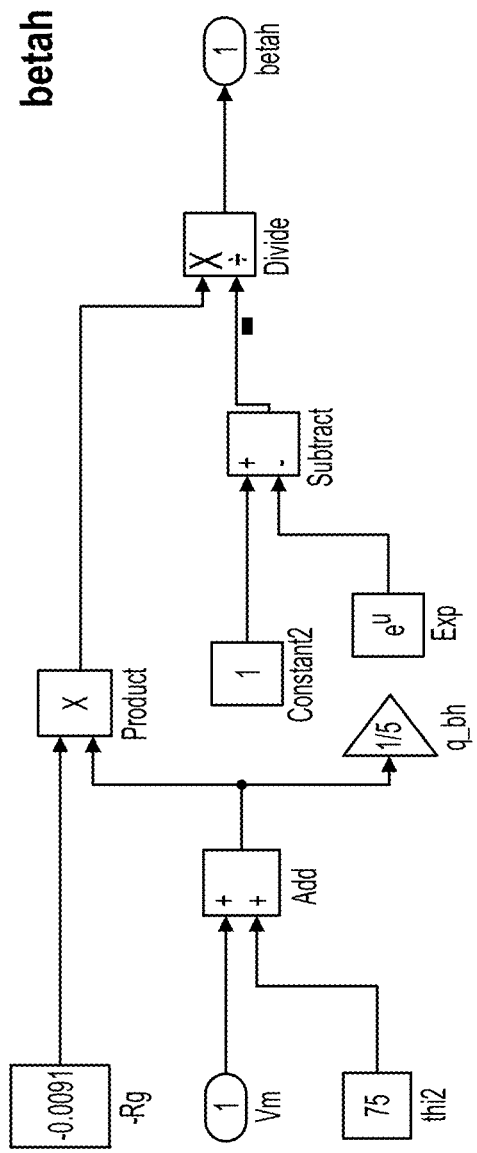

FIG. 35 is a Simulink model of rate constant (betah).

$$\text{beta}h = \frac{-0.0091(Vm + 75)}{1 - \exp\left(\frac{Vm + 75}{5}\right)}$$

Figure 36:
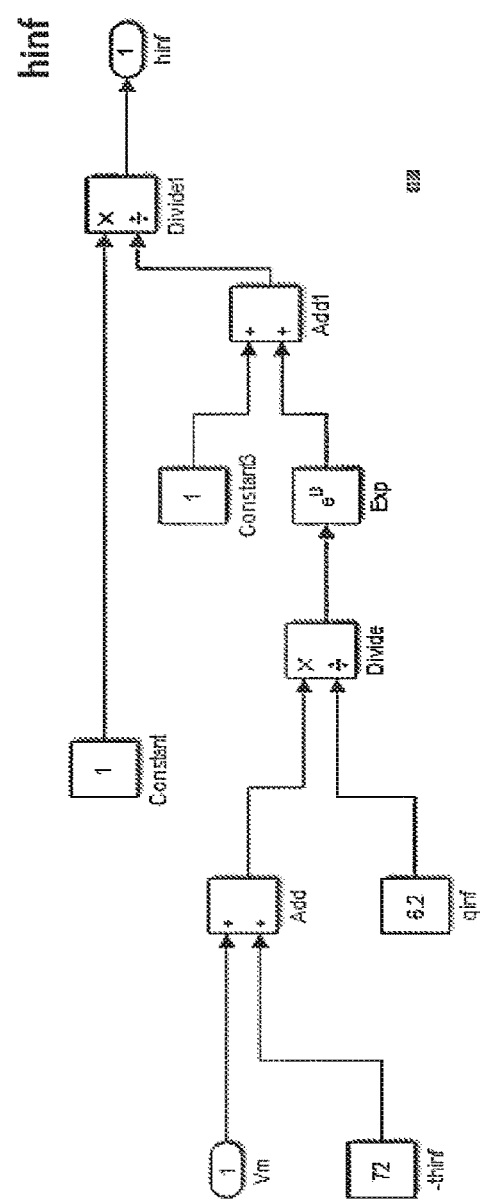

FIG. 36 is a Simulink model of sodium channel steady-state inactivation (hinf).

$$hinf = \frac{1}{1 + \exp\left(\frac{Vm + 72}{6.2}\right)}$$

DETAILED DESCRIPTION

The present invention features methods for identifying gain-of-function (GOF) and loss-of-function (LOF) mutations in membrane proteins, such as ion channels and receptors, by using a dynamic voltage clamp. The invention also features methods of determining whether a mutation is a GOF or LOF mutation and treating a disease or disorder associated with the particular GOF or LOF mutation. The dynamic clamps described herein can be used to predict phenotypic consequences and assist in the treatment of mutationally associated diseases by coupling biophysical, neurophysiological, and clinical impacts of ion channel and receptor mutations.

Dynamic Clamp

The voltage clamp is an experimental electrophysiology method used to measure ion currents through membranes of excitable cells (e.g., neurons), while holding the membrane voltage at a constant level. A voltage clamp will iteratively measure the membrane potential and then change the membrane potential (voltage) to a desired value by adding the necessary current. This clamps the cell membrane at a desired constant voltage, allowing the voltage clamp to record the currents delivered. Because the currents applied to the cell must be equal to and opposite in charge to the current going across the cell membrane at the set voltage, the recorded currents indicate how the cell reacts to changes in membrane potential. Cell membranes of excitable cells contain many different kinds of ion channels (e.g., voltage gated, ligand gated, or mechanosensitive). The voltage clamp allows the membrane voltage to be manipulated independently of the ionic currents, allowing the current-voltage relationships of membrane channels to be studied.

A dynamic clamp is a type of voltage clamp that detects an electrophysiological parameter (e.g., current, voltage or capacitance) of a biological cell, and then applies a signal (e.g., voltage or current) to the biological cell or a portion thereof to achieve a desired effect on the electrophysiological parameter. The step of applying the signal to the biological cell requires the calculation of the amount of, for example, the voltage or current that must be applied to the cell or portion thereof to produce the desired effect. Following the detection of an electrophysiological parameter and the subsequent application of the signal to the biological cell or portion thereof, the dynamic clamp continually repeats the process. Dynamic clamps and methods of use thereof are described, for example, in PCT Publication No. WO 2010/060151, the disclosure of which is hereby incorporated in its entirety. A dynamic clamp is provided in electrical contact with a biological cell having either a WT or mutant form of the protein of interest (e.g., ion channel or receptor). In assaying whether a mutation is a GOF or LOF mutation, the dynamic clamp assists in providing a waveform at the biological cell or portion thereof.

It is only necessary for one of the ion channels or receptor types to be present in the biological cell or portion thereof. The function of the remaining ion channels or receptor types that are required to provide a waveform may be simulated using a dynamic clamp, which is configured to provide a real time feedback loop with the ion channels or receptor types that are present. The dynamic clamp uses the membrane voltage measured from an electrically excitable cell to solve computational ion channel models running in real time. These models may include differential equations and ionic current calculations driven in part by the measured voltage. The current calculated from these simulations is then injected into the cell in a feedback configuration to create ionic currents that can simulate intrinsic ionic currents within single cells, as well as synaptic currents among cells to create small networks of cells. The signal is used to represent the electrophysiological changes to the cell that would be induced by the remaining ion channels. This allows the effects of the mutation of one type of ion channel or receptor to be detected, while also observing the effect of the mutation on a more complex system. This may be particularly important as the effect of a mutation on an ion channel or receptor involved in producing a waveform may affect parameters such as the frequency of waveform generation, and the morphology of the waveform generated. For example, the morphology of an action potential includes the half width, rise time, decay time, time between successive action potentials and rebound voltage. The methods described herein may include measuring one or more of these parameters.

The methods described herein provide a phenotypic screen that provides rapid high content information on waveform properties of mutant ion channels and receptors (e.g. GOF or LOF mutants). The dynamic clamp may apply a voltage signal to the biological cell or portion thereof, and modulation of the waveform at the biological cell or portion thereof is detected by measuring a current signal at the biological cell or portion thereof. In this embodiment the voltage is clamped. To simulate a particular voltage, the dynamic clamp may measure the membrane current of a biological cell or portion thereof, and use this parameter to determine the amount of voltage to be applied to the cell or portion thereof. If there is insufficient current to produce a waveform, then the dynamic clamp may modulate the amount of current applied by mathematical scaling in the feedback system.

In another embodiment, the dynamic clamp applies a current signal to the biological cell or portion thereof, and modulation of the waveform at the biological cell or portion thereof is detected by measuring a voltage signal at the biological cell or portion thereof. In this embodiment the current is clamped. To simulate a particular conductance, the dynamic clamp may use the measured membrane potential of a biological cell or portion thereof and the reversal potential for that conductance (the membrane potential at which there is no net flow of ions from one side of the membrane to the other) to determine the amount of current to be applied to the cell or portion thereof.

If there is insufficient current to produce a waveform, then a capacitive current term may be used to control the apparent capacitance of the cell or portion thereof and in this way provide a precise control on the ratio of conductance to capacitance. The capacitive current term is calculated by measuring the rate of change of the voltage, and its application may decrease the apparent capacitance of the biological cell or portion thereof to compensate for the lack of current.

The dynamic clamp may also be used to account for leak conductance at the cell or portion thereof. Leak conductance may occur because ion channels or receptors in the cell or portion thereof are open, allowing the passage of ions. If the dynamic clamp does not account for leak conductance, then the assay results may be affected.

The dynamic clamp may also be used to account for and subtract the signal arising from one type of ion channels or receptors involved in the production of a waveform at the biological cell or portion thereof. For example, the signal arising from one type of ion channels or receptor can be removed using a dynamic clamp to provide further information on the effect of that ion channel or receptor on the waveform. Such techniques are known to a person skilled in the art and are discussed, for example, in Prinz et al. *Trends Neurosci.*, 27:218-224, 2004.

Many types of dynamic clamp may be used in the method according to the present invention. The dynamic clamp may include, for example, one or more electrodes and a simulator. The simulator may include an amplifier and computational software, which may be stored on and executed by a computing system.

Electrodes

In one embodiment, the one or more electrodes in contact with the biological cell or portion thereof are sharp electrodes. A sharp electrode is a type of micropipette that has a very fine pore that allows slow movement (generally only capillary action) of solution through the electrode, thereby providing a minimal effect on the composition of the intracellular fluid. In use, a sharp electrode punctures the cell membrane so that the tip of the electrode is inside the cell.

In another embodiment, the one or more electrodes in contact with the biological cell or portion thereof are patch electrodes. A patch electrode includes a much larger pore than a sharp electrode. For a patch electrode, a high resistance (typically hundreds of megaohms to several gigaohms) electrical seal is formed between the electrode and the membrane of a biological cell. The membrane of the biological cell is then ruptured (such as by suction) so that a solution in a pipette (for pipette patch electrodes) or adjoining the aperture (for a planar patch electrode) is able to mix with the intracellular fluid. This is also known as a whole cell patch and allows an electrophysiological parameter across an entire cell membrane to be measured.

In one embodiment, a pipette patch electrode involves the formation of a high resistance electrical seal between a micropipette (e.g., the electrode) and a membrane of the biological cell. Once the seal is formed, a solution in the micropipette is able to mix with the intracellular fluid. In contrast, a planar patch electrode may involve the formation of a high resistance electrical seal between an aperture of a usually flat substrate (e.g., the electrode) and a membrane of the biological cell. In general, a well is provided at each aperture of the substrate, and after a seal is formed and the membrane ruptured, a solution in this well is able to mix with the intracellular fluid. As the planar electrode may include multiple apertures at which high resistance electrical seals may be formed with different cells, planar patch electrodes are generally more adaptable to high throughput, automated screening techniques. For example, electrodes which accommodate 16, 48, 96 or 384 cells for simultaneous recordings may be employed. Such electrodes include, for example, QPlate (Sophion Bioscience), Patch Plate PPC, Patch Plate substrates (MDS Analytical Technologies) or those used for the Patchliner and Synchropatch systems (Nanion Technologies GmbH) or the IonFlux system (Fluxion Biosciences). Regardless of the type of patch electrode, it is important to achieve a high resistance electrical seal between the electrode and the membrane of the biological cell or portion thereof.

Many of the types of electrodes discussed above require the use of a solution which is in contact with the intracellular fluid of the cell. The composition of the solution used with the electrode depends on the assay to be conducted, and a person skilled in the art would be able to select a suitable solution without undue experimentation. If the solution is to be able to mix with the intracellular fluid, the solution generally includes a high concentration of electrolytes and is iso-osmotic to the intracellular fluid. When conducting assays with patch electrodes, this solution may be changed or altered.

The dynamic clamp may include one or more electrodes. In one embodiment, the dynamic clamp includes two electrodes which are in contact with a biological cell or portion thereof. In another embodiment, the dynamic clamp includes one electrode which is in contact with a biological cell or portion thereof. These electrodes may provide a continuous clamp, a discontinuous clamp or a two electrode clamp. A continuous clamp includes one electrode, and that electrode simultaneously and continuously detects an electrophysiological parameter and applies the signal (such as the voltage or current) to a cell or portion thereof. In contrast, a discontinuous clamp also includes one electrode, but that electrode switches between detecting an electrophysiological parameter and applying the signal to the cell or portion thereof. In a two electrode clamp there are two electrodes: one electrode detects an electrophysiological parameter and the other applies the signal to the cell or portion thereof.

The dynamic clamp may also include a ground electrode. A ground electrode sets the ground reference point for electrophysiological measurements. The ground electrode may be in contact with a bath solution surrounding the biological cell or portion thereof. In one embodiment the ground electrode is a silver chloride coated silver wire. In another embodiment the ground electrode is a platinum electrode. The ground electrode may also be coated with agar.

Other current and voltage clamp systems that may be adapted for use in the method according to the present invention are described, for example, in The Axon Guide: A Guide to Electrophysiology and Biophysics Laboratory Techniques, MDS Analytical Technologies, 2008.

Simulator

In addition to the one or more electrodes, the dynamic clamp may also include a simulator to simulate the function of one or more ion channels or receptor types for providing a waveform that are present or absent in the biological cell or portion thereof. The simulator is configured to receive a first signal from the electrode, which is based on the detected modulation of the ion channel or receptor, and to provide a second signal to the electrode to be applied to the cell or portion thereof. The signal provided to the cell simulates the function of one or more of the ion channel or receptor types based on the first signal, to thereby provide the waveform at the biological cell or portion thereof.

The simulator may also include an output to display at least one of a waveform or other data to determine how a mutation modulates an ion channel or receptor. In this embodiment, the other data displayed by the software may include, for example, the raw data obtained from the assay, or an icon or symbol that indicates whether or not there has been any change in the output produced by the mutant compared to the WT form.

Amplifier

The simulator may include one or more amplifiers. The simulator may also include a suitably programmed computing system. The computing system may operate to control the amplifier to provide the second signal to the one or more electrodes, and the computing system operates to receive the first signal from the one or more electrodes. The computing system may also operate to analyze the first signal and control the amplifier in accordance with analysis of the first signal. Many amplifiers may be used to assist in the measurement of an electrophysiological parameter at the biological cell or portion thereof and also to assist in the control of the signal applied to that cell or portion thereof. In some instances, separate amplifiers may be used to perform these two functions.

The type or characteristics (for example input impedance or bandwidth) of the amplifier required will vary depending upon a number of factors including, but not limited to, the type of electrode used (e.g., sharp electrode or patch electrode) and if the electrodes provide a continuous clamp, a discontinuous clamp, or a two electrode clamp. The amplifier may also provide features such as series resistance compensation, capacitance compensation, low-pass filters, Bridge Balance and features to assist in record keeping, cell penetration, and patch rupture. The amplifier may also include a feedback amplification system to further control the current when using a patch clamp in current clamp mode (a patch clamp in voltage clamp mode does not require such a feedback amplification system).

For example, when performing patch electrode assays, suitable amplifiers may include the EPCIO (HEKA Elektronik), the Axopatch 200B (Molecular Devices), the VE-2 (Alembic Instruments Inc.) and the MultiClamp 700A (Molecular Devices). When performing sharp electrode experiments, the Axoclamp 2B (Molecular Devices) may be a suitable amplifier.

Computing System and Simulation

The dynamic clamp may also include computational software, which may be stored on a computing system or other similar processing device. The computing system is typically adapted to receive signals indicative of electrophysiological parameters, perform processing of the parameters and control the signal application to the cell. Accordingly, any suitable form of computing system can be used. The computing system may include, for example, a processor, a memory, an input/output device (e.g., keyboard or display), and an external interface, coupled together via a bus. When in use, the external interface may be coupled to a remote store, such as a database, as well as to the amplifier.

In use, the processor executes software stored in the memory. The software defines instructions, typically in the form of commands, which cause the processor to perform the steps outlined above, and described in more detail below, to control the dynamic clamp while performing the assay. The software may also display results to allow the outcome of the assay to be determined. Accordingly, the computing system may be type of processing system, such as a computer server, a network server, a web server, a desktop computer, or a lap-top. Alternative specialized hardware may be used, such as FPGA (field programmable gate array). The computing system may be used to detect modulation of the waveform at the biological cell or portion thereof (which is indicative of a mutation that modulates at least one type of functional ion channel or receptor in the cell or portion thereof).

The computing system may also be used to determine the signal that should be provided to the biological cell or portion thereof to simulate the function of one or more ion channel or receptor types in the biological cell or portion thereof. The amount of voltage or current to be provided to the cell or portion thereof is determined based on modulation of the ion channels or receptors that are functional in the biological cell, as measured by electrophysiological measurements of that cell or portion thereof. This assists in understanding the effect that modulation of a type of functional ion channel or receptor in a biological cell or portion thereof by a mutation will have on the waveform.

The simulated signal is generated by modeling data representative of ion channels or receptors, which modeling may occur in software. The data for the model can be either collected by recording the action of those types of ion channels or receptors or by input of known data. As the data are representative of the conductance of ions across a cell membrane during a waveform, the data will normally be stored in the form of mathematical descriptions of virtual conductances (simulation algorithms) in either the memory or database. In this manner, the software can model either components of a biological cell or the entirety of a biological cell.

The simulation algorithms are designed to self-adjust to account for changes in the cell. The complexity of the simulation algorithms depends upon the number of factors that the dynamic clamp is designed to account for, including the number of ion channels or receptor types to be simulated. For example, for skeletal muscle cells, the action potential produced largely is generated by the interaction between sodium channels and potassium channels. However, for cardiac muscle cells the action potential produced is generated by the interaction of a greater number of ion channels or receptor types, resulting in more complex algorithms.

In addition, the data may contain parameters to account for losses in hardware, losses in the electrolyte in the pipette electrode (if used), at least one stimulation protocol and calculated variables as described herein. Accordingly, the simulation takes the measured waveform of the biological cell or portion thereof and generates a signal representative of the absent types of ion channels or receptors, to encourage the waveform to develop as it would if the all ion channels and receptors were functional.

The model of virtual conductances may include the kinetics of the virtual conductance (the rates of change of conductance to particular stimuli), the voltage dependence of virtual conductances (the equilibrium open probability of a conductance), and the maximum conductance of the biological channel expressed in the cell that is being recorded. This is particularly useful in determining a scaling factor for voltage clamp methods as this defines the maximum conductance that the channels expressed in the cell or portion thereof will produce. Moreover, without such scaling there may be insufficient current to support waveform, and especially action potential, generation. Scaling may also be useful for increasing reproducibility of the assay as variables such as membrane capacitance, leak conductance and maximum conductance of the expressed channel can all be scaled to predefined ratios. The model may also include the electrochemical properties of the system, including the reversal potentials of the virtual conductances (the membrane potential at which there is no net transmembrane flow of ions for a particular conductance) and other passive properties of the model system, including passive properties of both the biological cell or portion thereof and the components or entirety of the virtual cell. This may include the desired capacitance and resting conditions (such as resting conductance and resting voltage). The stimulation protocol is a user defined signal applied to the biological cell or portion thereof to generate desired physiological responses in the biological cell or portion thereof. The desired physiological response may be a waveform such as an action potential. These stimulation protocols allow the user to determine how the cell or portion thereof will be stimulated and to what degree. For example, these protocols allow the user to determine whether the cell or portion thereof is to be stimulated using voltage or current and the levels at which these stimuli will be set.

Stimulation protocols are useful where a biological cell or portion thereof is in a state whereby a waveform will not be produced, or will not be produced repetitively. When a biological cell or portion thereof is in such a state, assaying mutants may not be possible as the modulation of a waveform cannot be observed if no waveform is produced, or if it is produced too irregularly or too few times to allow accurate results to be measured. In such circumstances, the stimulation protocol can be used to produce a waveform, or cause its repetition. It achieves this by providing a stimulus that would not normally be exhibited by any of the types of ion channels or receptors the function of which the simulated signal is intended to replicate.

As biological cells differ in their electrophysiological properties, calculated variables are included in the simulation to allow the simulated signal to be tailored to the biological cell or portion thereof having the mutant ion channels or receptors. The calculated variables include the capacitance of the biological cell or portion thereof (determined from electrode measurements), modified virtual conductances (which are updated according to the cell or portion thereof to which the apparatus is in contact and modeled to form the simulation algorithms), and an output command signal that is dependent on the mode in which the software is operating (e.g., voltage or current-clamp mode).

In the voltage-clamp mode, the transmembrane or ionic current is measured by the amplifier through the electrode. It is then scaled to match the electrical parameters of the model system. The simulated signal, or transmembrane voltage (membrane potential), is then calculated by collecting the contributions from each of the virtual conductances, the capacitance of the virtual cell, the scaled ionic current recorded from the biological cell or portion thereof and the selected stimulation protocol. The output command signal is then set to this transmembrane voltage and subsequently sent to an amplifier for application to the biological cell or portion thereof.

In the current-clamp mode, the transmembrane voltage of the biological cell is measured by the amplifier through the electrode. The measurement may be filtered and sent to the computing system. The filtration prevents amplification of noise that could affect the calculation of the capacitance compensation term as previously described. The software calculates the capacitance compensation term by determining the capacitance of the cell or portion thereof and then applying a scaling factor to the rate of current application from each of the virtual conductances and the stimulation protocol. This can mathematically compensate for natural differences in the total capacitances of cells and normalize to a predefined capacitance level across all cells. The scaled output command signal is then sent to the amplifier for application to the biological cell or portion thereof. The software may be stored on any computer-readable medium such as a hard disk, removable memory device, external hard drive etc.

Methods of Use

In order to take readings, the present system passes through a plurality of operational phases. These phases may include, for example, initialization, real time looping for current or voltage-clamp mode, termination, and offline analysis. The initialization phase consists of hardware initialization, stimulation protocol selection, acquisition and validation of parameters and variables, and calculation of initial conditions. In particular, the hardware is initialized and tested to ensure it is functioning properly. This part of the initialization phase may include the testing of the operational limits of the hardware, passing inputs, to which inputs there is a predetermined or expected system response, to the hardware and comparing the hardware response to the predetermined response; and so forth.

The acquisition and validation of parameters and variables is particularly important so as to ensure all data necessary for the accurate simulation of responses to measurements taken from the biological cell or portion thereof can be produced. If some data are missing, such as a parameter representative of the response of a functional ion channel or receptor type in the biological cell, it may be collected before testing commences. This step may also ensure that the correct data for the operating mode of the apparatus and the selected stimulation protocol is acquired. It should be noted that although the system can operate in both current and voltage-clamp modes, the parameters and variables appropriate to one mode of operation may not be appropriate for the other.

The last stage of initialization is the calculation of initial conditions. This process sets the equipment default and references values which are useful in the process of recording data, such as a reference voltage and current. In addition, this step allows the calculated variables to be determined in order to adapt the test to different biological cells or portions thereof and cells that have been experimentally modified (e.g., with a mutation).

The next phase in the program is the real time looping phase. If the apparatus is operating in voltage-clamp mode, the transmembrane current from the biological cell or portion thereof is measured. The variables stored in software are updated in accordance with the measurement and an output command is generated. Simultaneously, this output command, that can be representative of the restoration current (the current required to return the membrane potential of the biological cell or portion thereof to the resting potential) or is alternatively the ionic currents that would be exhibited by functional ion channel and receptor types in the biological cell or portion thereof, is written to memory.

Similarly, when the apparatus is operating in current-clamp mode, the transmembrane voltage is measured by the amplifier through the electrode. The variables stored in software are updated in accordance with the measurement and an output command is generated. Simultaneously, this output command is written to memory.

During the termination phase, the output commands are set to levels at which it is safe to hold the biological cell or portion thereof. This ensures the cell remains functional, without being damaged, that parameters and responses that are generated remain fixed, and that the cell is in a predictable state for the next experiment. The data is then saved to hard disk or other appropriate medium, displayed to the user if desired, and the process is terminated.

Finally, during the offline analysis phase, calculations are performed to identify the initial conditions and parameters appropriate for the next iteration of testing. This data may also be displayed to the user. If a sufficient number of experiments have been performed, a model can be fitted to the data to describe the action of the mutant on the system.

The program may be stored in a single place on a computer readable medium. However, it may be advantageous for individual devices to store data relevant to their own operation. For example, the amplifier may store its own initialization data and sequence for initializing, and the computing system may store data for applying tests to determine the responses generated by the software are appropriate. The production of a waveform involves the activation of large numbers of multiple types of ion channels or receptors.

Biological Cells and Portions Thereof

A waveform may be produced at a whole biological cell or at a part of a biological cell. For example, the waveform may be produced at a part of a biological cell using a macropatch. A macropatch employs a large diameter pipette (for a pipette patch electrode) or a large aperture electrode (for a planar patch electrode) to surround a number of ion channels or receptors on a cell membrane. After forming a seal on the cell membrane using the macropatch, the electrode may be quickly withdrawn to separate a portion of the cell membrane (an inside-out patch). Alternatively after forming a seal, the cell membrane inside the electrode may be ruptured and then the electrode slowly withdrawn to separate a portion of the cell membrane (an outside-out patch).

In the methods described herein, a waveform is provided at the biological cell or portion thereof, and the effect of a mutation at a functional ion channel or receptor type is determined by detecting modulation of the waveform at the biological cell or portion thereof. A waveform may be provided in the biological cell or portion thereof in a number of ways. For example, in one embodiment the waveform may be initiated by the dynamic clamp.

In one embodiment, an ion channel or receptor type is present in the biological cell or portion thereof, but that ion channel or receptor type is not functional due to pharmacological inhibition. This may allow a greater number of types of biological cells or portions thereof to be used in the assays according to the present invention. For example, tetrodotoxin (TTX), saxitoxin or lidocaine may be used to block most voltage gated sodium channels. In another example, tetraethylammonium (TEA) and 4-aminopyridine (4-AP) may be used to block most voltage gated potassium channels.

In another embodiment, an ion channel or receptor type is present in the biological cell or portion thereof, but the dynamic clamp is used to subtract the signal from that ion channel or receptor type. This may allow validation of the predicted effect of that ion channel or receptor type on the waveform produced at the biological cell or portion thereof, or may provide additional information regarding the behavior of that ion channel or receptor type in the biological cell or portion thereof. Such techniques are known to a person skilled in the art and are described, for example, in Prinz et al. *Trends Neurosci.* 27: 218-224, 2004. In some cases, the dynamic clamp may also be used to simulate ion channels or receptors that are functional in the biological cell or portion thereof.

The biological cell may therefore be naturally occurring, already in existence, genetically modified or modified by interaction of, for example, an antagonist or virus. In one embodiment, the one or more ion channel or receptor types for providing a waveform are functional as they are expressed in the biological cell or portion thereof. Therefore in one embodiment, the biological cell may be a cell in which the genes for the one or more functional ion channel or receptor types have been inserted, or the biological cell may be a cell in which the genes for one or more functional ion channel or receptor types have been removed. In one embodiment, the biological cell is a cell in which the genes for one or more functional ion channel types have been inserted.

Host Cells

To produce a cell expressing one or more ion channels or receptors, the DNA sequence for the ion channel or receptor type (e.g., WT or mutant) may be obtained and then incorporated into an expression vector with an appropriate promoter. Once the expression vector is constructed, it may then be introduced into the appropriate cell line using methods including $CaCl_2$), CaPO4, microinjection, electroporation, liposomal transfer, dendrimers, viral transfer or particle mediated gene transfer.

The biological cell line (or host cell) may include prokaryote, yeast or higher eukaryote cells. Suitable prokaryotes may include, but are not limited to, eubacteria, such as Gram-negative or Gram-positive organisms, including Enterobacteriaceae. Such Enterobacteriaceae may include Bacilli (e.g., *B. subtilis* and *B. licheniformis*), *Escherichia* (e.g., *E. coli*), *Enterobacter, Erwinia, Klebsiella, Proteus, Pseudomonas* (e.g., *P. aeruginosa*), *Salmonella* (e.g., *Salmonella typhimurium*), *Serratia* (e.g., *Serratia marcescens*), *Shigella*, and *Streptomyces*. Suitable eukaryotic microbes include, but are not limited to, *Candida, Kluyveromyces* (e.g., *K. lactis, K. fragilis, K. bulgaricus, K. wickeramii, K. waltii, K. drosophilarum, K. thermotolerans* and *K. marxianus*), *Neurospora crassa, Pichia pastoris, Trichoderma reesia, Saccharomyces cerevisiae, Schizosaccharomyces pombe, Schwanniomyces* (e.g., *Schwanniomyces occidentalis*), filamentous fungi (e.g., *Neurospora, Penicillium, Tolypocladium*, and *Aspergillus* (e.g., *A. nidulans* and *A. niger*)), and methylotrophic yeasts (e.g., *Hansenula, Candida, Kloeckera, Pichia, Saccharomyces, Torulopsis*, and *Rhodotorula*). Suitable multicellular organisms include, but are not limited to, invertebrate cells (e.g., insect cells including *Drosophila* and *Spodoptera*), plant cells, and mammalian cell lines (e.g., Chinese hamster ovary (CHO cells), monkey kidney line, human embryonic kidney line, mouse Sertoli cells, human lung cells, human liver cells and mouse mammary tumor cells). An appropriate host cell can be selected without undue experimentation by a person skilled in the art.

In one embodiment, the biological cell or portion thereof is selected from the group consisting of a human embryonic kidney (HEK) cell, a COS cell, an LTK cell, a Chinese hamster lung cell, or a Chinese hamster ovary (CHO) cell or a *Xenopus* oocyte. In a further embodiment, the biological cell or portion thereof is a HEK cell or a COS cell, such as a HEK 293 cell or a COS-7 cell. The type of biological cell selected may affect the dynamic clamping technique employed. For example, the large size of *Xenopus* oocytes allows a two electrode clamp to be used far more readily than with mammalian cells, which are typically much smaller.

The cell line may then be cultured in conventional nutrient media modified for inducing promoters, selecting transformants, or amplifying the genes encoding the desired sequences. Culture conditions, such as media, temperature, pH, and the like, can be selected without undue experimentation by the person skilled in the art (for general principles, protocols and practical techniques, see Mammalian Cell Biotechnology: A Practical Approach, Butler, M. ed., IRL Press, 1991; Sambrook et al. Molecular Cloning: A Laboratory Manual, Cold Spring Harbor Laboratory Press, 1989). The cells may then be selected and assayed for the expression of the desired ion channel or receptor using standard procedures.

Ion Channels and Receptors

A number of functional ion channels or receptors are involved in providing a waveform in a biological cell. For example, this may include an ion channel selected from the group consisting of a sodium channel, a potassium channel, a calcium channel, a chloride channel or a hyperpolarisation-activated cation channel (H-channel). Accessory subunits of these channels may also be involved in providing a waveform.

A receptor for providing a waveform may be a receptor that is modulated following contact with a ligand. While modulation of an ion channel may also involve contact with a ligand (e.g., ligand-gated ion channels), ion channels may also open and close in response to changes in membrane potential (voltage-gated ion channels) or may be modulated by other means (e.g., mechanosensation or temperature).

Modulating encompasses any form of physical or chemical change. For example, this may include activation or inhibition of a receptor, the effect of agonists or antagonists at the receptor, up-regulation or down-regulation of a receptor, inhibition or activation of second messenger molecules, or receptor internalization. In one embodiment, modulation of the ion channel or receptor type is inhibition of the ion channel or receptor type. In another embodiment, modulation of the ion channel or receptor type is activation of the ion channel or receptor type. Modulation of an ion channel or receptor type also includes modulation of a subunit of the ion channel or receptor type. Selective modulation of specific subunits may be useful for determining the biophysical characteristics or certain mutations.

The ion channels described herein may be voltage-gated ion channels. The ion channel may be a sodium channel, a potassium channel, a calcium channel, a chloride channel, or a hyperpolarisation-activated cation channel. Calcium cations and chloride anions are involved in the production of a number of types of waveforms, such as the cardiac action potential and the action potential in various single-celled organisms. Calcium channels are known to play a role in controlling muscle movement as well as neuronal excitation, although intracellular calcium ions can, in some circumstances, activate particular potassium channels. In addition, chloride channels are known to aide in the regulation of pH, organic solute transport, cell migration, cell proliferation and differentiation.

In one embodiment, the ion channel or receptor type to be modulated is an N-type calcium channel or an L-type calcium channel. The N-type calcium channel may be an alpha(2)delta calcium channel subunit. In another embodiment, the L-type calcium channel may be $Ca_v$ 1.2.

Hyperpolarization-activated cation channels activate due to hyperpolarization of the cell membrane. These channels may be sensitive to cyclic nucleotides such as cAMP and cGMP and may be permeable to ions such as potassium ions and sodium ions. These channels assist in the propagation of an action potential. In one embodiment, the hyperpolarization-activated cation channel is hyperpolarization-activated cyclic nucleotide-gated potassium channel 1 (HCN1), hyperpolarization-activated cyclic nucleotide-gated potassium channel 2 (HCN2), hyperpolarization-activated cyclic nucleotide-gated potassium channel 3 (HCN3), or hyperpolarization-activated cyclic nucleotide-gated potassium channel 4 (HCN4).

Sodium channels are integral membrane proteins, and in cells such as neurons, sodium channels play a key role in the production of action potentials. In one embodiment, the sodium channel is a $Na_v$ 1.1 channel (voltage gated sodium channel, type I, alpha subunit; gene: SCN1A), a $Na_v$ 1.2 channel (voltage gated sodium channel, type II, alpha subunit; gene: SCN2A), a $Na_v$ 1.3 channel (voltage gated sodium channel, type III, alpha subunit; gene: SCN3A), a $Na_v$ 1.4 channel (voltage gated sodium channel, type IV, alpha subunit; gene: SCN4A), a $Na_v$ 1.5 channel (voltage gated sodium channel, type V, alpha subunit; gene: SCN5A), a $Na_v$ 1.6 channel (voltage gated sodium channel, type VIII, alpha subunit; gene: SCN8A), a $Na_v$ 1.7 channel (voltage gated sodium channel, type IX, alpha subunit; gene: SCN9A); a $Na_v$ 1.8 channel (voltage gated sodium channel, type X, alpha subunit; gene: SCN10A); or a $Na_v$ 1.9 channel (voltage gated sodium channel, type XI, alpha subunit; gene: SCN11A). In another embodiment, the sodium channel is a $Na_v$ 1.5 channel. In a further embodiment, the sodium channel is a $Na_v$ 1.4 channel.

Potassium channels are known mainly for their role in repolarizing the cell membrane following action potentials. They effectively work to restore the cell membrane to its resting potential and to reprime sodium channels for subsequent action potential firing. For example, IKR and $IK_vLQT1$ are known to be involved in repolarizing the cell after an action potential. In one embodiment, the potassium channel is a neuronal potassium channel, a delayed rectifier potassium channel, or an A-type potassium channel. In a further embodiment, the potassium channel is a Kv4.2 channel (voltage gated potassium channel, Sha1-related subfamily, member 2; gene: KCND2), a $K_v$4.3 channel (voltage gated potassium channel, Sha1-related subfamily, member 3; gene: KCND3), a $IK_vLQT1$ channel (also known as Kv7.1 channel; gene: KCNQ1), a hERG channel (also known as Kv11.1; gene: hERG (human Ether-a-go-go Related Gene or KCNH2)), a Kir2.1 channel (an inward rectifier potassium channel; gene: KCNJ2), a $K_{ir}$2.2 channel (an inward rectifier potassium channel; gene: KCNJ12), a $K_{ir}$2.3 channel (an inward rectifier potassium channel; gene: KCNJ4), a minK channel (voltage gated potassium channel, ISK-related family, member 1; gene: KCNEI), a MiRPI channel (voltage gated potassium channel, ISK-related family, member 2; gene: KCNE2), a MiRP2 channel (voltage gated potassium channel, ISK-related family, member 3; gene: KCNE3) or a MiRP3 channel (voltage gated potassium channel, ISK-related family, member 4; gene: KCNE4). In another embodiment, the potassium channel is an $IK_vLQT1$ channel.

In one embodiment, the potassium channel is a leak channel. Leak channels are also known as tandem-pore-domain potassium channels, and are known to include approximately 15 members. These channels are regulated by a number of factors including oxygen tension, pH, mechanical stretch and G-proteins.

In the case of an action potential, as the membrane potential increases, both the sodium and potassium channels begin to open. This process increases the passage of sodium ions into the cell and the balancing passage of potassium ions out of the cell. For small changes in membrane potential, the flow of potassium ions will overcome the flow of sodium ions and the membrane potential will return to its resting potential. However, if the voltage increases past a critical threshold, the flow of sodium ions suddenly increases and will temporarily exceed the flow of potassium ions, resulting in a condition whereby the positive feedback from the flow of sodium ions activates even more sodium channels. Thus, the cell produces an action potential. Therefore, in most cases the sodium and potassium channels are directly responsible for regulating the flow of ions across the cell membrane, which causes the firing of an action potential and the restoration of the cell membrane after the event.

Indications and Methods of Treatment

The present invention provides methods for treating diseases associated with GOF and LOF mutations. The dynamic clamps described herein may be used to determine whether a mutation is a GOF or LOF mutation. A GOF mutation is a mutation that increases the activity of a protein (e.g., ion channel or receptor) relative to WT. A LOF mutation is a mutation that decreases the activity of a protein (e.g., ion channel or receptor) relative to WT. After determining whether a mutation is GOF or LOF, a subject having the mutation may be further treated for a disorder associated with that particular mutation. In some instances, the subject will already have been previously determined to have a GOF or LOF mutation.

If the mutation is determined to be a GOF mutation, then methods of treatment may be employed to reduce the activity of the ion channel or receptor. Suitable therapies include knockdown with antisense oligonucleotides in order to reduce the activity of the ion channel or receptor to normal levels. Antisense oligonucleotides are single stranded oligonucleotides that hybridize to the mRNA of the target gene to prevent translation initiation. This in turn downregulates the production of the mutant ion channel or receptor.

If the mutation is determined to be a LOF mutation, then methods of treatment may be employed to increase the activity of the ion channel or receptor. Suitable therapies include upregulation with antisense oligonucleotides that hybridize to upstream open reading frames (uORFs) in order to restore the activity of the ion channel or receptor to normal levels. In these methods, antisense oligonucleotides hybridize to uORFs on the mRNA of the target gene to prevent translation initiation from the uORFs, thereby directing the translation machinery to increase production from the primary open reading frame (pORF). This in turn upregulates the production of the mutant ion channel or receptor.

Diseases known to be associated with mutations in ion channels that may be diagnosed and treated with the methods described herein include, for example, CNS disorders, skeletal muscle disorders, cardiac disorders, cancer, Immune disorders, and renal disorders.

Diseases associated with a variety of ion channels may be diagnosed and treated with the methods described herein. Furthermore, mutations in a variety of ion channels may be identified as GOF or LOF mutations. Such ion channels include, for example, calcium- and sodium-activated potassium channels, inwardly rectifying potassium channels, voltage-gated calcium channels, voltage-gated potassium channels, voltage-gated proton channels, voltage-gated sodium channels, calcium activated chloride channels, ClC channels, and maxi chloride channels.

Mutations and diseases associated with any of the ion channels listed in Table 1 may be determined as GOF or LOF, diagnosed, and treated according the methods described herein. Disease associated mutations in ion channels are described, for example, in Hübner et al. (Hum. Molec. Gen. 11:2435-2445, 2002), the disclosure of which is hereby incorporated by reference in its entirety.

TABLE 1

Ion channels and associated diseases

| Channel | Gene | Channel-forming unit/ligand | OMIM | Disease |
|---|---|---|---|---|
| Cation channels: | | | | |
| CHRNA1/ACHRA | CHRNA1 | α, ACh | 100690 | Myasthenia congenita |
| CHRNA4 | CHRNA4 | α, ACh | 118504 | Autosomal dominant nocturnal frontal lobe epilepsy |
| CHRNB2 | CHRNB2 | β, ACh | 118507 | Autosomal dominant nocturnal frontal lobe epilepsy |
| Polycystin-2 | PKD2 | α | 173910 | Autosomal dominant polycystic kidney disease (ADPKD) |
| CNGA3 | CNGA3 | α, cGMP | 600053 | Achromatopsia 2 (color blindness) |
| CNGB1 | CNGB1 | β, cGMP | 600724 | Autosomal recessive retinitis pigmentosa |
| CNGB3 | CNGB3 | β, cGMP | 605080 | Achromatopsia 3 |
| Sodium channels: | | | | |
| $Na_v1.1$ | SCN1A | α | 182389 | Generalized epilepsy with febrile seizures (GEFS+) |
| $Na_v1.2$ | SCN2A | α | 182390 | Generalized epilepsy with febrile and afebrile seizures |
| $Na_v1.3$ | SCN3A | α | 617935 | Epilepsy, familial focal, with variable foci 4 |
| | | α | 617938 | Epileptic encephalopathy, early infantile, 62 |
| | | α | | West syndrome, autism spectrum disorder, early infantile epileptic encephalopathy, seizures |
| $Na_v1.4$ | SCN4A | α | 603967 | Paramyotonia congenita, potassium aggressive myotonia, hyperkalemic periodic paralysis |
| $Na_v1.5$ | SCN5A | α | 600163 | Long-QT syndrome, progressive familial heart block type I, Brugada syndrome (idiopathic ventricular arrhythmia) |
| $Na_v1.6$ | SCN8A | α | 600702 | Epileptic encephalopathy, early infantile epileptic encephalopathy, benign familial infantile seizures |
| SCN1B | SCN1B | β | 600235 | Generalized epilepsy with febrile seizures (GEFS+) |
| ENaCα | SCNN1A | α | 600228 | Pseudohypoaldosteronism type 1 (PHA1) |
| ENaCβ | SCNN1B | β | 600760 | PHA1, Liddle syndrome (dominant hypertension) |
| ENaCγ | SCNN1G | | 600761 | PHA1, Liddle syndrome |
| Potassium channels: | | | | |
| $K_v1.1$ | KCNA1 | α | 176260 | Episodic ataxia with myokymia |
| $K_v3.1$ | KCNC1 | α | 616187 | Epilepsy, progressive myoclonic 7 Intellectual disability without seizures, ataxia |
| KCNQ1/$K_v$LQT1 | KCNQ1 | α | 192500 | Autosomal dominant long-QT syndrome (Romano-Ward) Autosomal recessive long-QT syndrome with deafness (Jervell-Lange-Nielsen) |
| | | | 607542 | Atrial fibrillation, familial 3, Jervell and Lange-Nielson syndrome, Long QT syndrome 1, Short QT syndrome 2 |
| KCNQ2 | KCNQ2 | α | 602235 | BFNC (epilepsy), also with myokymia |

TABLE 1-continued

Ion channels and associated diseases

| Channel | Gene | Channel-forming unit/ligand | OMIM | Disease |
|---|---|---|---|---|
| KCNQ3 | KCNQ3 | α | 602232 | BFNC (epilepsy) |
| KCNQ4 | KCNQ4 | α | 603537 | DFNA2 (dominant hearing loss) |
| KCNT1 | KCNT1 | α | 608167 | Epileptic encephalopathy (early infantile epileptic encephalopathy), malignant migrating partial seizures of infancy, nocturnal frontal lobe epilepsy |
| HERG/KCNH2 | KCNH2 | α | 152427 | Long-QT syndrome |
| Kir1.1/ROMK | KCNJ1 | α | 600359 | Bartter syndrome (renal salt loss, hypokalemic alkalosis) |
| Kir2.1/IRK/KCNJ2 | KCNJ2 | α | 600681 | Long-QT syndrome with dysmorphic features (Andersen syndrome) |
| Kir6.2/$K_{ATP}$ | KCNJ11 | α | 600937 | Persistent hyperinsulinemic hypoglycemia of infancy (PHHI) |
| SUR1 | SUR1 | β | 600509 | PHHI |
| KCNA2 | KCNA2 | | 616366 | Epileptic encephalopathy, early infantile, 32 |
| KCNE1/MinK/ISK | KCNE1 | β | 176261 | Autosomal dominant long-QT syndrome (Romano-Ward) Autosomal recessive long-QT syndrome with deafness (Jervell-Lange-Nielsen) |
| KCNE2/MiRP1 | KCNE2 | β | 603796 | Long-QT syndrome |
| KCNE3/MIRP2 | KCNE3 | β | 604433 | Periodic paralysis |
| KCNMA1 | KCNMA1 | | 617643 | Cerebellar atrophy, developmental delay, seizures |
| | | | 609446 | Paroxysmal nonkinesigenic dyskinesia, 3, with or without generalized epilepsy |
| HCN1 | HCN1 | | 615871 | Epileptic encephalopathy, early infantile, 24 |
| HCN2 | HCN2 | | 602781 | Febrile seizures, generalized epilepsy with febrile seizures plus |
| HCN4 | HCN4 | | 613123 | Brugada syndrome 8 |
| | | | 163800 | Sick sinus syndrome 2 Generalized epilepsy |
| Calcium channels: | | | | |
| $Ca_v1.1$ | CACNA1S | α | 114208 | Hypokalemic periodic paralysis, malignant hyperthermia |
| $Ca_v1.4$ | CACNA1F | α | 300110 | X-linked congenital stationary night blindness |
| $Ca_v2.1$ | CACNA1A | α | 601011 | Familial hemiplegic migraine, episodic ataxia, spinocerebellar ataxia type 6 |
| $Ca_v3.1$ | CACNA1G | α | 616795 | Spinocerebellar ataxia 42 |
| $Ca_v3.2$ | CAGNA1H | α | 617027 | Hyperaldosteronism, familial, type IV |
| | | α | 611942 | Epilepsy, childhood absence, susceptibility to, 6, Epilepsy, idiopathic generalized, susceptibility to, 6 |
| | | α | 618087 | Spinocerebellar ataxia 42, early-onset, severe, with neurodevelopmental deficits |
| RyR1 | RYR1 | α | 180901 | Malignant hyperthermia, central core disease |
| RyR2 | RYR2 | α | 180902 | Catecholaminergic polymorphic ventricular tachycardia, arrhythmogenic right ventricular dysplasia type 2 |
| Chloride channels: | | | | |
| CFTR | ABCC7 | α | 602421 | Cystic fibrosis, congenital bilateral aplasia of vas deferens |
| ClC-1 | CLCN1 | α | 118425 | Autosomal recessive (Becker) or dominant (Thomsen) myotonia |
| ClC-5 | CLCN5 | α | 300008 | Dent's disease (X-linked proteinuria and kidney stones) |
| ClC-7 | CLCN7 | α | 602727 | Osteopetrosis (recessive or dominant) |
| ClC-Kb | CLCNKB | α | 602023 | Bartter syndrome type III |
| Barttin | BSND | β | 606412 | Bartter syndrome type IV (associated with sensorineural deafness) |

TABLE 1-continued

Ion channels and associated diseases

| Channel | Gene | Channel-forming unit/ligand | OMIM | Disease |
|---|---|---|---|---|
| GLRA1 | GLRA1 | α, glycine | 138491 | Hyperekplexia (startle disease) |
| GABAα1 | GABRA1 | α, GABA | 137160 | Juvenile myoclonus epilepsy |
| GABAγ2 | GABRG2 | γ, GABA | 137164 | Epilepsy |
| Gap junction channels: | | | | |
| Cx26 | GJB2 | | 121011 | DFNA3 (autosomal dominant hearing loss) DFNB1 (autosomal recessive hearing loss) |
| Cx30 | GJB4 | | 605425 | DFNA3 |
| Cx31 | GJB3 | | 603324 | DFNA2 |
| Cx32 | GJB1 | | 304040 | CMTX (X-linked Charcot-Marie-Tooth neuropathy) |

Abbreviations. OMIM = Online Mendelian Inheritance in Man

EXAMPLES

Example 1. Dynamic Action Potential Clamp Predicts Functional Separation in Mild Familial and Severe De Novo Forms of SCN2A Epilepsy De novo variants in SCN2A developmental and epileptic encephalopathy (DEE) showed distinctive genotype-phenotype correlations. The two most recurrent SCN2A variants in DEE, R1882Q and R853Q are associated with different ages and seizure types at onset. R1882Q presents on day one of life with focal seizures while infantile spasms is the dominant seizure type seen in R853Q cases, presenting at a median age of eight months. Voltage clamp, which characterizes the functional properties of ion channels, predicted gain-of-function for R1882Q and loss-of-function for R853Q. Dynamic action potential clamp, that we implement here as a method for modeling neurophysiological consequences of a given epilepsy variant, predicted that the R1882Q variant would cause a dramatic increase in firing, whereas the R853Q variant would cause a marked reduction in action potential firing. Dynamic clamp was also able to functionally separate the L1563V variant, seen in benign familial neonatal-infantile seizures from R1882Q, seen in DEE, suggesting a diagnostic potential for this type of analysis. Overall, a strong correlation was observed between clinical phenotype, SCN2A genotype and functional modeling. Dynamic clamp is well positioned to impact our understanding of pathomechanisms and for development of disease mechanism targeted therapies in genetic epilepsy.

Mutations in SCN2A, encoding the voltage-gated sodium channel type IIa subunit ($Na_v$ 1.2) cause familial and sporadic brain disorders. Familial mutations were first identified in self-limited, pharmacoresponsive epilepsy typically arising from gain-of-function mutations, whereas de novo mutations were only more recently discovered and have been recognised as the most frequent cause of neurodevelopmental disorder. The phenotypic spectrum of SCN2A mutations is broad, ranging from age-limited, pharmacoresponsive epilepsy with normal development, to severe conditions with refractory epilepsy and severe developmental impairment, known as developmental and epileptic encephalopathies (DEE). DEEs are a group of brain disorders with impairment of neurodevelopment where epileptic activity per se adds to the neurodevelopmental impairment.

Within the DEEs, distinct phenotypes are emerging among individuals with SCN2A variation. Particularly, there is a group of patients with seizure onset in the early infantile period ('early-onset') in whom sodium channel blockers such as phenytoin and carbamazepine may improve seizures, and a group with seizure onset later in infancy ('later-onset' group, >3 months) in whom sodium channel blockers are rarely effective. It has been postulated that the difference in clinical features and treatment response are due to differential effects of the SCN2A mutations on $Na_v$ 1.2 channel function. De novo SCN2A variants exhibiting $Na_v$ 1.2 channel gain-of-function are typically associated with epilepsy, whereas it has been proposed that partial or complete $Na_v$ 1.2 channel loss-of-function would invariably lead to autism spectrum disorder. However, more recently, loss-of-function has been also associated with 'later-onset' epilepsy, suggesting the genotype-phenotype correlation may be more complex.

Therefore, there is an urgent need for a comprehensive understanding of the biophysical, neurophysiological and clinical impacts of different mutation classes for diagnosis and for the development of disease mechanism-based therapies. Here, we undertook a detailed functional analysis of two of the most recurrent SCN2A variants, R1882Q and R853Q. We present a comprehensive clinical evaluation for all R1882Q and R853Q cases where records or literature data was available. In addition, we implemented dynamic action potential clamp analysis to the study of SCN2A variants in epilepsy and showed how this approach has the potential to provide a rapid and definitive prediction of neuron scale phenotypic consequences.

Functional studies of $Na_v$ 1.2 channel variants in mammalian cells or *Xenopus* oocytes using patch-electrode and two-electrode voltage clamp, respectively, represent the current gold standard for analysis of SCN2A and other voltage-gated ion channels in epilepsy. Both these methods are able to dissect various functional states of ion channel behaviour, typically including voltage dependence and kinetics of various transitions from open to inactivated and the reversal or recovery of these states. Often, functional analysis is followed by an intuitive interpretation to predict whether a particular change in a biophysical character would enhance or diminish the activity in the neuron in which a particular ion channel resides. This can lead to various interpretations of enhanced excitability in pyramidal neurons or disinhibition in interneurons that are credited with being the underlying cause of a particular epilepsy syndrome. More formal but time-consuming post-hoc computational analysis of the biophysical properties of a given channel can be undertaken to remove the perils of intuition and the bias of interpretation but these are rarely undertaken.

The recently developed dynamic action potential clamp methodology can bridge the divide from intuition to formal modeling and can enable rapid and unambiguous determination of the effects of ion channel mutations on neuronal excitability without the need for time-demanding voltage clamp characterization. This method produces a real-time coupling between a biological cell and an in silico cell to generate a hybrid neuron model that predicts the impact of ion channel variation on neuronal excitability. Unlike traditional post hoc modeling, there is no need to comprehensively characterise the underlying biophysics of the channel of interest. By using a variety of in silico models it is possible to gauge the impact of a variant in different neuronal compartments, such as soma, axon initial segment or dendrite, or even different neuronal types such as interneuron or cortical layer specific pyramidal neuron to provide different contexts for interpreting disease mechanisms.

Here, we deployed the dynamic action potential clamp approach to analyse the impacts of the R853Q and R1882Q DEE variants as well as the L1563V variant previously associated with inherited benign familial neonatal infantile seizures (BFNIS). R853Q and R1882Q are the most frequently identified SCN2A variants and are associated with specific phenotypes. We not only showed how successfully dynamic action potential clamp analysis could recapitulate and surpass voltage clamp findings but also demonstrated how it could be superior to intuitive interpretation when faced with biophysical changes that have opposing effects on excitability. Our dynamic action potential clamp data directly demonstrated that the early onset R1882Q DEE variant resulted in increased neuronal excitability and that the late-onset R853Q DEE variant results in decreased neuronal excitability. Voltage clamp analysis of the L1563V variant associated with self-limited and pharmacoresponsive BFNIS resulted in opposing changes in voltage dependence of activation and inactivation with enhanced recovery from fast inactivation whose impact on excitability would be difficult to interpret. Dynamic action potential clamp clearly predicted how these opposing changes could result in an enhanced excitability profile and how this could be separated from the functional profile of the more severe R1882Q variant.

Patients with SCN2A Mutations

Seven individuals with the R1882Q and twelve with the R853Q recurrent mutations were identified. Distinct phenotypic features, particularly age of seizure onset and initial seizure type, applied to the patient groups with R1882 or R853Q mutations (Table 5). Sodium channel blockers were mainly beneficial in the R1882Q group. Movement disorders, occurred in both groups; however, severe choreoathetosis only occurred with the R853Q mutation. The cellular and network pathophysiological mechanism leading to movement disorders in these patients are unknown.

Figures 1A, 1B, 1C:
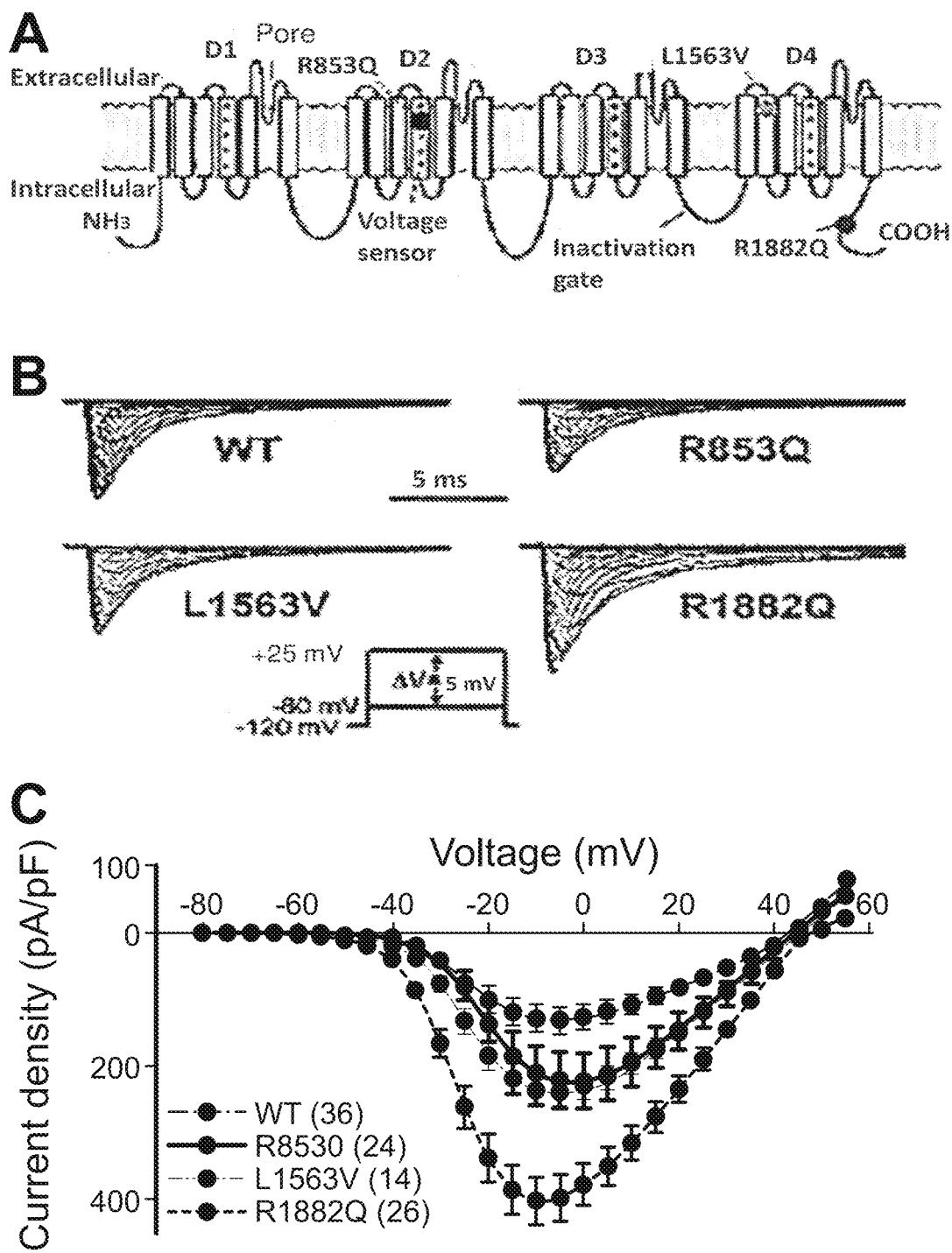
FIGS. 1A-1D are a set of schematic drawings and graphs showing the location of $Na_v1.2$ mutations and biophysical properties of wild-type (WT), R853Q, L1563V and R1882Q channels.
Figure 1D:
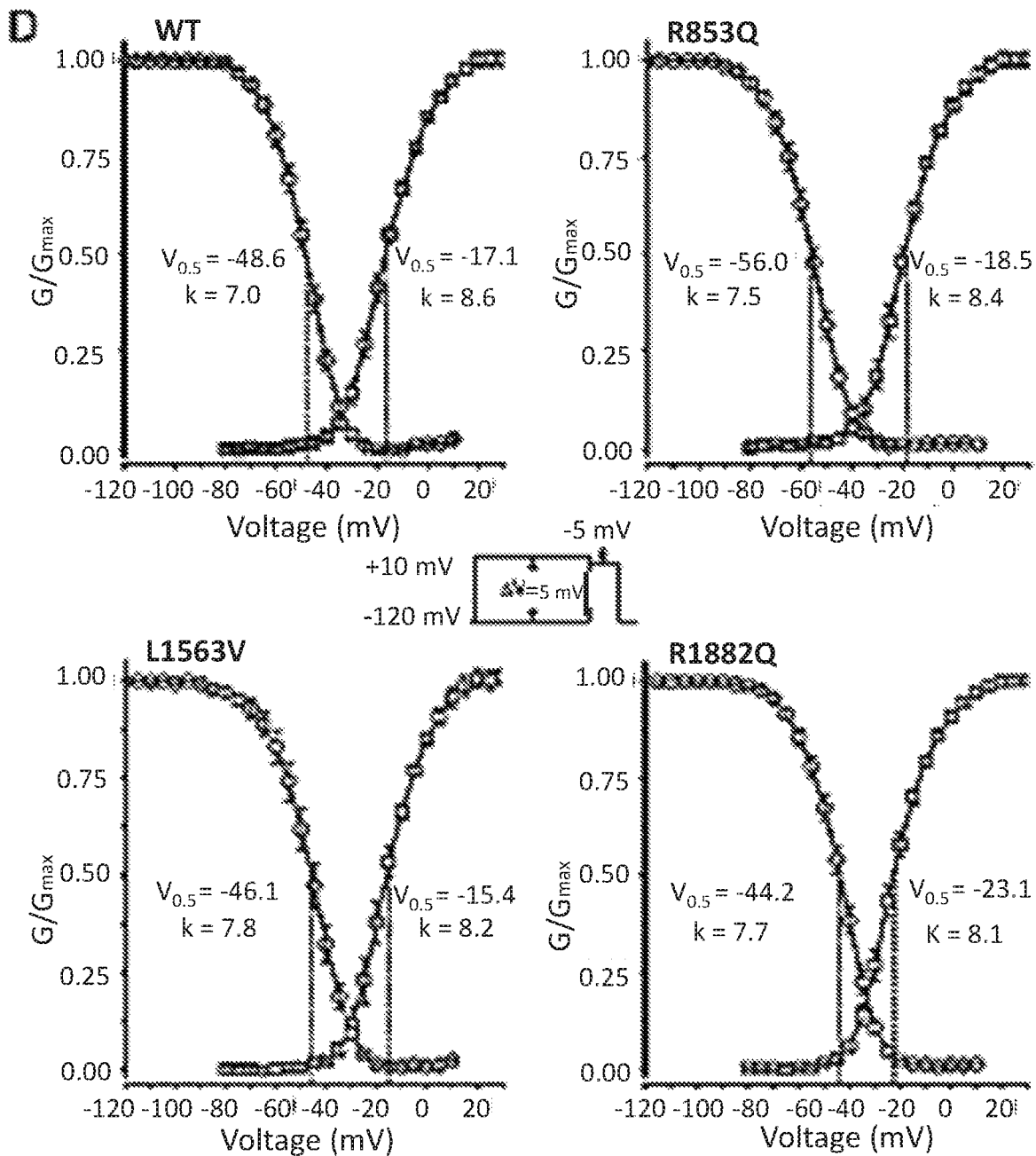

Biophysical Characterization of $Na_v$ 1.2 Channel Variants Using Conventional Voltage Clamp To understand the basis of clinical heterogeneity in SCN2A-associated disorders, the biophysical consequences of $Na_v$ 1.2 channel mutations and their impact on action potential firing and neuronal excitability must be clarified. Representative current traces from CHO cells transiently expressing wild-type or mutant $Na_v$ 1.2 channels are shown in FIG. 1B. Peak sodium current ($I_{Na}$) densities in cells expressing L1563V channels were similar to those of wild-type channels, whereas $I_{Na}$ densities were decreased in cells harbouring R853Q channels and increased in cells harbouring R1882Q channels (FIG. 10, Table 2). The effects of mutations on $Na_v$ 1.2 channel gating over a range of membrane potential ($V_m$) values are shown in FIG. 1D. Relative to wild-type, the activation curves of R853Q and L1563V channels exhibited small but statistically significant hyperpolarizing or depolarizing shifts, respectively. R1882Q channel activation was more severely affected, resulting in a 6 mV hyperpolarizing shift of the $V_{0.5,act}$ value, a change that results in increased sodium channel availability compared to the wild-type (FIG. 1D, Table 2). In all mutants, the $V_{0.5,inact}$ values were significantly changed compared to wild-type (FIG. 1D, Table 2). In cells expressing R853Q channels, the hyperpolarizing shift of $V_{0.5,inact}$ stabilizes inactivation and leads to reduced sodium channel availability at physiologically relevant $V_m$ values. Conversely, the depolarizing shift of $V_{0.5,inact}$ increases sodium channel availability for L1563V and R1882Q variants.

TABLE 2

Biophysical parameters of INa through Nav1.2 channel variants

| Biophysical property | Wild-type | R853Q | L1563V | R1882Q |
|---|---|---|---|---|
| Current density (pA/pF) | 240.4 ± 21 | 130.7 ± 19* | 222.7 ± 42 | 402.0 ± 36**** |
| n | 36 | 24 | 14 | 26 |
| Activation | | | | |
| $V_{0.5,act}$ (mV) | −17.06 ± 0.25 | −18.49 ± 0.31*** | −15.39 ± 0.29*** | −23.08 ± 0.26**** |
| $K_{act}$ (mV) | 8.63 ± 0.25 | 8.44 ± 0.28 | 8.19 ± 0.26 | 8.09 ± 0.26 |
| n | 36 | 24 | 14 | 26 |
| Inactivation | | | | |
| $V_{0.5,act}$ (mV) | −48.60 ± 0.24 | −55.98 ± 0.69 | −46.08 ± 0.49*** | −44.23 ± 0.26* |
| $K_{act}$ (mV) | 7.00 ± 0.21 | 7.45 ± 0.35 | 7.83 ± 0.44 | 7.67 ± 0.24 |
| n | 31 | 21 | 14 | 25 |
| Open probability ($P_o$) | | | | |
| m × h | 0.012 ± 4e$^{-5}$ | 0.0078 ± 3e$^{-5****}$ | 0.016 ± 4e$^{-5****}$ | 0.036 ± 2e$^{-5****}$ |
| $x_c$ (mV) | −38.7 ± 0.1 | −41.0 ± 0.2* | −30.1 ± 0.1**** | − 34.0 ± 0.2**** |
| $w_1$ (mV) | 14.9 ± 0.1 | 16.9 ± 0.2* | 16.4 ± 0.1* 1**** | 14.43 ± 0.2 |
| $w_2$ (mV) | 16.9 ± 0.1 | 18.5 ± 0.2* | 16.19 ± 0.1* | 14.53 ± 0.2**** |
| Window INa area (% of total) | 1.1 ± 0.06 | 0.91 ± 0.05* | 1.35 ± 0.09* | 2.1 ± 0.14** |

TABLE 2-continued

Biophysical parameters of INa through Nav1.2 channel variants

| Biophysical property | Wild-type | R853Q | L1563V | R1882Q |
|---|---|---|---|---|
| Persistent $I_{Na}$ | | | | |
| at −30 mV (% of total) | 1.18 ± 0.13 | 1.24 ± 0.14 | 1.23 ± 0.22 | 2.92 ± 0.25* |
| n | 30 | 21 | 14 | 25 |
| Biophysical property | Wild-type | R853Q | L1563V | R1882Q |
| Time course of fast inactivation | | | | |
| $\tau_f$ at −30 mV (ms) | 2.43 ± 0.20 | 2.23 ± 0.25 | 2.47 ± 0.24 | 3.26 ± 0.22** |
| n | 20 | 14 | 11 | 20 |
| Time course of recoverys§ | | | | |
| $\tau$ at −120 mV (ms) | 0.90 ± 0.06 | 0.93 ± 0.09 | 0.51 ± 0.07**** | 0.92 ± 0.06 |
| $\tau$ at −70 mV (ms) | 8.22 ± 0.3 | 8.29 ± 0.5 | 3.47 ± 0.2**** | 8.35 ± 0.5 |
| n | 16 | 14 | 10 | 15 |
| Slow inactivated $_{INa}$ fraction | | | | |
| after 195, at −60 mV | 0.23 ± 0.02 | 0.33 ± 0.02** | 0.16 ± 0.02* | 0.21 ± 0.02 |
| after 195, at −50 mV | 0.62 ± 0.02 | 0.71 ± 0.02** | 0.51 ± 0.02*** | 0.61 ± 0.02 |
| n | 12 | 9 | 9 | 8 |
| Time course of slow inactivation | | | | |
| $\tau_f$ at −60 mV (ms) | 677.5 ± 28 | 310.6 ± 18 | 5279 ± 480* | 1508 ± 144 |
| $\tau_f$ at −50 mV (ms) | 777.0 ± 36 | 650 ± 43 | 2443 ± 207**** | 1240 ± 111* |
| $\tau_s$ at −60 mV (s) | 70.0 ± 11.1 | 78.0 ± 8.4 | 84.4 ± 19.6 | 68.6 ± 6.2 |
| $\tau_s$ at −50 mV (s) | 46.6 ± 6.5 | 47.6 ± 7.7 | 52.4 ± 6.5 | 47.2 ± 5.6 |
| n | 12 | 9 | 9 | 8 |

Abbreviations. Data are represented as mean ± SEM; n, number of cells measured, $V_{0.5,(in)act}$, membrane potential for half-maximal (in)activation; $K_{(in)act}$, slope factor of steady-state (in)activation curve; m, probability that the channel is activated; h, probability that a channel is not inactivated; A represents the peak of the $P_o$ curve, $x_c$ is the voltage below the peak, $w_1$ and $w_2$ represent width for m and h, respectively; tf and ts, fast and slow time constants, respectively; Af and As, fractions of fast and slow recovery from inactivation; *P < 0.05, P < 0.01,  P < 0.001, or ***P < 0.0001 compared with wild-type, one-way ANOVA with Bonferroni correction;
§Recovery from fast inactivation.

The overlapping regions of the $I_{Na}$ activation and inactivation curves (FIG. 1D) suggested the presence of a "window current" arising from partial activation and incomplete inactivation of the $Na_v$ 1.2 channel. Inward window current is capable of contributing to depolarization even at resting potentials. We determined the voltage dependence of the quasi-steady-state open probability ($P_o$) of the wild-type and mutants channels (FIG. 2A). The peak of the $P_o$ distribution of R1882Q channels was markedly greater than that seen in wild-type, whereas the peak of the $P_o$ distribution of L1563V was only modestly greater than wild-type. By contrast, R853Q channels showed a significant reduction in the peak of the $P_o$ distribution (FIG. 2A, Table 2). The areas under the $P_o$ distribution for each variant were used to estimate the overall contribution of window current to the total $I_{Na}$ (FIG. 2A, Table 2). Compared to wild-type, this value decreased for R853Q channels and showed moderate or large increase for L1563V or R1882Q channels, respectively. For R853Q channels we also hypothesised that replacement of the positively charged arginine in the voltage sensor with the neutral amino acid glutamine could result in gating pore current. However, we were unable to demonstrate the presence of pore currents in cells expressing R853Q channels (FIGS. 3A-3B and 15-36), suggesting that pore currents do not contribute to the pathophysiological mechanism in these cells.

Figure 2B:
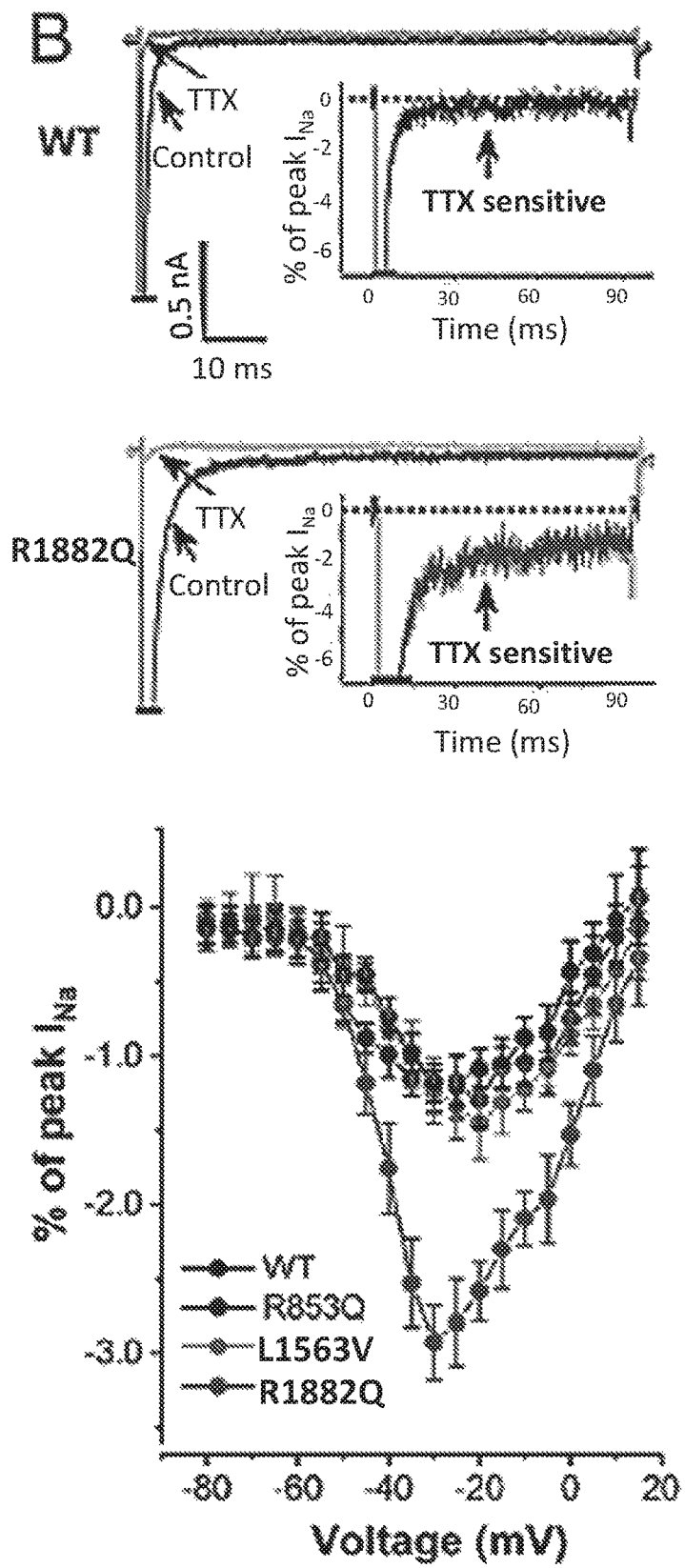
Figure 2C:
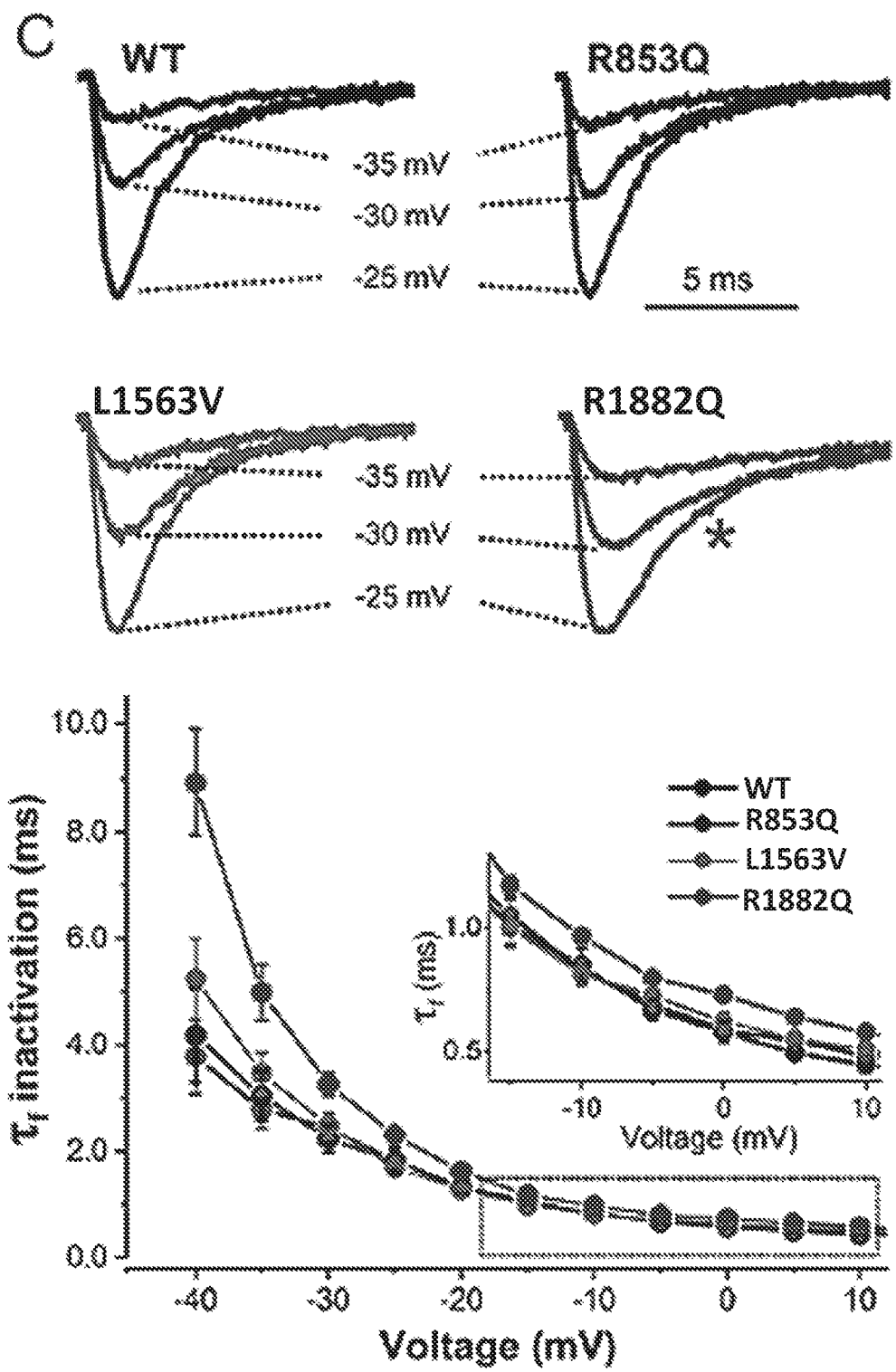

In cells expressing R1882Q channels, the analysis of $I_{Na}$ during depolarization revealed a slower time course of inactivation compared with wild-type channels and the presence of a non-inactivating persistent inward $I_{Na}$ that was nearly absent in cells expressing wild-type channels (FIG. 2B). The persistent $I_{Na}$ was sensitive to 100 nM tetrodotoxin, indicating that this current component was mediated by the transfected $Na_v$ 1.2 channels and not an endogenous current. In cells expressing R853Q and L1563V channels, the magnitude of persistent $I_{Na}$ was similar to that of wild-type channels (FIG. 2B, Table 2). In the voltage range between −40 mV and +10 mV, the time constants of peak $I_{Na}$ inactivation of R853Q and L1563V channels were unchanged compared with wild-type, whereas R1882Q channels exhibited impaired fast inactivation (FIG. 2C, Table 2).

Figure 4A:
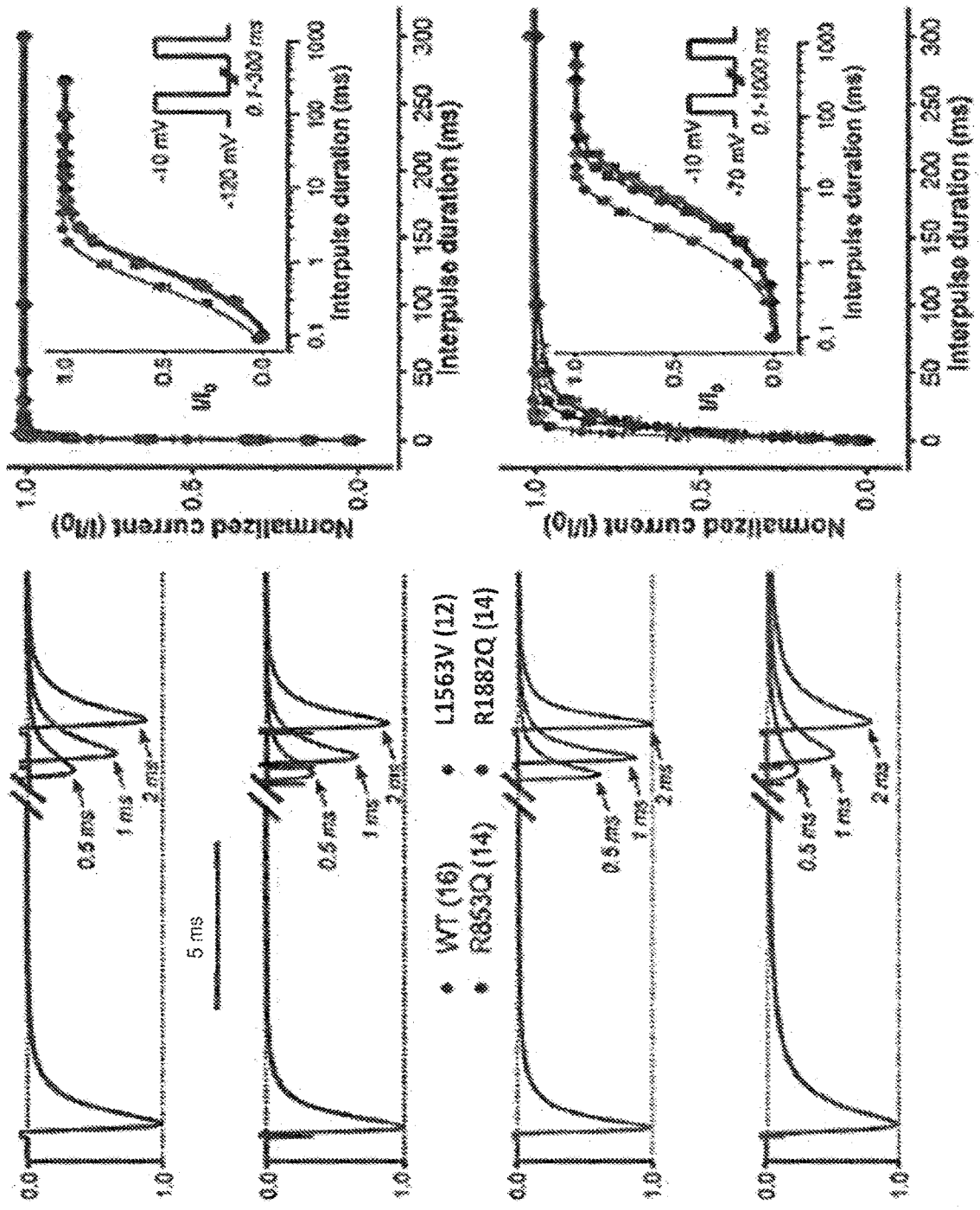
Figure 14:
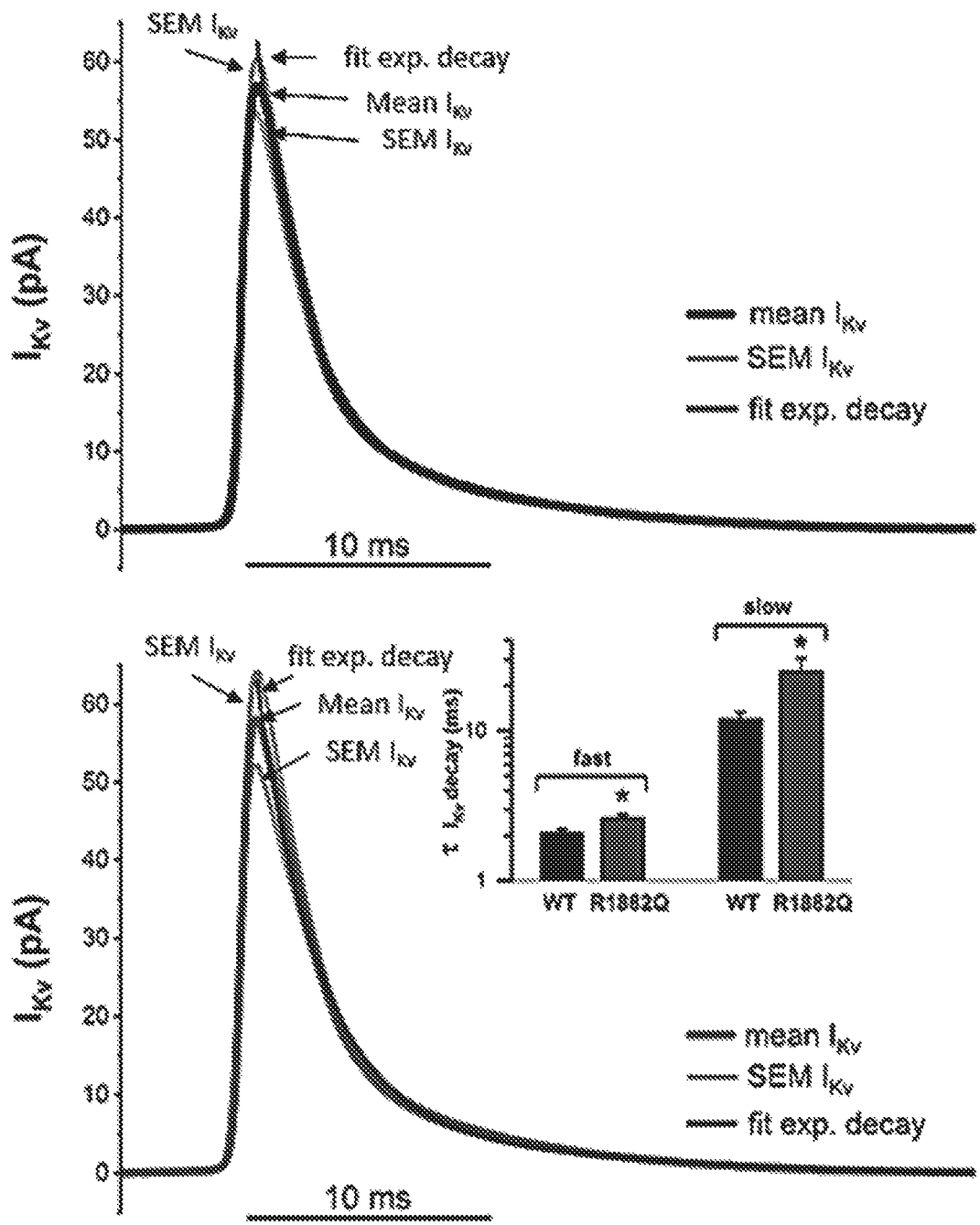
FIG. 14 is a graph showing the magnitude of $I_{Kv}$ and the time course of $I_{Kv}$ decay in dynamic clamp experiments implementing wild-type (n=5, top) or R1882Q $I_{Nav1.2}$ (n=4, bottom). Mean $I_{Kv}$ was determined by averaging the first eight to twelve action potential-associated $I_{Kv}$ traces using data shown in FIGS. 12A-12B (at $g_e:g_i=2$). For both 'wild-type' and 'R1882Q', the peak $I_{Kv}$ values were similar, 56.9±3.5 pA and 58.1±5.9 pA, respectively. The time course of mean $I_{Kv}$ decay was fitted with a double-exponential equation (blue traces, top and bottom panels)

Next, we studied the kinetic features of recovery and slow inactivation of wild-type and mutant $Na_v$ 1.2 channels. Recovery from inactivation in sodium channels is a time- and voltage dependent process following action potentials or depolarizing voltage steps. For example, as shown in FIG. 4A, wild-type or variants channel recovery was around ten times more rapid at −120 mV compared to −70 mV. Interestingly, only the L1563V variant showed a significantly more rapid recovery than wild-type channels, consistent with a gain-of-function effect. In contrast, the time constants of recovery for R853Q and R1882Q channels were similar to that of wild-type (FIG. 4A, Table 2). We evaluated the entry of wild-type and variant channels into slow inactivation. Both the time course and the extent of slow inactivation were enhanced at more depolarising potentials (FIG. 4B), consistent with earlier studies. At two different test voltages, R1882Q channels entered slow inactivation similarly to wild-type channels, whereas L1563V showed reduced entry and R853Q showed enhanced entry (FIG. 4B, Table 2).

Dynamic Action Potential Clamps Studies of Epileptogenic $Na_v$ 1.2 Channels

In dynamic clamp mode (FIG. 5A), we characterised the voltage responses of the hybrid cell model incorporating wild-type or mutant (R853Q, L1563V, or R1882) $I_{Na}$ expressed in CHO cells, and leak and delayed rectifier currents represented solely in the in silico model. We used two stimulating protocols to elicit action potentials. First, we used current steps of 500 or 1000 ms duration and an example trace of such an experiment is shown in FIG. 5B. The input-output relationships, representing the number of action potentials elicited by the corresponding current input in the axon initial segment (AIS) model cell are shown in FIG. 5C. In dynamic clamp experiments comparing the input-output curves it was readily apparent that each variant produced a unique profile. R1882Q had a left shift in the rheobase and achieved significantly higher action potential firing than wild-type or R853Q channels (FIGS. 5C and 5D). L1563V channels had a rheobase similar to wild-type but exhibited a markedly higher gain and could achieve a peak action potential firing rate similar to R1882Q. R853Q channels showed a significantly reduced action potential firing rate across a broad range of input currents beyond what might have been expected by visual inspection of voltage clamp data alone, highlighting the utility of the dynamic action potential clamp approach in resolving the impact of multiple changes in biophysical properties.

Next, we used more biologically realistic stimuli to investigate the modulation of action potential firing activity by using the Ornstein-Uhlenbeck model of synaptic noise (FIGS. 6A and 6B). This form of stimulation differed from the step current in that it produced more random action potential firing intervals and achieved a lower overall frequency of firing more reminiscent of the type of behaviour seen in real neurons. The overall pattern of the input-output relationships formed using synaptic stimulation versus step current was very similar, providing an additional validation of the variant behaviour whilst allowing for additional parameters to be extracted from the analysis such as inter-spike interval, $V_m$, and the ability to model the effect sustained $V_m$ levels at different conductance states. In hybrid neurons incorporating either wild-type or mutant $I_{Na}$, we scaled the synaptic current using a set of excitatory ($g_e$) to inhibitory ($g_i$) conductance ratios and probed the input-output profile (FIGS. 6C and 6D). Increasing the $g_e$:$g_i$ ratio from 1 to 3 produced gradual $V_m$ depolarizations and high-amplitude $V_m$ fluctuations of the model cell, typical for cortical neurons in vivo. Over a wide range of $g_e$:$g_i$ ratios, the R853Q containing hybrid model exhibited significantly decreased action potential firing, whereas the R1882Q containing hybrid model showed a significantly increased action potential firing. Analysis of L1563V in the dynamic clamp showed a similar rheobase to wild-type and could achieve levels of action potential firing to that seen with R1882Q at higher levels of stimulation (FIGS. 6C and 6D). Inspection of the $I_{Na}$ action currents showed how increasing $g_e$:$g_i$ ratios decreased availability as reflected by the reduced peak $I_{Na}$ during repetitive action potential firing. Detailed analysis of action potential waveforms was undertaken for wild-type or mutant channels (FIG. 6E), and the relationship of the $g_e$:$g_i$ ratio of the stimulating current to steady-state $V_m$, action potential upstroke velocity (AP rise), action potential width, and the time constant of action potential decay are shown (FIG. 6E). Relative to wild-type, the AIS model cell incorporating R1882Q channels was more depolarized and exhibited wider action potentials that repolarized slower, whereas these features were unchanged in model cells incorporating R853Q or L1563V channels. As shown with step current input, the BFNIS variant L1563V produced action potential firing that was similar to control for smaller $g_e$:$g_i$ ratios (2.5) but departed significantly from wild-type for larger inputs (FIG. 6D).

Taken together, these unique dynamic clamp experiments provide a direct readout of the deleterious effects of $Na_v 1.2$ mutations on model neuron excitability and unequivocally demonstrate the effect of loss-of-function and gain-of-function in the presence of R853Q and R1882Q channels, respectively. Interestingly, L1536V differed from R1882Q in that the increase in action potential firing only occurred at higher stimulus currents and impacted neuronal function less pervasively, thus providing an important clue as to why the BFNIS variant may be self-limiting and also suggesting a mechanism based therapeutic approach such that drugs that reduce action potential firing at low stimulation currents could be effective in DEE patients with R1882Q or similar variation.

Materials and Methods

Patients

All patients, or their parents or legal guardian in the case of minors or individuals with intellectual disability, gave written informed consent. The study was approved by the Human Research Ethics Committee of Austin Health, Melbourne. Nineteen individuals with the R1882Q or R853Q SCN2A mutations were identified from the literature, and from an SCN2A support group (www.scn2a.org).

Clinical data was collated from the literature for previously reported individuals (N=14), with updated clinical information obtained in one patient. Individuals whose clinical data was not previously published (N=5), had their mutations identified through clinical testing. Detailed phone or clinical interviews with these parents were undertaken by paediatric epileptologists (KBH, MRC), home videos were reviewed and medical records from the treating neurologist obtained. Mutations were confirmed de novo in 15 patients, inheritance was unknown in four. The age at last review was known in 13 patients with a median age of 6.5 years (range 5 months –25 years). One patient was deceased.

Individuals with R1882Q mutations had early-onset developmental and epileptic encephalopathies (DEE) with focal seizures beginning on the first day of life; some showed marked improvement with phenytoin, and some had benefit with other sodium channel blockers. However, despite improved seizure control with phenytoin, there was no difference in developmental impairment in responders compared with non-responders, suggesting that seizure control is not sufficient to reverse the developmental impairment associated with the SCN2A mutation. All but one had severe to profound developmental delay, consistent with the 'severe neonatal-infantile' phenotype previously reported, whereas the milder phenotype in one infant was that of the 'intermediate neonatal-infantile' group.

Seizure onset occurred on day one of life in all patients with an R1882Q mutation (Table 3). Focal seizures were the initial seizure type in five; initial seizure type was unknown in two. The epileptic syndrome at onset was early infantile epileptic encephalopathy (EIEE) in three, unclassified in three and unknown in one. Seizure types evolved in six patients, including to infantile spasms in two. Seizures were ongoing at last review in the five patients for whom this information was available. Phenytoin use was reported in five patients, with improved seizure control in two and no definite effect on seizures in three. It should be noted though, that information on the doses used and blood levels reached was not available to determine whether a 'therapeutic dose' had been reached. One patient with no improved seizures had 'continuous thrashing' with phenytoin loads, being presumably an exacerbation of the movement disorder. Seizures were improved with carbamazepine in one. Two patients did not report improvement with any sodium channel blocker. At last review, six patients had severe developmental delay, and one moderate. A movement disorder was present in three patients (opisthotonus and dystonia, opisthotonus and oculogyric crises, 'thrashing movements'), absent in one, and unknown in three. Other common features included hypotonia (one of whom also had episodic appendicular hypertonia), acquired microcephaly and constipation. Two patients had normal brain imaging, one a subtle cortical dysplasia and one had T2 hyperintensities in the white matter, T1 hyperintensity in the basal ganglia and elongated superior temporal sulci.

Individuals with the R853Q mutation had later-onset DEE, with median onset of seizures at the age of 8 months, usually preceded by some degree of developmental delay. The seizure type at onset was epileptic spasms in most. In these individuals, the response to sodium channel blockers was mixed. Seizures did not improve with phenytoin; indeed, worsening was reported in one. Improved seizure control was, however, reported with other sodium channel blockers in three patients (lamotrigine, carbamazepine, both rendering a patient seizure-free; and oxcarbazepine). Movement disorders, such as dystonia, were seen in both groups; however, severe choreoathetosis only occurred with the R853Q mutation. In two of these patients, the choreoathetosis preceded seizure onset. In both groups, most patients had other types of seizures arising over time, refractory seizures and significant developmental delay.

Four previously published patients with R853Q mutation had minimal available clinical information. Two were listed as having an epileptic encephalopathy, one West syndrome (WS) and one Lennox Gastaut syndrome (LGS). More detailed clinical data was available on eight patients (Table 4). For these individuals, seizure onset occurred at a median age of eight months (range 6 months-3 years). The initial seizure type was infantile spasms in six, infantile spasms and tonic seizures in one, and tonic seizures in one. The epileptic syndrome at seizure onset was WS in seven and unclassified in one. Evolution to other seizure types was reported in seven patients, each having multiple seizure types. After evolution of seizures, the epilepsy syndrome was unclassified or unknown in all but one patient, who had LGS. Phenytoin use was reported in three patients, with no effect in two and exacerbation of seizures in one. Six patients had used other sodium channel blockers. Seizure exacerbation was noted in only one patient (on carbamazepine). One was seizure free on lamotrigine and seizure control improved on carbamazepine in one. One patient had improvement of seizures on low dose oxcarbazepine; at higher dose, seizure control remained good but there was marked worsening of overall motor function and of stimulatory behaviours. ACTH was beneficial in four patients; vigabatrin was beneficial in one and exacerbated seizures in three. Seven individuals had ongoing seizures at last review, although reduction in seizure frequency from age four years was noted in three. Development was delayed prior to seizure onset in six patients, normal in one and unknown in one. At last review, all patients had severe developmental delay. All individuals had a movement disorder; four had choreoathetosis two dystonia and two a mixed movement disorder. For three patients in whom further information on the movement disorder was available, the movement disorder had onset in infancy, predating seizure onset in two, and remaining a major medical issue in all three. Improvement was noted with L-Dopa/Carbidoba and *cannabis* (high CBD, low THC preparation) in one and triheptanoin in another. Additional features included hypotonia, severe vomiting and failure to thrive in infancy, microcephaly, extreme irritability and episodic agitation with red, hot areas of the body. Brain imaging was normal in three, showed atrophy in three, thin or hypoplastic corpus callosum in two, areas of hyperintensity on T2-weighted imaging in two and white matter volume loss in one.

TABLE 3

Clinical features and treatment response in the newly identified and previously published patients with R1882Q mutation (N = 7)

| Reference and patient (p) | Mutation inheritance | Age at last review | Age epilepsy onset (+/− severity) | Onset seizure type | Onset epileptic syndrome | Later seizure type | Later epileptic syndrome | PHT response |
|---|---|---|---|---|---|---|---|---|
| (1, 4) This study (p1) | de novo | 21 months (deceased) | 1 day | F | EIEE | T | Unclassified | Benefit |
| (1) This study (p2) | de novo | 3 years | 1 day | F | Unclassified | F | Unclassified | Benefit |
| This study (p3) | de novo | 5 years | 1 day | F | Unclassified | F, autonomic, gelastic | Unclassified | No definite benefit, movement disorder ('continuous thrashing') with phenytoin loads |
| This study (p4) | UK | 5 months | 5 months | F | Unclassified | F, T, Sp | Unclassified | No definite benefit |
| (7) (p1) | de novo | n.a. | 1 day | F | EIEE | Sp, T, TCS, gelastic | n.a. | n.a. |

TABLE 3-continued

Clinical features and treatment response in the newly identified and previously published patients with R1882Q mutation (N = 7)

| (7) (p2) | de novo | n.a. | 1 day | 'neonatal seizures' | EIEE | T, apnoeic | n.a. | n.a. |
| (6) | UK | 10.5 years | 1 day | Not applicable | n.a. | F, C | n.a. | No effect |

| Reference and patient (p) | Other sodium channel blocker response | Other AED response | Ongoing seizures at last review? | Movement disorder/ paroxysmal neurological symptoms | Development pre-seizure onset | Development at last review (+/− autism) | MRI | Other |
|---|---|---|---|---|---|---|---|---|
| (1, 4) This study (p1) | None beneficial | None beneficial | Yes | Opisthotonus, oculogyric crises | N/A (too young) | Delayed (severe) | T2 hyperintensity in white matter, T1 hyperintensity in basal ganglia, elongated superior temporal sulci | Axial hypotonia, intermittent appendicular hypertonia, acquired microcephaly, extreme irritability, severe constipation |
| (1) This study (p2) | None beneficial | Benefit with triheptanoin, CBD | Yes | Nil | N/A (too young) | Delayed (moderate) | Normal | Hypotonia, sensory issues |
| This study (p3) | None beneficial | Benefit with VPA | Yes | 'Thrashing' movements | N/A (too young) | Delayed (severe) | n.a. | Hypotonia constipation, respiratory issues |
| This study (p4) | None beneficial | None beneficial | Yes | Opisthotonus, dystonia | N/A (too young) | Delayed (severe) | Normal | Hypotonia, excess startle, elevated liver transaminases |
| (7) (p1) | n.a. | n.a. | n.a. | n.a. | N/A (too young) | Delayed (severe) | n.a. | Microcephaly |
| (7) (p2) | n.a. | n.a. | n.a. | n.a. | N/A (too young) | Delayed (severe) | n.a. | n.a. |
| (6) | CBZ- seizure reduction, OXC and LTG- no effect | None beneficial | Yes | n.a. | N/A (too young) | Delayed (severe) | Subtle cortical dysplasia | Microcephaly |

Abbreviations. AED, anti-epileptic drug; C, clonic; CBZ, carbamazepine; EIEE, Early infantile epileptic encephalopathy; F, focal; LTG, lamotrigine; MRI, magnetic resonance imaging; n.a., not available,; N/A, not assessed; OXC, oxcarbazepine; PHT, phenytoin; Sp, spasms; T, tonic; TCS, tonic clonic seizures; VPA, valproic acid

TABLE 4

Clinical features and treatment response in the newly identified and previously published patients with R853Q mutation (N = 12)

| Reference and patient (p) | Mutation inheritance | Age at last review | Age epilepsy onset (+/− severity) | Onset seizure type | Onset epileptic syndrome | Later seizure type | Later epileptic syndrome | PHT response |
|---|---|---|---|---|---|---|---|---|
| This study (p1) | de novo | 6 years | 6 months | Sp | WS | T, Sp | Unclassified | Not used |
| This study (p2) | de novo | 7 years | 8 months | Sp, T | WS | T, Sp, M | Unclassified | Exacerbated seizures |
| This study (p3) | UK (parents not tested) | 12 years | 6 months | Sp | WS | T, F, M | Unclassified | No effect |
| (6) (p1) | de novo | 6.5 years | 8 months | Sp | WS | AA, T, F | LGS | Not used |
| (6) (p2) | de novo | 8 years | 13 months | Sp | WS | T, autonomic, M | UK (EEG called 'CSWS- like') | No effect |

TABLE 4-continued

Clinical features and treatment response in the newly identified and previously published patients with R853Q mutation (N = 12)

| | | | | | | | | | |
|---|---|---|---|---|---|---|---|---|---|
| (6) (p3) | UK | 25 years | 3 years | T | Unclassified | Sp | n.a. | n.a. | |
| (3) (p1) | de novo | n.a. | n.a. | n.a. | LGS | WS | n.a. | n.a. | n.a. |
| (3) (p2) | de novo | n.a. | n.a. | n.a. | Sp | WS | n.a. | n.a. | n.a. |
| (2, 8) | de novo | UK (>6 years) | 10 months | Sp | WS | n.a. | n.a. | n.a. | |
| (5) | de novo | 2 years | 8 months | Sp | WS | F, M | n.a. | n.a. | |
| (9) (p1) | de novo | n.a. | n.a. | n.a. | n.a. | n.a. | n.a. | n.a. | n.a. |
| (9) (p2) | de novo | n.a. | n.a. | n.a. | n.a. | n.a. | n.a. | n.a. | n.a. |

| Reference and patient (p) | Other sodium channel blocker response | Other AED response | Ongoing seizures at last review? | Movement disorder/paroxysma neurological symptoms | Development pre-seizure onset | Development at last review (+/− autism) | MRI | Other |
|---|---|---|---|---|---|---|---|---|
| This study (p1) | CBZ-benefit | None beneficial, VGB exacerbated seizures | Yes (but rare after 4 years old, EEG remains abnormal) | Choreoathetosis (onset 9 months, benefit with L-Dopa/Carbidopa and cannabis (high CBD, low THC preparation) | Delayed (mild) | Delayed (severe) | White matter volume loss, thin corpus callosum | Hypotonia, vomiting and FTT |
| This study (p2) | OXC-benefit at low dose, at high dose seizures still controlled but marked worsening of motor function and stimulatory behaviours | Benefit with ACTH, THC, triheptanoin. VGB exacerbated seizures. | Yes (but infrequent after 4 years old, EEG normal) | Choreoathetosis (onset early infancy, more obvious since seizures have settled, benefit with triheptanoin) | Delayed (mild) | Delayed (severe) | Normal | Vomiting (ceased transiently with ACTH, then permanently at 3 years old) and FTT, hypotonia, extreme irritability, episodes of agitation with red, hot ears lasting minutes to hours, hypersensitivity to touch, strabismus (resolved), mildly abnormal liver function tests |
| This study (p3) | n.a. | Benefit with paraldehyde (for treatment of long clusters of seizures, VGB exacerbated seizures, ACTH no effect | Yes (but less frequent after 4 years old) | Choreoathetosis (onset early infancy) | Delayed | Delayed (severe) | Normal | Vomiting and FTT, hypotonia, extreme irritability (some improvement with VPA, GBP and amitriptyine), episodic agitation with migrating red, hot areas of body, hypersensitivity to touch and noise |

TABLE 4-continued

Clinical features and treatment response in the newly identified and previously published patients with R853Q mutation (N = 12)

| | | | | | | | | |
|---|---|---|---|---|---|---|---|---|
| (6) (p1) | CBZ-exacerbated seizures | Benefit with ACTH (seizure free-presumably means spasm free), VPA, CLB, TPM | Yes | Dystonia | Normal | Delayed (severe) | Atrophy, T2 hyperintensities (? Regions) | Microcephaly, preterm infant |
| (6) (p2) | OXC, LTG-no effect | Benefit with VGB, CLB, PB | Yes | Choreoathetosis | Delayed (moderate) | Delayed (severe) | Normal | Hypotonia |
| (6) (p3) | n.a. | Benefit with ACTH, VPA | Yes | Hand dystonia | Delayed (severe) | Delayed (severe) | CC hypoplasia | Pyramidal signs, arachnodactyly |
| (3) (p1) | n.a. | n.a. | n.a. | n.a. | n.a. | n.a. | n.a. | n.a. |
| (3) (p2) | n.a. | n.a. | n.a. | n.a. | n.a. | n.a. | n.a. | n.a. |
| (2, 8) | LTG-seizure free | n.a. | No (seizure free from 6 y 2 m, after LTG) | Dystonia, chorea, ballismus | n.a. | Delayed (severe) | Cerebral and cerebellaratrophy, thin corpus callosum | n.a. |
| (5) | LTG-'remained intractable' | Benefit with ACTH (ceased spasms) | Yes | Dystonia, chorea | Delayed | Delayed (severe) | Atrophy, T2 hyperintensities BG and thalamus | Hypotonia, microcephaly |
| (9) (p1) | n.a. | n.a. | n.a. | n.a. | n.a. | n.a. | n.a. | Listed as 'EE' with no further information provided |
| (9) (p2) | n.a. | n.a. | n.a. | n.a. | n.a. | n.a. | n.a. | Listed as 'EE' with no further information provided |

Abbreviations. AA, atypical absence; AED, anti-epileptic drug; ACTH, adrenocorticotropic hormone; CC, corpus callosum; CBD, cannabidiol; CBZ, carbamazepine; CLB, clobazam; CSWS, continuous spike wave in sleep; EEG, electroencephalogram; EE, epileptic encephalopathy; F, focal; FTT, failure to thrive; GBP, gabapentin; LTG, lamotrigine; LGS, Lennox-Gastaut syndrome; M, myoclonic; MRI, magnetic resonance imaging; n.a., not available; OXC, oxcarbazepine; PB, phenobarbital; PHT, phenytoin; Sp, spasms; T, tonic; THC, tetrahydrocannabinol; TPM, topiramate; UK, unknown; VGB, vigabatrin; VPA, valproic acid; WS, West syndrome Voltage Clamp Experiments and Curve Fitting Depolarization-activated whole-cell sodium currents ($I_{Na}$) from CHO cells transiently expressing wild-type or mutant $Na_v$ 1.2 channels were recorded using an Axopatch 200B amplifier (Molecular Devices, Sunnyvale, Calif.) controlled by a pCLAMP 9/DigiData 1440 acquisition system (Molecular Devices). Experiments were performed at room temperature (23±0.5° C.). Currents and potentials were low-pass filtered at 10 kHz and digitized at 50 kHz. Data were analysed off-line using Clampfit 9.2 (Molecular Devices) and Origin 9.0 (Microcal Software Inc., Northampton, Mass.).

The current-voltage (I-V) relationships, and $I_{Na}$ kinetics were determined by voltage-clamp protocols, as diagrammed in FIGS. 1A-1D, 2A-2C, and 4A-4B, and detailed below.

Dynamic Action Potential Clamp

Our approach is based on the dynamic action potential clamp technique, where heterologously expressed wild-type or mutant $Na_v$ 1.2 channels currents are incorporated into a biophysically realistic model of the distal AIS compartment of a cortical pyramidal neuron. In most neurons, this compartment contains the site of action potential initiation and plays a major role in in action potential firing dysfunction in epileptogenesis. The compartment model was built in Simulink (Mathworks, Australia) and it contains $Na_v$ 1.6 channel sodium current ($I_{Nav1.6}$), fast rectifying potassium current ($I_{Kv}$), synaptic current ($I_{syn}$), passive leak current ($I_{pas}$), and membrane capacitance ($C_m$). The Simulink model of the AIS compartment and the nested models of $I_{Kv}$, $I_{pas}$, $I_{syn}$, and $I_{Nav1.6}$ are shown in FIGS. 15-36. The parameters of the various conductances implemented in our model were set for performance at room temperature (23° C.), consistent with experimental conditions for recording $Na_v$ 1.2 channel $I_{Na}$ in CHO cells. As shown in FIG. 5A, the virtual cell is in current clamp mode, whereas the real CHO cell is in voltage clamp mode. The command potential for the CHO cell is the $V_m$ of the virtual cell and the wild-type or mutant $I_{Na}$ elicited in the transfected CHO cell serves as input current that replaces the original $I_{Na}$ of the virtual cell. The Simulink model is converted into C library using Matlab Real-Time Workshop, compiled and simulated using a 40-bit ADwin-Pro II processing unit (Jäger Computergesteuerte Messtechnik GmbH, Lorsch, Germany) equipped with a TigerSHARC ADSP-TS101S processor (Analog Devices, Norwood, Mass., USA) with 300 MHz clock rate, 768 kB local memory and 256 MB RAM. The processor provides support of fixed and floating-point data types and enables computationally-intensive real-time computing with precision and high speed (140 kHz). At each iteration, the instantaneous $V_m$ is calculated by solving the Hodgkin-Huxley equations of the AIS neuronal model in conjunction with the stimulus current ($I_{st}$) and the scaled wild-type or mutant $I_{Na}$ (input $I_{Na}$) from the CHO cell. The computed $V_m$ is sent back to the Axopatch 200B amplifier (Molecular Devices) as an analog command signal. As a result, the studied channel's conductance directly interacts with the virtual cell's $V_m$ and its contribution to the action potential is revealed in real-time. Data is stored as FIFO arrays in ADwin memory and can be monitored in real-time using ADgraph software provided with the ADwin package.

The characteristics of passive and active components of our AIS compartment model are identical to the published model and are described in detail Hu et al. Nat. Neurosci. 12: 996-1002, 2009. The Hu model is based on a previously published multi-compartment model underlying the full dendritic and somatic structure of a layer 5 cortical pyramidal cell, containing sodium current data and potassium current data obtained at room temperature (23° C.). Our compartment model has uniformly distributed ion channels and it is run at 23° C. to match $I_{Nav1.2}$ recording conditions. Similarly, our synaptic noise model is also based on published data.

At each iteration of the model, the $V_m$ is calculated by solving the equation:

$$(C*CellSize)\frac{dVm}{dt} = SF\_gKv*I_{Kv} + SF\_leak*I_{pas} + SF\_Syn*I_{syn} + SF\_gNaV1.6*I_{NaV1.6} + *ICellScale*I_{Cell}$$

where C is the capacitance of the compartment, CellSize is a scaling factor to change cell size and $V_m$ is the membrane potential. $SF_{gKv}$, $SF_{leak}$, $SF_{syn}$, $SFg_{Nav}$, and $I_{cellscale}$ are scaling factors for $I_{Kv}$, $I_{pas}$, $I_{Syn}$, and $I_{Nav1.6}$, respectively, whereas $I_{cellscale}$ is the scaling factor for $I_{cell}$ (the external input $Na_v$ 1.2 current). In all experiments, the voltage dependent $Na_{v1.6}$ current was set to zero unless stated otherwise. FIGS. 15-36 show the nested models of the individual current components described using the Hodgkin-Huxley formalism.

To increase the flexibility of the model, the variable parameters (e.g., peak conductance and reversal potential for different ion-channels) can be modified as input arguments in ADbasic, the programming language of the ADwin system. Parameter setting in ADwin and data are automatically saved on a hard disk for further analysis. Subthreshold voltage responses or firing of the AIS model were elicited by using two methods, consisting of either 0 to 30 pA step current injections in 2 pA increments commanded via the Clampex module of pCLAMP 9 software or enabling synaptic current input generating directly within the ADwin-Pro II processing unit and input to the in silico model. To approximate synaptic background activity, we adapted a stochastic model that exploits the Ornstein-Uhlenbeck process and generates synaptic current as a sum of two independent excitatory and inhibitory synaptic conductances ($g_e$ and $g_i$, respectively), as previously described. Various $g_e$:$g_i$ ratios were set by scaling the mean and standard deviation of $g_e$ and keeping $g_i$ unchanged. Typically, the $V_m$ of our model produced constant fluctuations (FIG. 6A) and the average resting $V_m$ (around −70 mV) exhibited more depolarised mean values with increasing $g_e$:$g_i$ ratios (FIGS. 6C and 6E). The latter method represents a more realistic approximation of realistic post-synaptic signalling. Ionic currents in the virtual cell in combination with wild-type $I_{Na}$ from the CHO cell result in control activity (action potential firing), whereas mutant $I_{Na}$ results in activity that mimics excitatory neuron behavior in a patient from which the mutant channel was derived. Before undertaking dynamic clamp experiments, the background (endogenous) current ($I_{background}$), present in the voltage-clamped CHO cell is estimated and subtracted using the linear leak subtraction control of the Axopatch 200B amplifier. In all dynamic clamp experiments, the heterologously expressed wild-type or mutant $I_{Na}$ recorded in the CHO cell is multiplied by a scale factor ($F_s$). To assign the $F_s$ value for the $I_{Na}$, the peak $I_{Na}$ amplitude is first determined in voltage clamp mode by recording current-voltage relationships elicited from HP values of −120 and −70 mV. Then, in dynamic clamp mode, the $I_{Na}$ amplitude is scaled to a magnitude value similar to the original model cell's sodium current amplitude (~350 pA). $I_{Na}$ is typically downscaled (approx. 10-15-fold), thus $I_{background}$ contribution to the experiment can be considered as negligible. We did not adjust for possible differences between wild-type and mutant $I_{Na}$ densities expressed in CHO cells, thus differences in action potential firing are mainly attributed to the altered biophysical properties of the given $Na_v$ 1.2 channel variant. In all dynamic clamp experiments, the non-scaled and scaled input $I_{Na}$, the stimulus waveform, the $V_m$, and the total synaptic current in the model cell were simultaneously recorded. We systematically evaluated the model cell's robustness by scaling the Cm and/or the various conductances in the AIS compartment, and analysing the interaction between the passive and/or the active model features in the presence of external wild-type or mutant $Na_v$ 1.2 channel $I_{Na}$ (FIGS. 7A-7B, 8A-8B, 9A-9C, 10A-10B, 11A-11E, 12A-12B, 13A-13B, and 14-36).

Rheobase was determined as the minimal stimulus current needed to elicit an action potential. Input-output relationships were determined as the number of action potentials elicited during injections of step currents of 500 ms or 1 s duration, or as the firing frequency of the model cell in response to synaptic currents of various $g_e$:$g_i$ ratios during a 5 s recording. Action potential threshold was defined using the first derivative method to determine $V_m$ at 10 mV/ms point during an action potential upstroke. The action potential half-width was measured as the period between the trace's crossing the half-amplitude point in its rising and decaying stages. Action potential upstroke velocity was defined as the maximum value of the first derivative of the action potential waveform. The amplitude of the input $I_{Na}$ was determined during action potential firing. All action potential and $I_{Na}$ parameters were determined using Clampfit except action potential rise (upstroke velocity), which was estimated in Axograph X (Axograph Scientific, Sydney, Australia).

Statistical Analysis

Data are presented as mean±SEM; n, number of experiments. Statistical comparison between more than two groups was performed using one-way analysis of variance followed by Bonferroni post hoc test. Two-way repeated measures ANOVA followed by the Holm-Sidak post-hoc test was used for comparing the $Na_v$ 1.2 channel variants and the different firing frequencies. Statistical significance is defined by $P<0.05$.

Plasmids

The SCN2A plasmid encoding the adult isoform of the human $Na_v$ 1.2 channel (pcDNA3.1(+)-$Na_v$ 1.2) has been previously described. The R853Q mutation is located in the voltage sensor of domain 2. L1563V is in the second segment of domain 4, and R1882Q in the COOH terminus (FIG. 1A). The R853Q mutation was introduced with QuikChange site-directed mutagenesis (Agilent Technologies, Santa Clara, Calif.) using forward and reverse primers GTTCTCCGATCATTCCAGCTGCTCCGAGTTTTC (SEQ ID NO: 1) and GAAAACTCGGAGCAGCTGGAATGATCGGAGAAC (SEQ ID NO: 2), respectively. The pcDNA3.1(+) plasmids, containing the human $Na_v$ 1.2 channel with the L1563V or R1882Q mutations, were generated commercially (TOP Gene Technologies, Quebec, Canada). All clones were verified by automated DNA sequencing (Australian Genome Research Facility).

Cell Culture and Transfections

Chinese hamster ovary (CHO) cells were cultured in Dulbecco's Modified Eagle Medium: Nutrient Mixture F-12 (Thermo Fisher Scientific, Waltham, Mass.) supplemented with 10% (v/v) fetal bovine serum (Thermo Fisher Scientific) and 50 IU/ml penicillin (Thermo Fisher Scientific) at 37° C. with 5% $CO_2$. The cells were grown in T25 $cm^2$ flasks (BD Biosciences, San Jose, Calif., USA) to ~80% confluency, and then transiently co-transfected with wild-type or mutant pcDNA3.1(+)-$Na_v$ 1.2 (4 µg) and enhanced green fluorescent protein (eGFP; 1 µg; Clontech, Mountain View, Calif.), using Lipofectamine 3000 Reagent (Thermo Fisher Scientific). After transfections, cells were incubated at 37° C. in 5% $CO_2$. 24 hours post-transfection, the cells were detached using TrypLE Express Reagent (Thermo Fisher Scientific), plated on 13 mm diameter glass coverslips (Menzel-Glaser, Thermo Fisher Scientific), and incubated at 30° C. in 5% $CO_2$. Electrophysiological recordings were performed 48 to 72 hours post transfection.

Electrophysiology

Cells were placed into a ~0.1 ml recording chamber and superfused with extracellular solution at a constant rate of ~0.2 ml/min. The extracellular bath solution contained 145 mM NaCl, 5 mM CsCl, 2 mM $CaCl_2$), 1 mM $MgCl_2$, 5 mM glucose, 5 mM sucrose, 10 mM Hepes (pH=7.4 with NaOH and osmolarity of ~305 mosmol $l^{-1}$), whereas the intracellular solution contained 5 mM CsCl, 120 mM CsF, 10 mM NaCl, 11 mM EGTA, 1 mM $CaCl_2$, 1 mM $MgCl_2$, 2 mM Na2ATP, 10 mM Hepes (pH=7.3 with CsOH and osmolarity of ~290 mosmol $l^{-1}$).

Experiments were performed at room temperature (23±0.5° C.) set by a TC344B Dual Automatic Temperature Controller (Warner Instruments, Hamden, Conn.). Patch electrodes were pulled from borosilicate glass capillaries (GC150TF-7.5, Harvard Apparatus Ltd.) and typically exhibited resistance values of 1.2-1.5 MΩ. Liquid junction potentials were corrected and series resistance values, typically of 2-2.5MΩ, were 90-95% compensated. To minimize possible voltage errors, only relatively small CHO cells of 15-25 pF cell capacitance ($C_m$=22±1 pF, n=168), expressing peak $I_{Na}$ amplitudes larger than 2 nA but smaller than 10 nA, were selected. $I_{Na}$ amplitudes that fall outside the selected range would introduce errors in dynamic action potential clamp experiments (see below). Approximately 10-20% of the transfected cells showing green fluorescence did not express functional ion channel protein or exhibited peak $I_{Na}$ values of very small (a few tens to a hundred pA) to small (<2 nA) amplitudes, and were excluded from analysis. Cells with peak $I_{Na}$ values exceeding 10 nA, recorded in ~5-10% of cells expressing wild-type or L1563V channels, in less than 5% in cells expressing R853Q channels, and in ~10-20% of cells expressing R1882Q channels, were also excluded. Finally, cells were excluded from the analysis if the amplitude of the leak current at a holding potential (HP) of −120 mV was larger than 2% of the peak $I_{Na}$. The contribution of endogenous $I_{Na}$ to the total $I_{Na}$ was considered as negligible. The leak and capacitive currents were corrected using a −P/4 pulse protocol unless mentioned otherwise. In the experiments using tetrodotoxin, $I_{Na}$ was determined as the current blocked by 100 nm tetrodotoxin (Alomone Laboratories, Israel).

The current density, voltage dependence of $I_{Na}$ activation and inactivation, recovery from inactivation, and development of slow inactivation were determined using the voltage protocols depicted in the figures. In most voltage clamp experiments, the HP was −120 mV; however recovery from inactivation was determined from HP values of −120 and −70 mV, because recovery is voltage dependent and, in dynamic clamp experiments (see below), the free running resting membrane potential ($V_m$) of the AIS compartment model cell was approximately −70 mV. Peak $I_{Na}$ was defined as the difference between peak and steady-state currents recorded during depolarization and when keeping the cell at HP, respectively. Current-voltage (I-V) relationships were determined by measuring peak $I_{Na}$ during 40-ms depolarizing voltage steps ranging from −80 to +60 mV, at 0.5 Hz. Peak $I_{Na}$ was converted to peak conductance by the equation G=I/(V−$V_{rev}$), where $V_{rev}$ is the sodium channel reversal potential. The resulting normalized conductance-voltage relationships are plotted as G/$G_{max}$ values versus voltage and are referred to as 'activation' curves. The voltage dependence of steady-state fast inactivation was obtained using pre-pulses of 100 ms duration in 5 mV increments in the voltage range between −120 and +10 mV, followed by a 10-ms voltage step to −5 mV. Steady-state activation and inactivation curves were fit using the Boltzmann equation:

$$\frac{G}{G_{max}} = \frac{1}{\left[1 + e^{(V-V_{0.5})/k}\right]},$$

where V is the conditioning voltage, $V_{0.5}$ is the half-maximal (in)activation voltage, and k is a slope factor. The steady-state open probability ($P_o$) was estimated in the voltage range between −100 mV and +40 mV in 5 mV increments, by multiplying the values of fractional activation and inactivation. Results were expressed as the m×h product as a function of $V_m$ and were fit with a bi-Gaussian peak function:

$$m = Ae^{-0.5\left[\frac{x-x_c}{w_1}\right]^2}, x < x_c, \text{ and}$$

$$h = Ae^{-0.5\left[\frac{x-x_c}{w_2}\right]^2}, x \geq x_c,$$

where m represents the probability that the channel is activated, and h is the probability that a channel is not inactivated, A represents the peak (height) of the curve, $x_c$ represents the $V_m$ value corresponding to the peak of the fitted curve, $w_1$ and $w_2$ represent the width of the $V_m$ range of m and h, respectively. It should be noted that the m parameter for activation is derived directly from the measurement of G/$G_{max}$, different from the Hodgkin-Huxley m parameter based on $m^3$ kinetics. The magnitude of the window current was estimated by calculating the overlapping area under the Boltzmann equations describing the activation and inactivation, in the voltage range between −100 mV and +60 mV as follows:

$$\text{Area} = \int_{-100}^{V_0} \frac{1}{1 + e^{((V-V_{0.5,act})/k_{act})}} dV + \int_{V_0}^{+60} \frac{1}{1 + e^{((V-V_{0.5,inact})/k_{inact})}} dV,$$

where $V_0$ is the voltage value where the crossover of the activation and inactivation curves occurs, $k_{act}$ and $k_{inact}$ are the slope factors of activation and inactivation, respectively, $V_{0.5,act}$ and $V_{0.5,act}$ are the $V_m$ values for half-maximal voltage of activation and inactivation, respectively. The window current was expressed as percent of total area (Table 2). It should be noted that this procedure is only an approximate method to predict steady-state current, because the activation curve does not accurately represent steady-state activation, as it is derived from a measurement of non-steady-state peak transient current, where activation may not be at steady-state and inactivation has already progressed to some degree. Persistent $I_{Na}$, expressed as percent of peak $I_{Na}$, was determined at 40 ms after the onset of the step voltage command by either subtracting traces recorded in the presence of tetrodotoxin from control, or by estimating inward $I_{Na}$ after −P/4 leak correction. Both methods resulted in similar values and for comprehensive mutant and wild-type data analysis the −P/4 method was used. To determine the time constants of peak $I_{Na}$ inactivation elicited at various voltages, the time course of individual $I_{Na}$ traces was fitted with a double-exponential equation:

$$\frac{I}{I_{max}} = A_f e^{-t/\tau_f} + A_s e^{-t/\tau_s},$$

where t is time, $A_f$ and $A_s$ are the fractions of the fast and slow inactivation components, and $T_f$ and $T_s$ are the time constants of the fast and slow inactivating components, respectively. The fast time constant ($T_f$) was plotted against the test potential V, in the range between −40 mV and +10 mV. Voltage dependence of recovery from (fast) inactivation was assessed from HP values of either −120 or −70 mV with a paired-pulse protocol comprising a 10 ms pre-pulse to −10 mV (P1), which served to fast-inactivate the $I_{Na}$, followed by a test pulse to −10 mV (P2), to measure $I_{Na}$ availability after variable recovery intervals. Recovery was analysed by fitting a single exponential function to the data to obtain the time constant, ti as follows:

$$\frac{I}{I_{max}} = 1 - e^{-t/\tau},$$

where t is time (here the delay between pre-pulse P1 and test pulse P2). To evaluate the rate of entry into slow inactivation that develops during prolonged membrane depolarization or repeated high-frequency firing, the HP was kept at −60 mV for time intervals of increasing duration (0.005 s-195 s). Between the intervals, the membrane was hyperpolarized to −120 mV for 20 ms, allowing channels recover from fast inactivation, and then $I_{Na}$ availability was assessed with a 2-ms test pulse to −10 mV. In similar experiments, we also determined the entry into slow inactivation at −50 mV for wild-type and mutant currents, respectively. The development of slow inactivation was evaluated by fitting data with the double-exponential equation above.

Parameters of Action Potentials and Input $I_{Na}$ in Dynamic Clamp Experiments

Rheobase was determined as the minimal stimulus current needed to elicit an action potential. Input-output relationships were determined as the number of action potentials elicited during injections of step currents of 500 ms or 1 s duration, or as the firing frequency of the model cell in response to synaptic currents of various $g_e$:$g_i$ ratios during 5 s recordings. Action potential upstroke velocity was defined as the maximum value of the first derivative of the action potential waveform. Action potential threshold was determined at the 10 mV/ms upstroke velocity value, using the first derivative method. The action potential half-width was measured as the period between the trace's crossing the half-amplitude point in its rising and decaying stages. The amplitude of the input $I_{Na}$ was determined during action potential firing. All action potential and $I_{Na}$ parameters were determined using Clampfit except action potential rise (upstroke velocity), which was estimated in Axograph X (Axograph Scientific, Sydney, Australia).

Pore Current Recordings

The extracellular bath solution contained 125 mM NaCl, 20 mM guanidine-sulfate, 2 mM $CaCl_2$), 1 mM $MgCl_2$, 10 mM Hepes (pH=7.3 with NaOH), whereas the intracellular solution contained 135 mM CsF, 5 mM NaCl, 1 mM EGTA, 10 mM Hepes (pH=7.3 with NaOH). In some experiments, the extracellular solution contained 60 mM guanidine-sulfate instead of 20 mM.

Discussion

SCN2A has emerged as a major gene implicated in neonatal, infantile and even childhood onset epilepsies, with a number of distinct epilepsy syndromes recently recognised. Many of these are also associated with cognitive and behavioral impairments that range in type and severity. Analyses of SCN2A mutations suggest a correlation between variant clinical presentation, functional impact and pharmacosensitivity. Here we studied two of the most recurrent DEE mutations, R1882 with early-onset DEE and R853Q with infantile spasms. We undertook a clinical and biophysical analysis to explore the mechanisms underpinning the distinctive phenotypes produced by these variants and contrast these findings with L1563V associated with the self-limited syndrome of BFNIS.

The clinical features and treatment response in the newly identified and previously published patients with R853Q, R1882Q, and L1563V mutations are summarised in Table 5. R853Q and R1882Q result in DEE, whereas L1563V causes self-limited, pharmacoresponsive epilepsy. We confirm and expand upon a previous report of distinct phenotypic segregation between R1882Q and R853Q cases suggesting that the biophysical consequences, unique to each variant, would be major determinants of clinical phenotype. The clinical presentations with these two mutations differ in seizure onset age and seizure type. Further, there is emerging evidence of differences in the type of movement disorder (choreoathetosis in those with R853Q mutations), presenting symptom (seizures in R1882Q, developmental delay in R853Q) and pharmacosensitivity (discussed below).

TABLE 5

General clinical features and treatment response of patients with epilepsy and/or developmental delay

| Phenotypic group | | | Age seizure onset | Onset seizure type | Seizures improve with PHT? | Seizures improve with other Na$_v$ channel blockers? | Other seizure types later | Ongoing seizures after infancy? | Movement disorder/paroxysmal neurological symptoms | Developmental delay (+/− autism) |
|---|---|---|---|---|---|---|---|---|---|---|
| | 'Benign' epilepsy (BFNIS) e.g., L1563V | | 0-13 months | Focal | Unknown | Unknown | No | No | No | No |
| 'Severe' epilepsy | 'Early-onset' e.g., R1882Q | Intermediate Severe | 0-3 months | Focal | Variable (marked benefit some) | Variable (may improve) | No Variable | Variable Yes | Variable Yes | Variable (normal-mod. DD) Yes (severe-profound DD) |
| | 'Late-onset' e.g., R853Q | | >3 months | Spasms | No (may worsen) | Variable (reports of both benefit and worsening) | Yes | Yes | Yes (may predate Sz) | Yes (moderate-severe DD, DD predates Sz) |

BFNIS, benign familial neonatal infantile seizures; Sz, seizures; DD, developmental delay; PHT, phenytoin To better understand the genotype-phenotype correlations due to SCN2A mutations, we complemented voltage clamp analysis, which models the biophysical consequences of a given variant, with dynamic clamp analysis, which more accurately predicts the contribution of Na$_v$ 1.2 channel mutations to neuronal excitability and the neurophysiological consequences of such variants. Results show unequivocally that the R1882Q variant leads to gain-of-function and increased neuronal excitability, whereas the R853Q variant results in loss-of-function and decreased neuronal excitability, and finally the L1563V mutation only produces an enhanced excitability profile in the presence of higher intensity stimuli.

The functional changes in R853Q channels, determined by voltage clamp analysis, include a negative shift of the steady-state inactivation and an enhanced entry into slow inactivation, suggesting a loss-of-function phenotype as compared to wild-type channels. This observation was highlighted and strengthened by dynamic clamp analysis that showed a dramatic reduction in action potential firing across a range of input currents that was a far greater loss-of-function than that might be predicted by intuitive interpretation of voltage clamp data.

In voltage clamp experiments, R1882Q channels exhibited shifts in both activation and inactivation curves and slower fast inactivation. These changes, combined, underpin gain-of-function. In addition, disrupted inactivation can provide a causative mechanism for increased persistent I$_{Na}$. Persistent I$_{Na}$ can reduce the current needed to reach action potential threshold and supports subthreshold oscillations and repetitive action potential firing. Dynamic clamp experiments using realistic stimuli with R1882Q channels showed that the sum of all the biophysical changes contributed to a more a depolarized V$_m$ that could have significant impacts by further contributing to enhanced excitability.

An increase in neuronal excitability was also seen with the L1563V channels, albeit only in the presence of a relatively high stimulus strength, and to a lesser degree than the R1882Q channel. However, in dynamic clamp mode, a typical AIS model cell incorporating L1563V channels is capable of switching between normal activity and increased action potential firing modes when stimulus current strength increases above a critical magnitude. This functional profile would be impossible to intuit from voltage clamp analysis of the L1563V variant given the relatively small but opposing changes of the activation and inactivation curves and an enhanced recovery from fast inactivation compared with wild-type, highlighting a strength of the dynamic action potential clamp method in providing meaningful frameworks for understanding variant functional mechanisms.

More complex aspects of AIS and SCN2A biology will also need to be considered in future studies. In future dynamic action potential clamp studies, the complexity of the virtual model can be increased by adding not only different and additional conductances but also adding somatic and/or dendritic compartments capable of mimicking more realistic morphology. In the cortex, Na$_v$ 1.2 is expressed in excitatory pyramidal cells and somatostatin (SST)-expressing interneurons; the impacts of each type of mutation at a network level are not yet known. Previous studies in animal models show that the specific expression pattern and subcellular localization of Na$_v$ 1.2 channels in the AIS correlates with age and neuron type, implying that Na$_v$ 1.2 channel dysfunction may have the biggest effect on AIS function in infants. It has been proposed that loss of Na$_v$ 1.2 channel function due to de novo missense mutations is associated with autism spectrum disorder (ASD). However, our data demonstrate that Na$_v$ 1.2 channel mutations resulting in loss-of-function may also constitute a plausible cellular pathomechanism for later-onset DEE and that not only gain of function mutations can lead to epilepsy syndromes as previously suggested. The mechanism underlying the paradoxical observation that loss of function in Na$_v$ 1.2 can lead to infantile seizures and epilepsy is unknown and needs further studies.

In vivo, the V$_m$ of cortical pyramidal neurons exhibits subthreshold fluctuations due to the spatiotemporal integration of excitatory and inhibitory inputs. In dynamic clamp experiments, action potential firing in the AIS compartment model could efficiently be initiated by depolarizing current steps or in response to scalable g$_e$:g$_i$ input mimicking a realistic synaptic environment. The specific functional changes in our dynamic clamp data may underpin the distinct phenotypes in infants with R1882Q and R853Q mutations. Further work will be required to confirm that other SCN2A mutations causing 'early-onset' and 'later-onset' DEE segregate gain-of-function and loss-of-function effects, respectively. Detailed understanding of molecular mechanisms in individuals with SCN2A DEE is needed to guide development of urgently-needed precision medicine approaches. For this, channel dysfunction and the likely associated cellular pathomechanisms will need to be co-investigated.

So far, the relationship between functional effect of the SCN2A mutation and response to sodium channel blockers remains incompletely understood. There have been no clinical trials of these drugs in SCN2A-associated epilepsies. As may be expected with a gain-of-function mutation, some patients with R1882Q mutations become seizure free with phenytoin. However, improvement with phenytoin was not universal and other sodium channel blockers were less effective. It is perhaps not surprising that reduction of seizures with drugs seen is some patients with DEE fail to improve development as the cellular and network scale impacts of the SCN2A mutation are likely to extend beyond epileptogenesis into cognitive and movement functions and highlighting the need for more specific mechanisms that fundamentally modify disease progression and address seizures and co-morbidities. Given the loss-of-function impact the R853Q variant would have on neurons it is perhaps not surprising that sodium channel blockers are usually contraindicated. Infantile spasms and subsequent epilepsy may emerge as a secondary consequence of altered neuronal firing in R853Q patients further complicating the use of sodium channel blockers as they could be beneficial to reducing seizures but may paradoxically exacerbate the underlying loss-of-function in sodium channel activity. This is reflected in clinical observations of both seizure exacerbation and benefit in different patients yet in one patient cessation of treatment led to an overall improvement in function despite seizures returning and suggesting that sodium channel blockers may provide no net benefit in those with R853Q mutations. Further study of the effects of sodium channel blockers in both groups is required, including considering differential effects of different drugs, high and low drug doses, and impacts at different ages, on different seizure types and development. The differential functional and phenotypic effects of the SCN2A mutations suggest that novel treatments will need to be tailored to the functional impacts of the mutation; it is unlikely that a single treatment strategy for all SCN2A-associated disorders will be effective.

Dynamic clamp analysis provides clear benefits over voltage clamp analysis. The output is in the interpretation friendly format of action potential firing, without the need to intuitively or computationally interpret voltage clamp recordings and with significantly less burden on experimenter time; with a day or two of dynamic clamp recording providing a definitive analysis of variant impact on excitability versus weeks of voltage clamp analysis. In our experiments, heterologous expression of the a subunit alone was sufficient for generating functional $Na_v 1.2$ channels, although the lack of subunit and the heterologous channel environment may have affected $Na_v 1.2$ channel function in the hybrid neuron as it would for traditional voltage clamp studies. Limitations of the dynamic action potential clamp technique such as the reliance on the mathematical description of model cell ionic currents, or issues relating to the scaling of the implemented ionic current, have been reviewed elsewhere. In CHO cells, $I_{Na}$ densities of R853Q channels were smaller, whereas those of R1882Q channels were larger compared to wild-type (FIG. 1). In dynamic action potential clamp experiments, down-scaling of the R853Q input $I_{Na}$ exacerbated loss-of-function, whereas the up-scaling of the input R1882Q $I_{Na}$ exacerbated gain-of-function (FIGS. 12A-12B, 13A-13B, and 15-36). Yet, it is uncertain to what extent the heterologous expression of $Na_v 1.2$ channel variants in mammalian cells can replicate the true expression levels of the variants in neuronal membranes.

Dynamic clamp is well positioned as a rapid diagnostic and will supplant voltage clamp analysis for modeling of voltage gated ion channels. Further developments of real-time models that incorporate heterosynaptic modeling of ligand gated channels could offer a broader impact of this approach in epilepsy and other neurogenetic diseases. With advances in real-time computation platforms, the ability to implement more complex in silico models enhances our ability to evaluate the impact of variants in different brain networks for separable prediction of effects on cognition, movement and other functions such as respiration and cardiac control that may impact sudden unexpected death in epilepsy (SUDEP) and other co-morbidities seen in epilepsy. A recent study shows how inexpensive it is to add a dynamic clamp on every rig. Dynamic clamp is well positioned to impact drug discovery by providing a disease state relevant model that should allow a more predictive link to clinical effect than currently used voltage clamp assays whilst exploiting the same biological and instrumentation resources.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of determining whether mutation in an ion channel or a receptor is a gain-of-function or loss-of-function mutation, the method comprising:
   a) providing a dynamic clamp in electrical contact with a biological cell or portion thereof comprising a mutant ion channel or receptor for providing a waveform;
   b) causing the dynamic clamp to apply a signal based on modulation of the mutant ion channel in the biological cell or portion thereof, thereby providing the waveform at the biological cell or portion thereof; and
   c) detecting modulation of the waveform at the biological cell or portion thereof, wherein modulation of the waveform is determined relative to a control, wherein if the modulation of the waveform is increased compared to the control, then the mutation is a gain-of-function mutation, and if the modulation of the waveform is decreased compared to the control, then the mutation is a loss-of-function mutation.

2. The method of claim 1, wherein the control comprises a biological cell or portion thereof comprising a wild-type ion channel or receptor.

3. The method of claim 1, wherein the waveform is an action potential.

4. The method of claim 1, wherein the dynamic clamp applies:
   a voltage signal to the biological cell or portion thereof, and wherein modulation of the waveform at the biological cell or portion thereof is detected by measuring a current signal at the biological cell or portion thereof; or
   a current signal to the biological cell or portion thereof, and wherein modulation of the waveform at the biological cell or portion thereof is detected by measuring a voltage signal at the biological cell or portion thereof.

5. The method of claim 1, wherein the ion channel is selected from the group consisting of a sodium channel, a potassium channel, a calcium channel, and a chloride channel.

6. The method of claim 5, wherein the ion channel is a sodium channel selected from the group consisting of SCN1A, SCN2A, SCN3A, SCN4A, SCN5A, SCN8A, SCN9A, SCN10A, and SCN11A.

7. The method of claim 6, wherein the SCN channel is SCN1A or SCN2A.

* * * * *